(12) United States Patent
Hua

(10) Patent No.: US 12,240,810 B2
(45) Date of Patent: Mar. 4, 2025

(54) CHIRAL-SUBSTITUTED POLY-N-VINYLPYRROLIDINONES AND COMPLEXES WITH BIMETALLIC NANOCLUSTERS AND USES THEREOF IN ASYMMETRIC OXIDATION REACTIONS

(71) Applicant: Kansas State University Research Foundation, Manhattan, KS (US)

(72) Inventor: Duy H. Hua, Manhattan, KS (US)

(73) Assignee: Kansas State University Research, Manhattan, KS (US)

( * ) Notice: Subject to any disclaimer, the term of this patent is extended or adjusted under 35 U.S.C. 154(b) by 794 days.

(21) Appl. No.: 17/428,070

(22) PCT Filed: Feb. 4, 2020

(86) PCT No.: PCT/US2020/016536
§ 371 (c)(1),
(2) Date: Aug. 3, 2021

(87) PCT Pub. No.: WO2020/163295
PCT Pub. Date: Aug. 13, 2020

(65) Prior Publication Data
US 2022/0204447 A1 Jun. 30, 2022

Related U.S. Application Data

(60) Provisional application No. 62/800,823, filed on Feb. 4, 2019.

(51) Int. Cl.
| | | |
|---|---|---|
| *C07D 205/08* | (2006.01) | |
| *B01J 35/50* | (2024.01) | |
| *C07D 207/28* | (2006.01) | |
| *C07D 211/78* | (2006.01) | |
| *C07D 305/12* | (2006.01) | |
| *C07D 307/33* | (2006.01) | |
| *C07D 309/30* | (2006.01) | |
| *C07D 471/04* | (2006.01) | |
| *C07D 471/22* | (2006.01) | |
| *C07D 487/04* | (2006.01) | |
| *C07J 1/00* | (2006.01) | |
| *C08F 126/10* | (2006.01) | |
| *C08F 226/10* | (2006.01) | |
| *B82Y 30/00* | (2011.01) | |
| *B82Y 40/00* | (2011.01) | |

(52) U.S. Cl.
CPC ............ *C07D 205/08* (2013.01); *B01J 35/50* (2024.01); *C07D 207/28* (2013.01); *C07D 211/78* (2013.01); *C07D 305/12* (2013.01); *C07D 307/33* (2013.01); *C07D 309/30* (2013.01); *C07D 471/04* (2013.01); *C07D 471/22* (2013.01); *C07D 487/04* (2013.01); *C07J 1/00* (2013.01); *C08F 126/10* (2013.01); *C08F 226/10* (2013.01); *B82Y 30/00* (2013.01); *B82Y 40/00* (2013.01)

(58) Field of Classification Search
USPC ........................................................ 528/423
See application file for complete search history.

(56) References Cited

U.S. PATENT DOCUMENTS

2023/0279170 A1* 9/2023 Hua .................. B01J 23/52
526/264

FOREIGN PATENT DOCUMENTS

| EP | 0338435 | 10/1989 | |
|---|---|---|---|
| WO | 2017172763 | 10/2017 | |
| WO | WO-2017172763 A1 * | 10/2017 | ............. B01J 23/52 |

OTHER PUBLICATIONS

International Search Report and Written Opinion in corresponding PCT/US2020/016536, dated Jun. 9, 2020.
Hao, et al., "Chiral Substituted Poly-N-vinylpyrrolidinones and Bimetallic Nanoclusters in Catalytic Asymmetric Oxidation Reactions", J Am Chem Soc, 2016, 138(51), pp. 16839-16848.
Dinari, et al., "Ultrasound-assisted one-pot preparation of organo-modified nano-sized layered double hydroxide and its nanocomposites with polyvinylpyrrolidone", J Polym Res, 2014, 21, 8 pages.

* cited by examiner

Primary Examiner — Terressa Boykin
(74) Attorney, Agent, or Firm — Hovey Williams LLP

(57) ABSTRACT

Chiral polyvinylpyrrolidinone (CSPVP), complexes of CSPVP with a core species, such as a bimetallic nanocluster catalyst, and enantioselective oxidation reactions utilizing such complexes are disclosed. The catalytic complexes have exhibited the ability to achieve reaction products have a very high degree of optical purifies. These reaction products can be used as reagents in the synthesis of complex organic molecules, such as bioactive products, and C—H bond oxidation of complex molecules including various drugs and natural products.

25 Claims, 13 Drawing Sheets n = 436; MW 92,000

CHIRAL-SUBSTITUTED POLY-N-VINYLPYRROLIDINONES AND COMPLEXES WITH BIMETALLIC NANOCLUSTERS AND USES THEREOF IN ASYMMETRIC OXIDATION REACTIONS

CROSS-REFERENCE TO RELATED APPLICATIONS

The present application is the U.S. National Stage of International Patent Application No. PCT/US2020/016536, filed Feb. 4, 2020, which claims the benefit of U.S. Provisional Patent Application No. 62/800,823, filed Feb. 4, 2019, entitled CHIRAL-SUBSTITUTED POLY-N-VINYLPYRROLIDINONES AND COMPLEXES WITH BIMETALLIC NANOCLUSTERS AND USES THEREOF IN ASYMMETRIC OXIDATION REACTIONS, each of which is incorporated by reference in its entirety herein.

STATEMENT REGARDING FEDERALLY SPONSORED RESEARCH OR DEVELOPMENT

This invention was made with government support under Grant No. CHE 1662705 awarded by the National Science Foundation and Grant No. R01 GM128659 by the National Institutes of Health General Medical Science. The content is solely the responsibility of the inventors and does not necessarily represent the official views of the National Institutes of Health. The government has certain rights in the invention.

BACKGROUND OF THE INVENTION

Field of the Invention

The present invention is generally directed toward chiral substituted polyvinylpyrrolidinone compounds that can be, among other things, complexed with catalytic materials, such as bimetallic nanoclusters, to provide catalysts for various asymmetric oxidation reactions producing reactions products having a high degree of optical purity and high chemical yields.

Description of the Prior Art

Over the past decades, functionalization of alkenes has been one of the most studied reactions in organic synthesis. Particularly, catalytic asymmetric syn-dihydroxylation has been intensely pursued, and the Sharpless asymmetric dihydroxylation process is a major breakthrough and one of the highest achievements in asymmetric catalysis. However, there are a few shortfalls in the methodology, which include: a lower enantioselectivity in some Z-1,2-disubstituted alkenes, alkenes containing stereogenic centers, and the toxicity and volatility of $OsO_4$ catalyst. Various improvements on the enantioselectivity of syn-dihydroxylation have been made, including the uses of microencapsulated $OsO_4$ on polysulfone, polyamine-anion-osmate/Sharpless chiral ligands, and enzyme-osmate. Other asymmetric dihydroxylations with osmium-free catalysts including palladium-catalyzed functionalization of alkenes, $RuO_4$, $KMnO_4$, iron complexes, and Pd(II)—(R)-quinox. Non-asymmetric oxidants such as ruthenium nanoparticles/hydroxyapatite $[Ca_5(PO_4)_3(OH)]$ with $NaIO_4$—$H_2SO_4$, molybdenum complexes, $(NH_4)_2Ce(NO_3)_6$, $SeO_2$, $NaIO_4$, and ozone have also been used in the non-asymmetric dihydroxylation of alkenes.

Regio- and enantioselective oxidation of unactivated C—H bond of alkanes and cycloalkanes is one of the most challenging transformations in organic synthesis. The preferred site of C—H bond oxidation often takes place because of the lower C—H bond dissociation energy (such as tertiary<secondary<primary), through-bond electronic effect, steric effect, conjugation and hyperconjugation, releasing strain, and directing group. The uses of homogeneous catalysts such as iron complexes and other reagents in C—H oxidation have been reported. Due to various possible reactive sites in even medium-sized organic molecules, the regio- and enantio-selective C—H oxidations inevitably require directing or activating groups such as tertiary hydroxyl or allylic moieties. C—H oxidation is a highly atom-economic process, and enantio- and regio-selective asymmetric C—H oxidation would provide a powerful tool for organic and medicinal chemists to build chiral molecules.

International Publication No. WO 2017/172763, by the current inventor, describes catalytic asymmetric syn-dihydroxylation of alkenes using 0.5 mol % Pd/Au (3:1) and a first-generation chiral-substituted poly-N-vinylpyrrolidinone (CSPVP) along with $O_2$. This work discovered that the use of toxic osmium metal could be avoided while improving enantioselectivities thereby advancing the catalytic asymmetric synthesis of diols from alkenes. While good enantioselectivity was achieved for certain oxidation reactions, it was later discovered that this first-generation catalyst did not provide optimum results for other oxidation reactions.

Thus, a need exists for a new class of CSPVPs that can be complexed with catalytic materials, such as bimetallic nanoclusters (e.g., Pd/Au and Cu/Au), to provide enhanced chiral oxidation reactions through improved assessment of the C—H oxidative sites.

SUMMARY OF THE INVENTION

In one embodiment, the present invention is generally directed toward a second generation of chiral-substituted poly-N-vinylpyrrolidinones (CSPVP), possessing a C3,4-{2,2-dialkyl-[1,3]dioxane} moiety and having the general formula

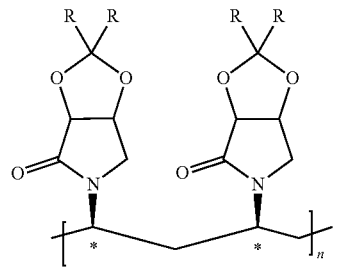

wherein each R is independently selected from aliphatic or aromatic functional groups and n is greater than 50.

These CSPVP polymers, when complexed with catalytic nanoclusters, have been found to provide a greater stereoselectivity than the first generation CSPVP described in WO 2017/172763, which is incorporated by reference herein in its entirety, in the catalytic asymmetric oxidations of alkenes and alkanes. These polymers also are stable over longer periods time, can be used in reaction conditions over 120° C. for several days, and are recoverable after the catalytic oxidation reactions.

In certain embodiments, the CSPVPs are synthesized from D-isoascorbic acid (an inexpensive starting material) or D-ribose in six or seven steps. The CSPVP synthesized from D-isoascorbic acid has the general structure (I)

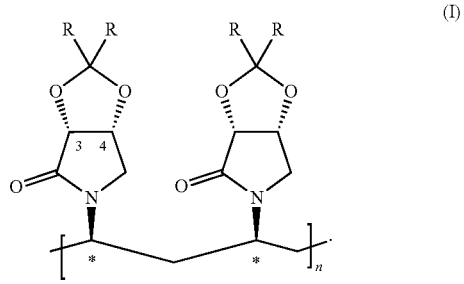

This CSPVP polymer exhibits a 3S,4S configuration and may be referred to herein as (S,S)—CSPVP.

The CSPVP synthesized from D-ribose has the general structure (II) and exhibits a 3R,4R configuration (referred to herein as (R,R)—CSPVP).

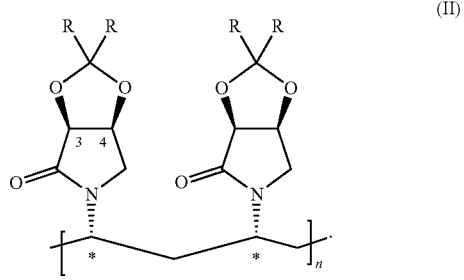

Particular bimetallic nanoclusters comprising the CSPVPs exhibit excellent enantioselectivity (greater than 90% ee in some embodiments) in the catalytic oxidation of substituted cycloalkenes and alkenes and excellent enantio- and regioselectivies in the catalytic oxidation of cycloalkanes. Moreover, various chiral lactones and lactams can be produced via catalytic asymmetric desymmetrization/ring closing reactions of α,α-disubstituted dienes. These chiral lactones and lactams can be converted to bioactive natural products such as (−)-penibruguieramine A, (−)-malyngolide, omuralide, lactacystin, salinosporamide A, oxazolomycin, and others. Medium-sized and complex bioactive natural products also undergo regioselective C—H oxidation reactions to furnish oxidized analogs, which may enhance bioactivity and are available for subsequent functional group transformation.

DETAILED DESCRIPTION OF THE PREFERRED EMBODIMENT

Figure 1:
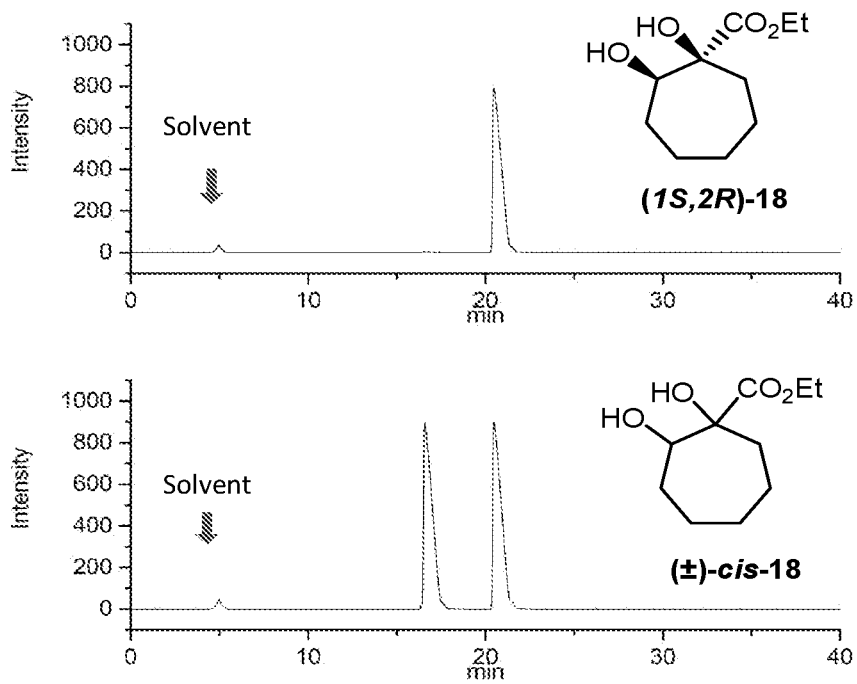
FIG. 1 depicts HPLC-chiral column graphs for (1S,2R)- and (±)-cis-Ethyl 1,2-dihydroxycycloheptane-carboxylate (18)

One embodiment of the present invention pertains to chiral-substituted poly-N-vinylpyrrolidinones (CSPVPs) such as those that are synthesized from D-isoascorbic acid or D-ribose. The CSPVP can be used as stabilizers of nanoparticle catalysts, especially bimetallic nanoparticle catalysts, such as those described below in great detail. The CSPVP-stabilized catalysts can be used in reactions that provide valuable chiral molecules such as chiral cycloalkanediols, alkanediols, cycloalkanones, α-amidocycloalkanones, lactones and lactams. Moreover, various bioactive natural products and complex molecules can be oxidized regio- and stereo-selectively. These "late-stage" aliphatic C—H oxidation of complex molecules and the total syntheses of bioactive natural products, including pharmaceuticals, can produce a number of synthetic intermediates for possible structural modification in improving or altering pharmacological or biological properties. The oxidized drugs may assist the investigation of oxidative mechanisms in cells and bodies. The reactions can also be used to study the metabolic pathways of various oxidative enzymes in human guts and gut microbiota (microbacteria) such as human cytochrome P450 and UDP glucuronosyl transferase (UGT) supersomes. Some of the oxidized chiral molecules are difficult to obtain by other methods. The oxidation reactions involve catalytic amounts of CSPVPs and environmentally friendly metals such as copper, gold, and palladium (low toxicity), and oxygen or hydrogen peroxide as the oxidant. The Food and Drug Administration has approved PVP for various uses including binders of various pharmaceuticals and disinfectant.

It is believed that in the complex of chiral substituted PVP and bimetallic nanoclusters (NCs), C3 and C4 substituents on the pyrrolidinone ring of PVP affect the stereochemical outcome of the reactions, resulting in asymmetric oxidation.

In one embodiment, the CSPVP possesses a C3,4-{2,2-dialkyl-[1,3]dioxane} moiety and has the general formula

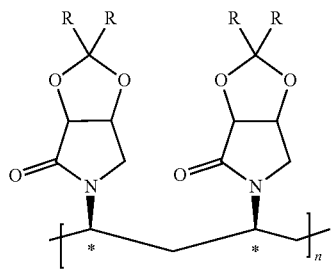

wherein each R is independently selected from aliphatic or aromatic functional groups, and preferably each is independently selected from the group consisting of $CH_3$, $CH_2CH_3$, $CH_2CH_2CH_3$, $CH(CH_3)_2$, $CH(cyclohexyl)_2$, Ph (phenyl), and aryl (Ar) and n is greater than is 50. In other embodiments, each R comprises a functional group having at least 1 carbon atom selected from the group consisting of ethers, aliphatic hydrocarbons, aromatic hydrocarbons, and combinations thereof. In particular embodiments, at least one R group comprises a functional group having at least 5 carbon atoms, at least 8 carbon atoms, or at least 10 carbon atoms. In other embodiments, at least one R group comprises from 3 to 30 carbon atoms, from 5 to 25 carbon atoms, or from 8 to 20 carbon atoms. In still other embodiments, n is at least 250, at least 300, or at least 400. In particularly preferred embodiments, ii is from about 50 to about 500, from about 125 to about 400, or from about 150 to about 350. In certain embodiments, the CSPVP compound has a molecular weight of at least 50,000, at least 60,000, or at least 70,000. In particular embodiments, the CSPVP compound has a molecular weight of from about 50,000 to about 120,000, from about 60,000 to about 110,000, or from about 70,000 to about 100,000. In still other embodiments, at least one R group is selected from the group consisting of $CH_2Ph$, $CH_2O$-t-Bu, $CH(CH_3)_2$, $CH_2$(1-Naph), $CH_2OH$, $CH_2OCHPh_2$. In some embodiments all R groups are the same; however, this need not always be the case.

In another embodiment, the R groups of the CSPVP can be hydrolyzed, such as with HCl and water, to provide the following polymer

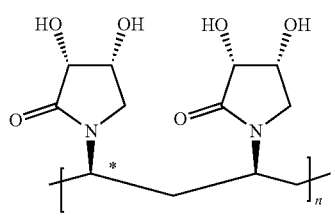

This polymer is water soluble and can be used for interaction with DNA, RNA, or protein molecules. It can also be used to prepare other chiral polymers using a $S_N2$ displacement reaction by the treatment of the hydroxyl polymer with NaH and RBr (R=alkyl, aryl, $CH_2OCH_2CH2OR$, heterocycle).

Nanoparticle clusters (also referred to as nanoclusters) are useful as catalysts in numerous chemical reactions. However, the catalytic activity of the nanocluster is largely dependent upon the material not aggregating into larger particles, which many nanoclusters will naturally tend to do in certain reaction environments. The CSPVP molecules described herein can also be used as stabilizers for various core species including nanoclusters, nanoparticles, and biomolecules such as DNA, RNA (e.g., siRNA and dsRNA), and proteins. Chiral recognition using chiral PVP can be achieved from the interaction with the biomolecule, thereby allowing either selective isolation or detection or delivery of specific biomolecules. Hence the present invention can be used in separation, detection, and nanodelivery of biomolecules.

Nanoclusters can be prepared by a number of methods including molecular beams, chemical reduction, thermal decomposition of transition metal complexes, ion implantation, electrochemical synthesis, radiolysis, sonochemical synthesis, and biosynthesis. In one embodiment, the nanoclusters comprise a metal. In preferred embodiments, the metal is present in its elemental, or zero valence, form, either alone as a monometal catalyst or alloyed with other metals. In particular embodiments, the nanoclusters comprise one or more transition metals, especially a transition metal selected from the group consisting of Au, Pd, Cu, Rh, Ce, Mo, Ni, Ru, W, and Fe. In certain embodiments, the nanoclusters are generally spherical and exhibit average particle to diameters of from about 1 to about 10 nm, from about 2 to about 50 nm, or from about 3 to about 25 nm.

In one particular embodiment, the nanoparticles comprise bimetallic materials. Exemplary bimetallic materials comprise those including Au as one of the metallic species due to its high electron-positivity, catalytic activity, and synergistic electronic effects, such as Pd/Au, Cu/Au, Ce/Au, Mo/Au, W/Au, Ni/Au, Rh/Au, Ru/Au, and Fe/Au. It was discovered that the bimetallic materials Pd/Au and Cu/Au when formed into CSPVP-stabilized nanoclusters are particularly preferred. In particular, Pd/Au—CSPVP nanoclusters are particularly suitable for the oxidation of alkenes. Cu/Au—CSPVP nanoclusters are particularly suitable for oxidation of cycloalkanes and for cleaving terminal C═C. The electronegativity values for Au, Pd, and Cu are 2.54, 2.20, and 1.90, respectively, suggesting that in the Pd/Au and Cu/Au bimetallic nanoclusters gold pulls electrons from (or depolarizes) Pd or Cu and subsequently induces a greater positive Pd or Cu atom. This in turn affords a more electrophilic Pd or Cu resulting in a more reactive electron acceptor metal atom for the reactions with alcohols, alkenes, and alkanes.

The preparation of CSPVP-stabilized Pd/Au nanoclusters is exemplified by the following synthesis scheme.

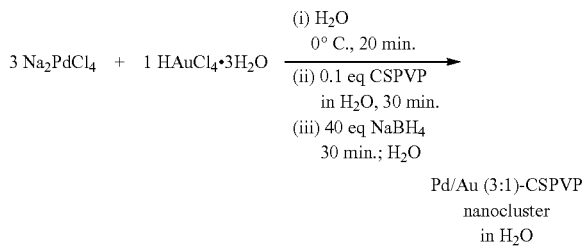

In embodiments comprising Cu/Au nanoclusters, CuCl is substituted for $Na_2PdCl_4$ in the above synthesis scheme.

In certain embodiments, the ratio between the first transition metal component, preferably Pd or Cu, and Au can be from about 0.5:1 to about 5:1, from about 1:1 to about 2:1 to about 3:1, or about 3:1. In certain preferred embodiments comprising Pd/Au—CSPVP nanoclusters, the ratio of Pd:Au:CSPVP is about 30:10:1.

The bimetallic-CSPVP nanoclusters can be used to catalyze a number of oxidation reactions to provide reaction products having a high level of optical purity. More specifically, the nanoclusters catalyze reactions that are highly enantioselective providing a relatively high enantiomeric excess of one enantiomer. Enantiomeric excess is defined as the percent of one enantiomer minus the percent of the other enantiomer. In certain embodiments, the reactions catalyzed with the nanoclusters described herein result in an enantiomeric excess of greater than 80%, greater than 85%, greater than 90%, greater than 95%, or greater than 98%.

Exemplary oxidation reactions that can be performed include enantioselective oxidation of cycloalkanediols (also described in WO2017/172763), asymmetric oxidation of alkenes, asymmetric oxidation of unactivated C—H bonds, desymmetrized ring closing reactions, and regioselective C—H oxidation of complex molecules. A number of these reactions are described in further detail below. The reaction products formed via the asymmetric oxidation reactions can be quite useful as reagents in the synthesis of various bioactive compounds, such as synthesized bioactive natural products. Certain functional groups of the reaction products can be readily substituted with, for example, other organic groups so as to provide the desired bioactive compound. These reaction products and the bioactive compounds produced therefrom exhibit a high level of optical purity without having undergone a separate separation step to isolate a particular enantiomer In certain embodiments, the catalytic materials comprising the CSPVPs are quite stable permitting them to be used in reactions conducted over extended periods of time and under elevated temperature conditions. For example, the catalytic materials resist degradation at reaction temperatures of 50° C., 70° C., 100° C. or higher, for periods of 2 days, 3 days, 5 days, 7 days or more. In addition, the catalytic materials are storage stable exhibiting a shelf-life at room temperature (approximately 25° C.) of at least 6 months, at least 1 year, or at least 1.5 years.

Synthesis of CSPVP (or Substituted PVPs Containing Stereogenic Centers)

The synthesis of the CSPVPs according to the present invention is illustrated in Scheme 1, below.

Scheme 1. Synthesis of Second Generation Chiral-Substituted PVPs. and Stereochemistry of the Oxidation of Alkenes.

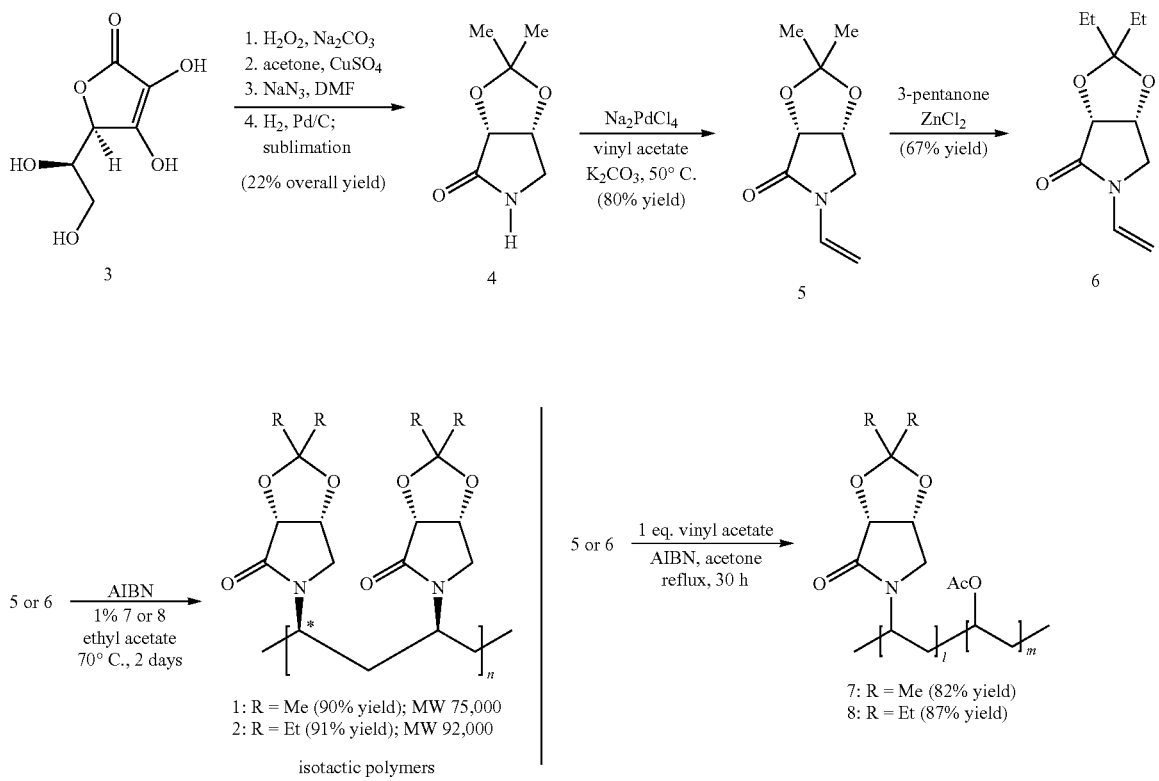

-continued

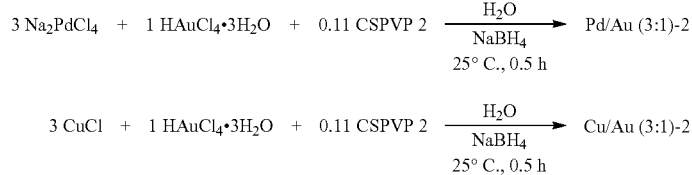

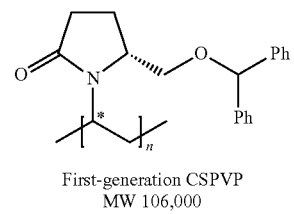

First-generation CSPVP
MW 106,000

The reaction scheme began with optically pure D-isoascorbic acid (3), an inexpensive starting material (2.5 Kg/$96) as compared with chiral amino acids, especially the unnatural amino acids in the synthesis of the first-generation CSPVPs. The reaction scheme involved the polymerization of chiral N-vinylpyrrolidinone 5, which was made from the vinylation of pyrrolidinone 4. Chiral 4 was prepared from D-isoascorbic acid (3) as illustrated. Hence, 3 was converted to 4 by a sequence of reactions: (i) oxidative cleavage of 3 with 30% hydrogen peroxide and sodium carbonate; ketalization of the resulting D-erythronolactone with acetone and copper sulfate; (iii) $S_N2$-type ring opening of the lactone with sodium azide in DMF at 100° C.; and (iv) reduction of the azido function with hydrogen and Pd/C in methanol followed by heating/sublimation of the crude product. N-Vinylation of 4 with $Na_2PdCl_4$ and vinyl acetate at 50° C. gave N-vinylpyrrolidinone 5 in 80% yield. It is understood that other reaction mechanisms known in the art and capable of achieving the same products may be substituted for those shown in Scheme I. For example, the vinylation of 4 can be performed with n-butyl vinyl ether and 5 mol % of 4,7-diphenyl-1,10-phenanthroline palladium bis(trifluoroacetate) [(DPP)Pd(OCOCF$_3$)$_2$] and n-butyl vinyl ether at 75° C. to give vinyllactam 5. This reaction is described in Brice, J. L.; Meerdink, Stahl, S. S., Formation of enamides via palladium(II)-catalyzed vinyl transfer from vinyl ethers to nitrogen nucleophiles. *Org. Lett.* 2004, 6, 1845-1848.

Figure 17:
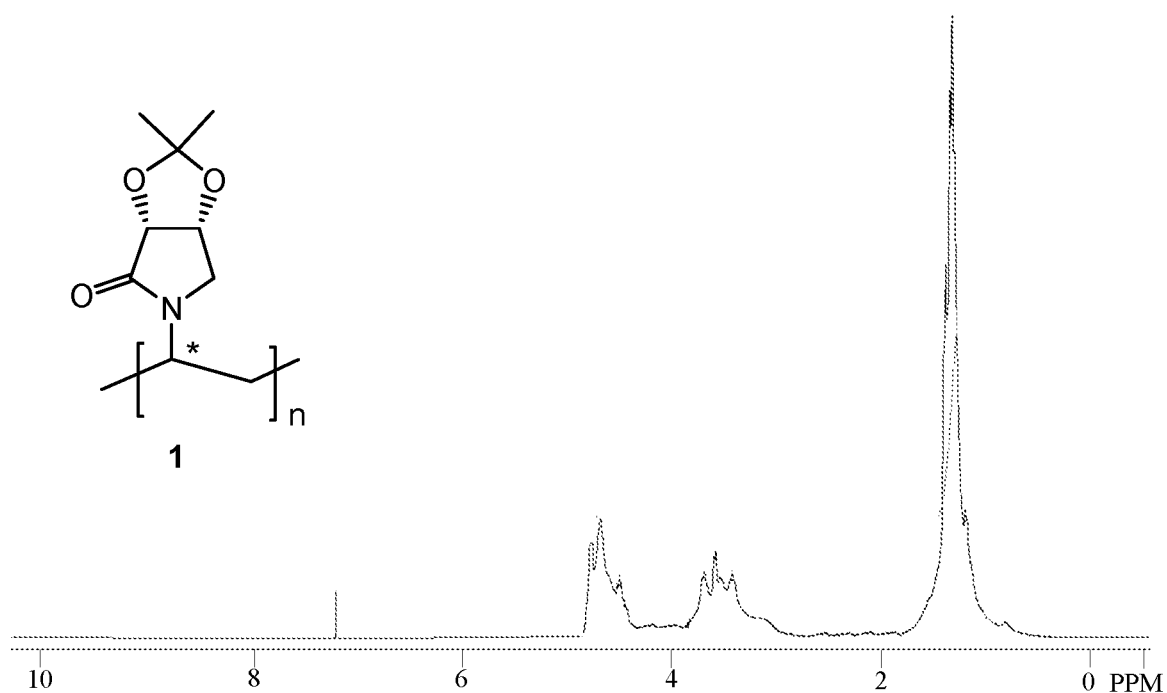
FIG. 17 depicts a proton NMR spectrum for polymer 1.
Figure 18:
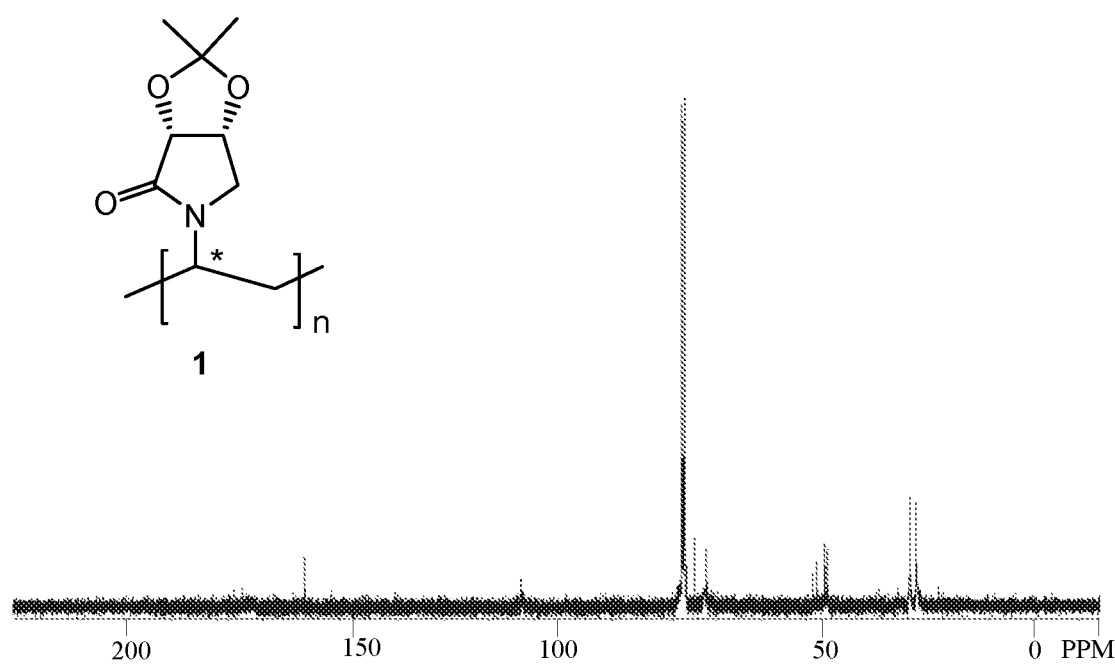
FIG. 18 depicts a carbon-13 NMR spectrum for polymer 1.
Figure 19A:
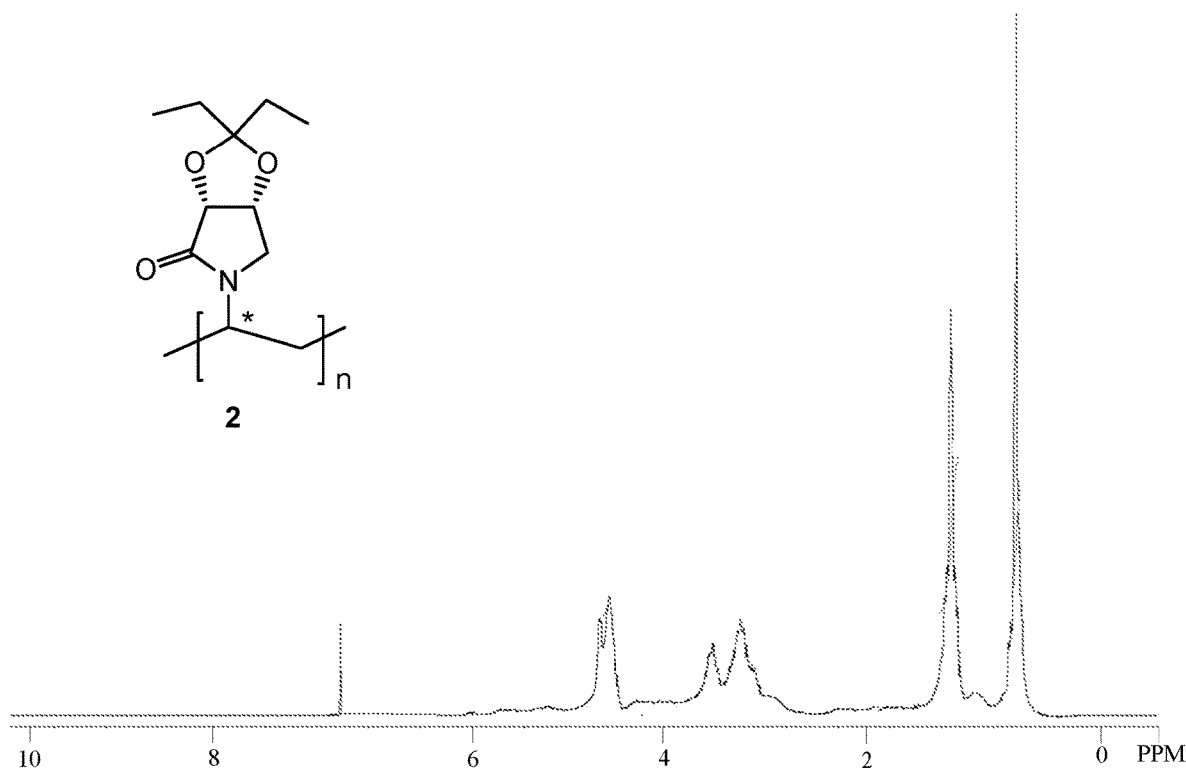
FIG. 19A depicts a proton NMR spectrum for polymer 2.
Figure 19B:
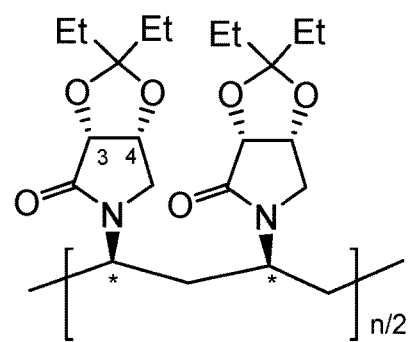
FIG. 19B depicts a carbon-13 NMR spectrum for polymer 2.
Figure 19B:
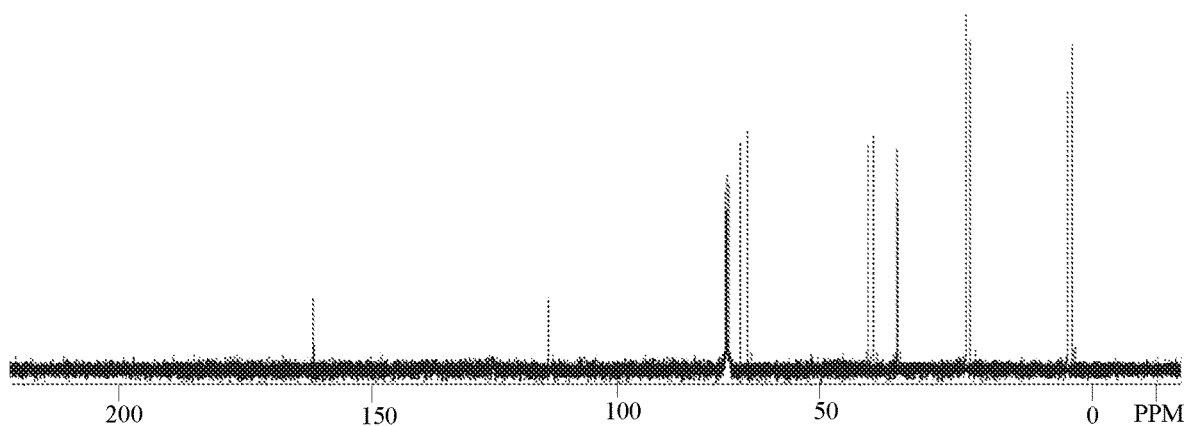

A ketal-exchange reaction was found by the treatment of acetonide S with 3-pentanone and dried $ZnCl_2$ (catalytic amount) at 65° C. to give pantanolide 6 (67% yield). Following a dispersion polymerization protocol, polymer 1 was prepared in a 90% yield by heating vinyl pyrrolidinone 5, 1% of copolymer 7, and a catalytic amount of azobisisobutyronittile (AIBN) in ethyl acetate at 70° C. for 2 days. Similarly, polymer 2 was made from 6 and 1% copolymer 8 in a 91% yield. The molecular weights of 1 [75,000 (n=~410)] and 2 [92,000 (n=~436)] were determined by gel permeation chromatography (GPC) using TSKgel GMHxl column and THF as solvent with a flow rate of 1 mL/min. Copolymer 7 was prepared from 5, vinyl acetate (1 equiv.), 1% AIBN under refluxing acetone. Similarly, copolymer 8 was made from 6 (87% yield). The $^{13}C$ NMR spectra of polymers 1 and 2 suggest that they possess an isotactic stereochemistry in the polymer backbone (indicated with * in 1 and 2; Scheme 1). See, FIGS. 18 and 19B. For example, the $^{13}C$ NMR spectrum of polymer 1 (FIG. 18) shows only 10 signals having δ values (in ppm) of 161.0 (C=O), 113.0 (O—C—O), 74.7 (C—O), 72.1 (C—O), 48.7 (C—N), 47.8 (C—N), 46.1 (CH$_2$), 45.6 (CH$_2$), 27.2 (CH$_3$), and 25.9 (CH$_3$). Similarly, $^{13}C$ NMR spectrum of 2 (FIG. 19B) shows 12 signals. The simplicity of signals suggests a symmetry in the polymer structures, which is in agreement with that reported $^{13}C$ NMR data of isotactic polystyrene. The average sizes, size distribution, and shapes of polymers 1 and 2 were measured by atomic force microscopy (AFM) and dynamic light scattering (DLS). FIGS. 17 and 19A are $^1H$ NMR spectra for polymers 1 and 2, respectively.

The opposite stereochemistry polymer of 2, 105 (see Scheme 6) or 2S (see Scheme 1A), can be synthesized from (2S,3S)-4-amino-4-deoxy-2,3-O-isopropylidene-D-erythronolactam (4S; the enantiomer of 4), which was obtained from D-ribose. This synthetic scheme is illustrated in Scheme 1A, below.

Scheme 1A. Synthesis of 3S,4S-Chiral Polymers [(S,S)-CSPVPs].

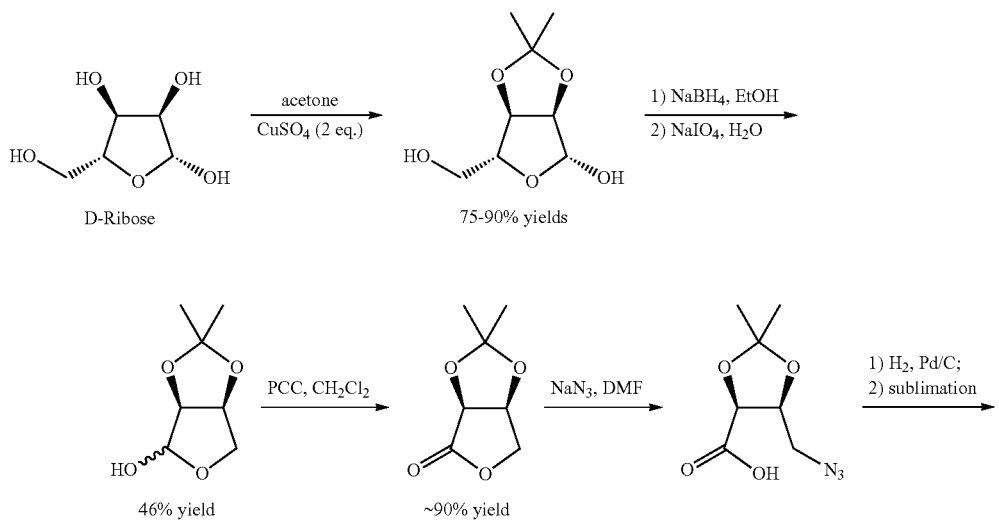

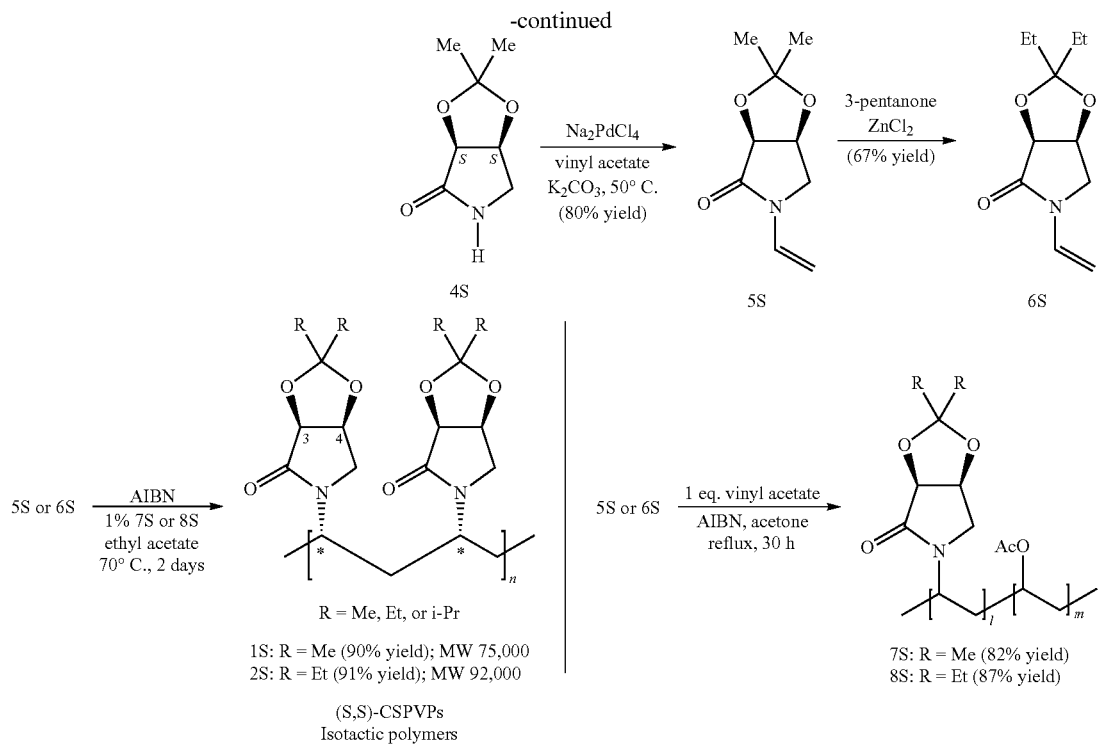

D-Ribose was used as the starting material for the preparation of the enantiomer of (R,R)—CSPVP as depicted in Scheme 1A. Acetonide formation of D-ribose was accomplished by the reaction with acetone (used as reagent and solvent) in the presence of 2 equivalents of copper sulfate. This acetonide sugar was converted into the lactol by the treatment with sodium borohydride in ethanol followed by the cleavage of the resulting 1,2-diol with sodium periodate in water. The lactol was then oxidized cleanly with pyridinium chlorochromate (PCC) in dichloromethane to give the lactone in ~90% yield. The conversion of this lactone to (S,S)—CSPVP was performed by following the sequence of reactions for the synthesis of (R,R)—CSPVP (1 and 2) as noted above. Alternatively, D-ribose can be protected with 3-pentanone and $H_2SO_4$ in DUE followed by reduction with sodium borohydride and oxidative cleavage by $NaIO_4$, and Swern oxidation with oxalyl chloride and DMSO to give the corresponding pentanolide lactone. The pentanolide lactone can then be treated with $NaN_3$ in DMF at 120° C. followed by hydrogenation with $H_2$ over Pd—C and sublimation (150° C./0.1 mm Hg) to give the corresponding pentanolide lactam of 4S. Vinylation of this pentanolide lactam can be carried out with n-butyl vinyl ether and 5 mol % of (DPP) Pd(OCOCF$_3$)$_2$ followed by polymerization to give 2S.

Synthesis of Bimetallic Nanoclusters-CSPVP and Characterization

Figure 16:
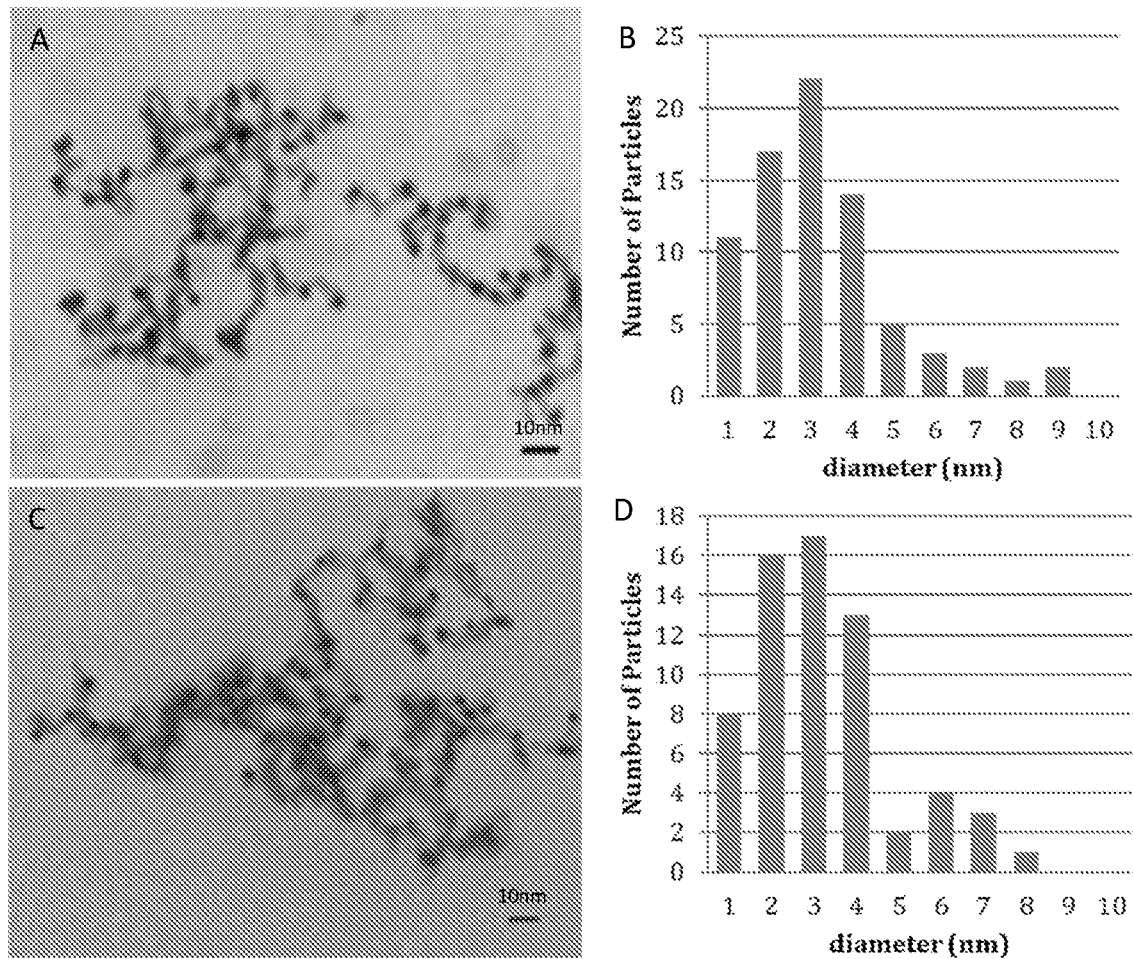
FIG. 16 depicts (A) a representative TEM image of nanocluster Pd/Au (3:1)-2; (B) measurement of the diameter of the nanoclusters and the average size is 3.32±1.08 nm; (C) a representative TEM image of nanocluster Cu/Au (3:1)-2; and (D) measurement of the diameter of the nanoclusters and the average size is 3.41±1.13 nm, bars are 10 nm.
Figure 20:
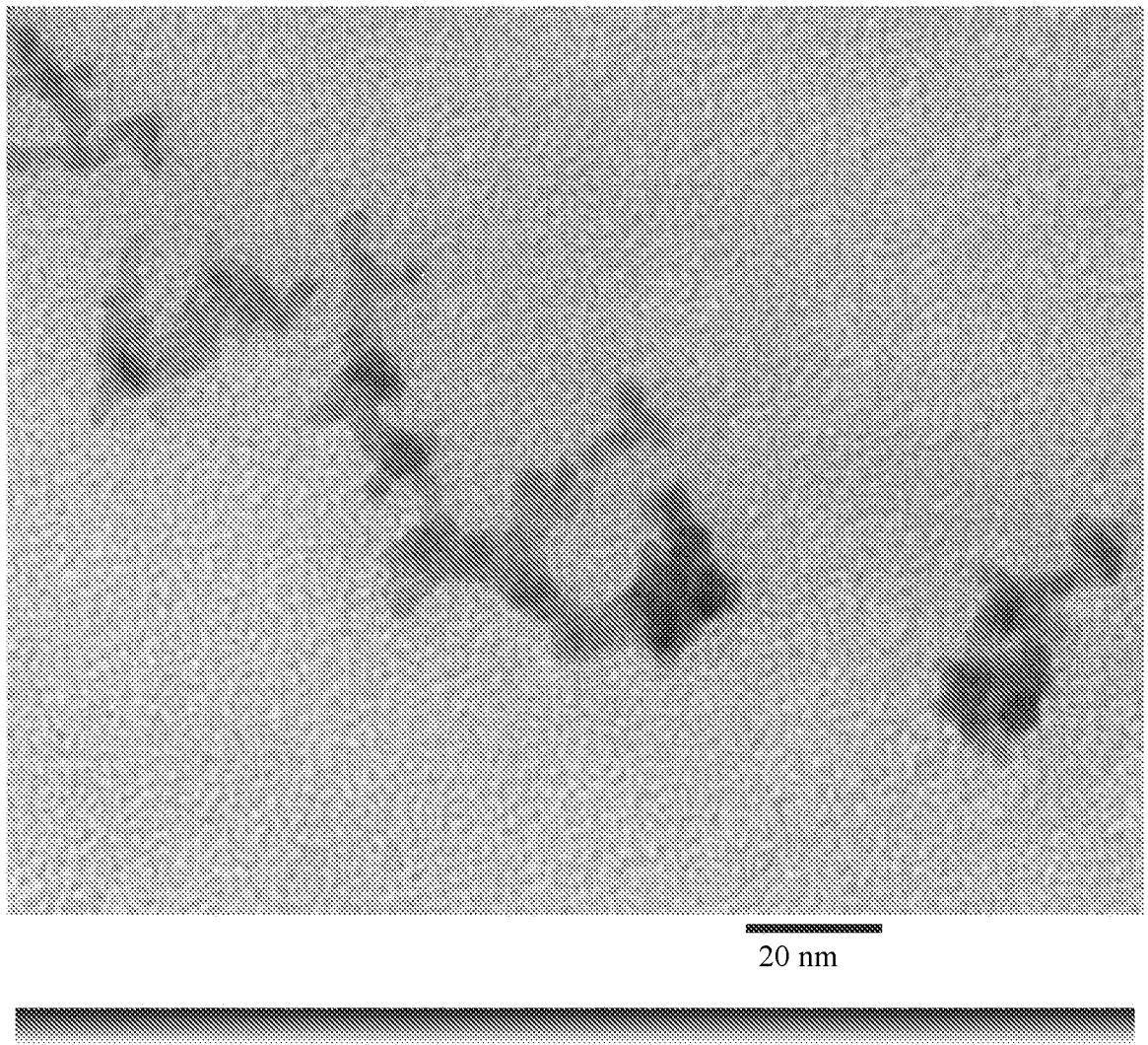
FIG. 20 is a TEM image of Cu—Au (3:1)-2.

Nanoclusters (NCs) can be prepared by a number of methods including chemical reduction, thermal decomposition, ion implantation, electrochemical synthesis, sonochemical synthesis, and biosynthesis, and they can be characterized by various analytical techniques. In accordance with one embodiment of the present invention, various bimetallic NCs including Pd/Au and Cu/Au, were synthesized using the chemical reduction method in the presence of chiral polymer 1 or 2. The polymer is needed to stabilize nanometer sized particles. Gold is used in the bimetallic NC framework due to its synergistic electronic effects. For example, a solution of $Na_2PdCl_4$ (3 equiv), $HAuCl_4$ (1 equiv), and CSPVP 2 (0.11 equiv; based on the moles of Au) in water was treated with $NaBH_4$ at 25° C. for 30 min (see, Scheme 1 above) to give a clear light brown solution, revealing a homogeneous solution. The resulting solution was used in the catalytic asymmetric oxidation reactions, described below, without further manipulation. Similarly, Cu/Au (3:1)-2 was also prepared using CuCl (3 equiv), $HAuCl_4$ (1 equiv), CSPVP 2 (0.11 equiv) and $NaBH_4$. For analysis, the aforementioned crude NC solution was filtered through a Vivaspin 20 centrifugal filter device (3,000 MWCO) and washed with deionized water twice to remove low MW inorganic materials. The resulting NC was dissolved in water and subjected to various analyses including inductively coupled plasma-mass spectroscopy (ICP-MS), transition electron microscopy (TEM), AFM, DLS, and IR. TEM showed the sizes of the NCs being ~3.0 nm. See, FIGS. 16 (A) and (B) for Pd/Au (3:1)-2, and FIGS. 16 (C) and (D) and FIG. 20 for Cu/Au (3:1)-2, The amide C=O absorption band of the pyrrolidinone ring at 1648 cm$^{-1}$ of polymer 2 in IR spectrum shifted to 1642 cm$^{-1}$ of Pd/Au (3:1)-2 and 1643 cm$^{-1}$ for Cu/Au-2, suggesting a greater character of $^{\delta-}O—C=N^{\delta+}$ of the amide group in the NCs than that of 2, due to chelation with the metals. The approximate total numbers of metal atoms and molecules of polymer in a spherical NC (from TEM) were calculated using magic-cluster sizes $N_{total=1/3}(10 n^3 – 15 n^2 + 11 n – 3)$, where n is the number of layers of shell in the NCs. There are ~727 atoms of Pd/Au (3:1) in a NC stabilized by ~20 molecules of polymers. The catalysts are recyclable and can be reused for the oxidation reaction under similar reaction conditions albeit with lower catalytic activities but maintaining excellent optical yields. Notably, under similar reaction conditions, in the absence of CSPVP, reduction of $Na_2PdCl_4$ and $HAuCl_4$ with $NaBH_4$ does not produce water-soluble NCs. Instead, insoluble black solids formed.

Catalytic Asymmetric Oxidation

In all cases, the optical purities were measured by HPLC/chiral column (Chiralpak AD(-H) column; Daicel Chem. Industries). Racemic oxidized compounds were synthesized independently and used for HPLC/chiral column analyses. After screening various ratios of the bimetallic NCs, a 3:1 ratio of Pd/Au or Cu/Au appeared to provide the highest catalytic activity and enantioselectivity, hence this ratio was used for all the experiments described below.

Catalytic Asymmetric Oxidation of Alkenes

In this study of stereoselectivity, both CSPVPs 1 and 2 gave excellent enantioselectivity in the oxidation of alkenes. However, in several representative asymmetric C—H oxidations of cycloalkanes and desymmetrized ring-closing reactions, 2 produced greater % enantiomeric excesses (ee's) than 1, hence 2 was used and results from 2 were described. The oxidation of additional seven alkenes, 9-15, with 0.5 mol % of Pd/Au (3:1)-2 and $O_2$ (30 psi) at 50° C. for 3 days was examined. The results are summarized in Table 1.

TABLE 1

Catalytic asymmetric oxidation of alkenes $$R\text{—CH=CH—}R' \xrightarrow[O_2 \text{ (30 psi), } H_2O, 50° C., 3 \text{ days}]{0.5 \text{ mol \% Pd/Au (3:1)-2}} R\text{—CH(OH)—CH(OH)—}R'$$

| entry | substrate | product(s) | % yield(s) | % ee |
|---|---|---|---|---|
| 1 | cyclopentene-CO₂Et (9) | diol-CO₂Et (16) | 77 | 99 |
| 2 | cyclohexene-CO₂Et (10) | diol-CO₂Et (17) | 83 | 99 |
| 3 | cycloheptene-CO₂Et (11) | diol-CO₂Et (18) | 85 | 99 |
| 4 | cyclooctene-CO₂Et (12) | diol-CO₂Et (19) | 81 | 99 |
| 5 | cyclohexenone (13) | hydroxy-diol ketone (20) | 86 | 99 |

TABLE 1-continued

Catalytic asymmetric oxidation of alkenes $$R\text{—CH=CH—}R' \xrightarrow[\text{O}_2 \text{ (30 psi)}, \text{H}_2\text{O}, 50°\text{ C., 3 days}]{0.5 \text{ mol \% Pd/Au (3:1)-2}} R\text{—CH(OH)—CH(OH)—}R'$$

| entry | substrate | product(s) | % yield(s) | % ee |
|---|---|---|---|---|
| 6 | 14 | 21 | 85 | 99 |
| 7 | 15 | 22 | 73 | 92 |

Conjugate cycloalkenes 9-12 gave 77-85% chemical yields and 99% ee of the syn-dihydroxylated products, (−)-16-(−)-19, respectively. The syn-stereochemistry of the products were confirmed independently by oxidizing 11 with $OsO_4$-NMO in t-BuOH—$H_2O$ to give (±)-18, whose $^1H$ NMR was identical to that of (−)-18. Compounds 9-12 were prepared from the corresponding cycloalkanones by the sequence: (i) carbonylation with NaH and diethyl carbonate; (ii) reduction with $NaBH_4$; and (iii) mesylation and elimination with methanesulfonyl chloride (MsCl) and 1,8-diazabicyclo[5.4.0]undec-7-ene (DBU). The absolute configuration of 16 and 17 were deduced by oxidation with IBX-DMSO to the corresponding (−)-(1S)-1-hydroxy-2-oxocycloalkanecarboxylic ethyl esters, whose specific rotations are similar to those reported (+)-(1R)-isomers but possessing opposite sign. The C1-absolute stereochemistry of (−)-18 was established by converting it to the known compound, 2S-2-hydroxy-2-methylcycloheptanone by the sequence: (i) reduction of the ester group with $LiAlH_4$ followed by mesylation with MsCl-$Et_3N$; and (ii) displacement of the resulting mesylate group with $LiAlH_4$ and then oxidation with IBX-DMSO. None of these alkenes (9-12) have been reported previously using Sharpless asymmetric dihydroxylation. Oxidation of 2-cyclohexenone (13) gave 86% yield and 99% ee of (−)-(2R,3R)-2,3-dihydroxycyclohexanone (20). Notably, asymmetric oxidation of 13 with Fe(II)(OTf)$_2$-chiral diamine ligand and $H_2O_2$ gave 21% yield and 46.4% ee of the syn-(2S,3S)-diol (+)-20. Non-conjugated 4-cycloocten-1-one (14) was also oxidized to give 21 and its absolute configuration is assumed based on the above oxidation. Terminal acyclic alkene 15 was oxidized to give (−)—(S)-22 in 73% yield and 96% ee. The (+)—(R)-22 has previously been obtained from an improved Sharpless oxidation in a 85% yield and 86% ee. Hence, Pd/Au-2-$O_2$ provided remarkable enantiomeric selectivity in the catalytic asymmetric dihydroxylation. Importantly, under 30 psi $O_2$, the rate of oxidation of alkenes is faster than that of the oxidation of syn-dials.

A mechanism has been proposed for the enantioselective oxidation of alkenes explaining the formation of syn-dihydroxylation, and a hypothetical complex I shows the chelation of Pd/Au-2-$O_2$ with the alkene. See, Scheme 2. A bidentate complex, involved two adjacent pyrrolidinone units (of the polymer), chelates with Pd/Au (3:1) NC, allowing the entry of $O_2$ and alkene. The smaller $R^S$ group of alkene orients toward the NC, while the larger $R^L$ away. The reactions likely take place at the corner or edge atoms of the NC surface. Using this bidentate model, stereochemistry from the oxidation of alkenes are shown in II-IV. Chelation of the C=O group of alkene substrates likely directs the facial selectivity in molecules 9-13.

Scheme 2.
Proposed models, stereochemistry of the oxidation of alkenes, cycloalkenes and mechanism of ring closure.

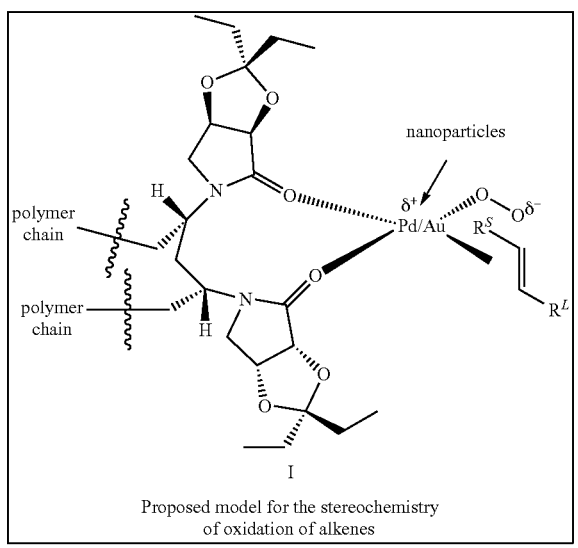

I

Proposed model for the stereochemistry of oxidation of alkenes

-continued

Stereochemistry of the oxidation of disubstituted and trisubstituted cycloalkenes and acyclic alkenes:

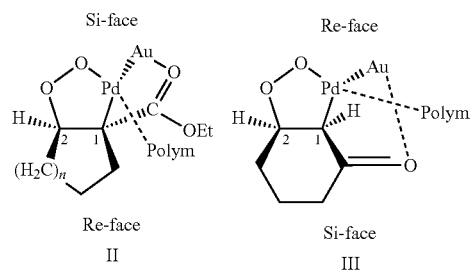

II, III, IV

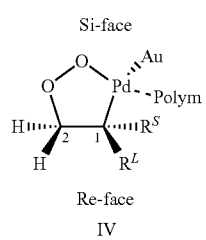

V

Proposed model for the stereochemistry of directed C—H oxidation of cycloalkanes Stereo- and regio-chemistry of the directed oxidation of cycloalkanes:

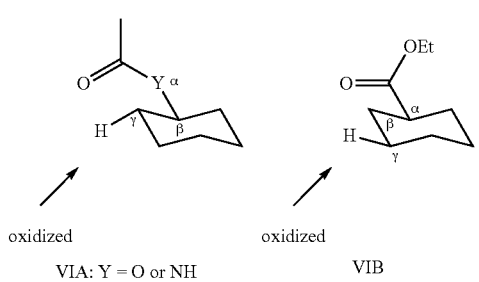

VIA: Y = O or NH; VIB

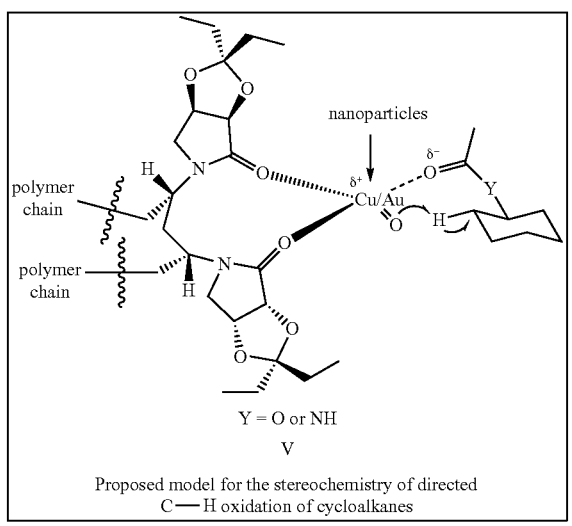

VII

Proposed model for the stereochemistry of directed ring closing reactions

Y = O or NH
$R^L$ = Ph, CO$_2$Et
$R^S$ = alkenyl

Proposed mechanism for the oxidative ring closing reactions:

VIII, IX, X, XI

Y = O or NH; $R^L$ = Ph, CO$_2$Et; $R^S$ = alkenyl; n = 0-3

Catalytic Regioselective and Asymmetric Oxidation of Cycloalkanes

It was previously discovered that in C—H oxidation with 1 mol % Cu/Au (3:1)—CSPVP, as described in WO 2017/172763, incorporated by reference herein in its entirety, chelation of the NCs and the tertiary-hydroxyl group directed asymmetric oxidation at γ-carbon (or C3) away from C—OH group of cycloalkanes. In most cases, C—H bonds were oxidized to C—OH, which subsequently oxidized to C=O, with the exception of (−)-sclareolide, where the resulting C2α-OH oxidized in a much slower rate due to steric effect. To study the aptitude of directing groups such as alcohols, esters, and amides, the catalytic regioselective C—H oxidation of functionalized molecules was studied. See, Table 2.

TABLE 2

Catalytic asymmetric oxidation of cycloalkanes.

Cyclic alkanes $\xrightarrow[\substack{30\% \text{ H}_2\text{O}_2,\text{ CH}_3\text{CN}, \\ 50^\circ \text{ C.}, 7 \text{ days}}]{\substack{0.5 \text{ mol }\% \\ \text{Cu/Au (3:1)-2}}}$ Chiral oxidized cyclic alkanes

| entry | substrate | product(s) | % yield[a] |
|---|---|---|---|
| 1 | 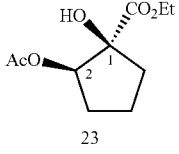 [SMILES: CCOC(=O)[C@]1(O)CCC[C@H]1OC(C)=O] 23 | 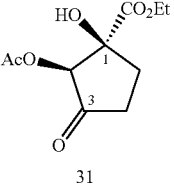 [SMILES: CCOC(=O)[C@]1(O)CCC(=O)[C@H]1OC(C)=O] 31 | 83 |
| 2 | 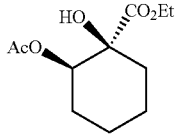 24 | 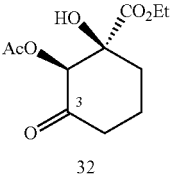 [SMILES: CCOC(=O)[C@]1(O)CCCC(=O)[C@H]1OC(C)=O] 32 | 83 |
| 3 | 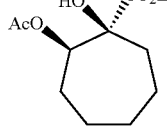 25 | 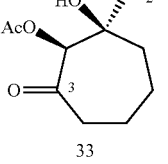 33 | 76 |
| 4 | 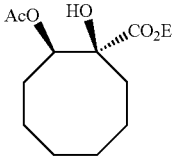 26 | 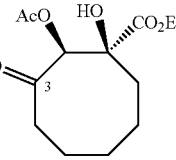 34 | 83 |
| 5 | 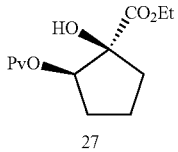 27 | 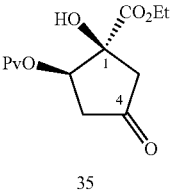 35 | NR |
| 6 | 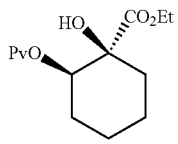 28 | 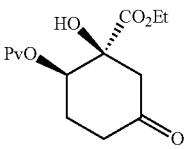 36 | 83 |

TABLE 2-continued

Catalytic asymmetric oxidation of cycloalkanes.

Cyclic alkanes →[0.5 mol % Cu/Au (3:1)-2, 30% H$_2$O$_2$, CH$_3$CN, 50° C., 7 days] Chiral oxidized cyclic alkanes

| entry | substrate | product | % yield[a] | % ee |
|---|---|---|---|---|
| 7 | 29 | 37 | 88 | |
| 8 | 30 | 38 | 88 | |
| 9 | 39 | 45 | 93 | 94 |
| 10 | 40 | 46 | 72 | 93 |
| 11 | 41 | 47 | 88 | 92 |
| 12 | 42 | 48 (meso) | 74 | — |

TABLE 2-continued

Catalytic asymmetric oxidation of cycloalkanes.

$$\text{Cyclic alkanes} \xrightarrow[\substack{30\% \text{ H}_2\text{O}_2,\ \text{CH}_3\text{CN},\\ 50°\text{ C.,\ 7 days}}]{0.5 \text{ mol }\% \text{ Cu/Au (3:1)-2}} \text{Chiral oxidized cyclic alkanes}$$

| | | | |
|---|---|---|---|
| 13[c)] | oxymetrine (43) | 49 | 60 — |
| 14[c)] | (−)-ambroxide (44) | 50: R = H<br>51: R = OH | 74<br>6 |
| 15 | 3-Pv-estrone (142) | 143 | 67 |

[a)] % yields are isolated yields.
[b)] Yield of 48 was based on recovered 42 (13% recovery); yield of 49 was based on recovered 43 (33% recovery).
[c)] at 80° C., 7 days.
NR: no reaction.

First, alcohols alcohols 16-19 (see, Table 1 were monoacetylated with acetic anhydride (Ac$_2$O) and pyridine to give 89-95% yields of 23-26, possessing acetoxy, OH, and ethyl ester groups. Oxidation of 23-26 with 5 mol % Cu/Au (3:1)-2 and H$_2$O$_2$ at 50° C. gave exclusively C3-oxo products 31-34 (76-83% yields), respectively. The oxidation took place at the γ-carbon away from C═O of acetoxy. Notably, molecules 23-30 are close to optically pure (>99% ee; see Table 1 for their precursor).

Next, mono-pivaloyl (PvO═Me$_3$CC═O) analogs 27-30 were prepared by the treatment of respective 16-19 with pivaloyl chloride and Et$_3$N in 85-88% yields. And, oxidation of 28-30 gave only 36-38, respectively, in 83-90% yields. Oxidation apparently took place at the γ'-carbon of the hydroxyl group, in which the bulky tert-butyl moiety blocks the chelation of C═O (of PvO) with NC, allowing the OH group to chelate and direct the oxidation. Compound 27 does not undergo oxidation reaction under the current conditions. The regiochemistry of 31-34 and 36-38 were revealed by their $^1$H and 2D COSY NAIR spectra. From these and following results, the aptitude of directive oxidation can be summarized as followed: CH$_3$CO$_2$≅CH$_3$CONH>OH>CO$_2$Et>cyclic ether.

A mechanism for the C—H oxidation reactions has been proposed, and a proposed complex V is illustrated in Scheme 2, showing the conformation of the oxidation of cycloalkanes. This functional-group directing effect provides a guidance for desymmetrized C—H oxidation. Hence, mono-functionalized cyclohexanes 39-41 were oxidized readily to give respective (−)—(S)-45, (−)—(S)-46, and (±)—(S)-47 in excellent chemical (88-94%) and optical (93-94% ee) yields (Table 2). The acetoxy, acetamide, and ester functions apparently directed the oxidation at the γ-carbon away from C═O group. The NMR spectra of (−)-45-(+)-47 were identical to those reported in the literature. The sign of specific rotation of (−)—(S)-45, {[α]$_D^{22}$=−80.4 (c 1.2, MeOH)} is opposite to that reported in the literature (+)—(R)-45. Compound (−)—(S)-46 was converted to 2-(S)-aminocyclohexanone by the treatment with 85% hydrazine at 70° C., and the sign of specific rotation, [α]$_D^{22}$=−71.3 (c 0.5, CHCl$_3$), is opposite to that reported in the literature for 2-(R)-aminocyclohexanone. Noteworthy, optical purities of 45 and 46 are greater than those reported in the literature. Absolute configuration of (+)—(S)-47, [α]$_D^{22}$=+19.3 (c 0.5, CHCl$_3$), was determined by conversion into (+)—(S)-3-oxocyclohexanecarboxylic acid (by LiOH-p-dioxane-H$_2$O), whose specific rotation is similar to that reported in the literature. The proposed stereochemistry for the directed oxidation are depicted in VIA and VIB (Scheme 2).

Other medium-sized molecules such as 42-44 and 142 were similarly oxidized regioselectively. N-Acetylamantadine (42) oxidized at the δ-carbon (away from C═O), affording 48 in 68% yield (based on recovered 13% of 42), whose $^1$H and $^{13}$C NMR data are identical to those reported in the literature. The oxidation took place at C3 (δ-carbon) of 42, which may due to ring strain of adamantane structure. Compound 48 along with its analogs showed anti-nociceptive effect by inhibition of TRPA1. Deacetyl derivative of 48 may be used for biological study. Oxymatrine (43), an inhibitor of cardiac ischemia and aldosterone-induced cardiac fibroblast proliferation, was oxidized regioselectively at C12 (using 20 mol % of the catalyst), the β-carbon away from C═O, to give 49 in 67% yield [based on recovered 43 (40% recovery)]. The $^{13}$C NMR data of 49 is identical to that reported in the literature. The carbonyl group in the six-membered ring appears to direct β-carbon oxidation. The regioselectivity here may due to the complexation of Cu/Au to C═O of the amide function of 43, thereby weakening the β-C—H bond (electronic effect). So far, no C—H oxidation of matrine or oxymetrine has been reported previously except enzymatic oxidation. Ambroxide (44) was oxidized to sclareolide (50) and 2S-2-hydroxysclareolide (51) in 83% and 7% yield (based on recovered 47% of 44), respectively. Oxygen of the tetrahydrofuran ring directed α-oxidation; resulting in lactone 50. Oxidation of 3-pivaloyl estrone (142) gave 12β-hydroxy 143 (67% yield). Surprisingly, oxidation of 142 with Cu/Au—PVP—H$_2$O$_2$ under similar reaction conditions did not produce 143 or C12-ketone, demonstrating the chiral effect of CSPVP.

Desymmetrized Ring-Closing Reaction

Based on the directing effect of the OH group, a desymmerized ring-closing reaction was discovered. See, Table 3.

TABLE 3

Catalytic oxidative desymmetrization-ring closure of alkenes.

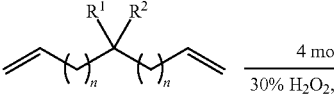

| entry | substrate | product | % yield$^{a)}$ | % ee |
|---|---|---|---|---|
| 1 | 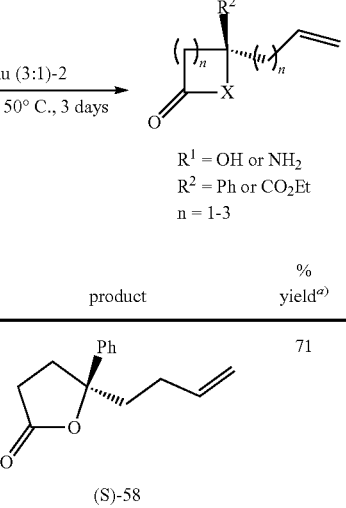 53 | 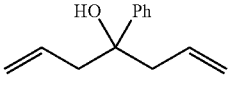 (S)-58 | 71 | 96 |
| 2 | 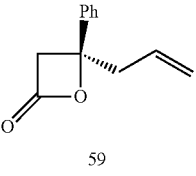 54 | 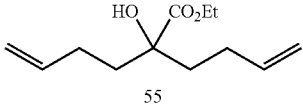 59 | 44 | 92 |
| 3 | 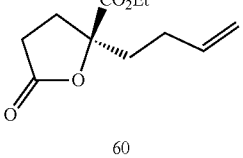 55 | 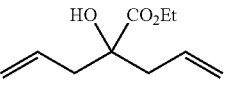 60 | 84 | 93 |
| 4 | 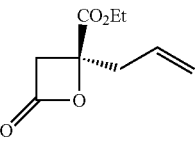 56 | 61 | 42 | 93 |

TABLE 3-continued

Catalytic oxidative desymmetrization-ring closure of alkenes.

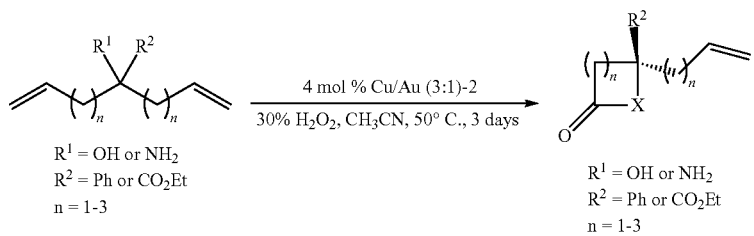

| entry | substrate | product | % yield[a] | % ee |
|---|---|---|---|---|
| 5 | 57 | 62 | 83 | 93 |
| 6 | 63 | 66 | 84 | 95 |
| 7 | 64 | 67 | 64 | 94 |
| 8 | 65 | 68 | 93 | 94 |

[a] % Yields are isolated yields.

For example, treatment of 53 with 4 mol % Cu/Au (3:1)-2 and 30% $H_2O_2$ in $CH_3CN$—$H_2O$ at 50° C. gave (−)—(S)-58 in 71% yield and 96% ee. Notably, using polymer 1 or NC comprising CSPVP as disclosed in WO 2017/172763 (also referred to herein as 1st-generation CSPVP) provided 95% or 90% ee, respectively, indicating 2 afforded the highest enantioselectivity among the three polymers. The absolute configuration of (S)-58 was determined by converting it to (−)—(S)-5-phenyl-5-propyl-dihydrofuran-2-one (58A), whose specific rotation is similar to that reported in the literature. The transformation of (S)-58 to (S)-58A involved: (i) ozonolysis with $O_3$—$CH_2Cl_2$ followed by reduction with $NaBH_4$; (ii) mesylation with $MsCl$-$Et_3N$; and (iii) removal of mesylate group with $NaBH_4$. See, Scheme 3.

Scheme 3.

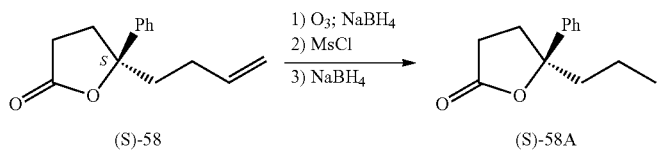

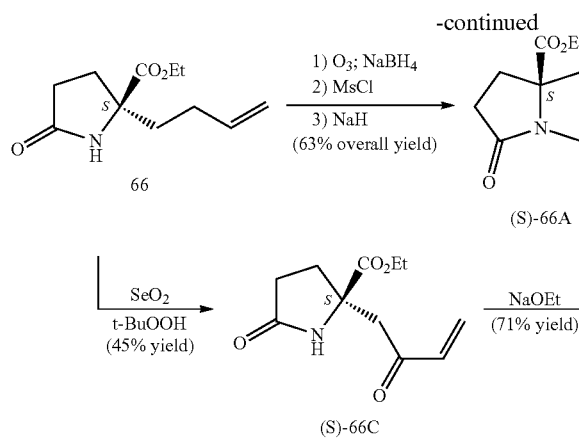
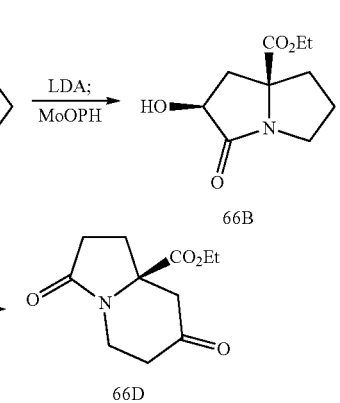

Other analogs such as 54-57 underwent similarly catalytic asymmetric oxidations to give lactones 59-62, respectively, in excellent optical yields (91-96% co). The four-membered ring lactones 59 and 61 gave lower chemical yields, which may due to a high energy needed for formation of the strained four-membered ring. The amino ester analogs, 63-65, also underwent catalytic asymmetric ring closure to give 66-68, respectively in good chemical (64-93%) and excellent optical (94-95% ee) yields (Table 3). A mechanism for the formation of lactones and lactams is proposed (Scheme 2), involving formation of copper ester VIII via complex VII, followed by addition to the terminal δ-alkene function (IX), fragmentation, and hydrolysis. The absolute configuration of (S)-66 was determined by conversion into pyrrolizidinone, 66B, by the sequence (see Scheme 3): (i) ozonolysis followed by reduction with NaBH$_4$—MeOH (75% yield); (ii) mesylation with MsCl-Et$_3$N (95% yield); (iii) ring closing with NaH (89% yield); and (iv) hydroxylation with LDA followed by MoOPH. The spectral data and specific rotation of 669 are identical to those reported. Also, 66 was converted to an indolizidinone, 66D. Allylic oxidation of 66 with SeO$_2$ and t-BuOOH in CH$_2$Cl$_2$ gave (S)-66C. (45% yield) along with 12% of the precursor alcohol of 66C. Compound 66C was cyclized with NaOEt (cat.) in toluene to give indolizidine 660 in 71% yield. These chiral pyrrolizidinone and indolizidinone molecules provide entries to various bioactive natural products (see Aim 2). Compounds 53-57 and 63-65 were prepared according to the reported methods.

In summary, second-generation CSPVPs, 1 and 2, containing a cyclic ketal were synthesized from D-isoascorbic acid. CSPVPs stabilize bimetallic Pd/Au or Cu/Au NCs and induce catalytic asymmetric oxidation of alkenes and alkanes. The enantioselective and regioselective oxidation of cyclohexane derivatives such as 23-26, 28-30 and 39-41, and desymmetrized ring closure of 53-57 and 63-65 are unprecedented, highlighting a great potential for the development of new synthetic methodologies. The opposite stereochemistry at C3, C4 of 2, or 105 (see Scheme 6; same as 2S) (see Scheme 1A), can be made from D-ribose. Various medium-sized molecules such as oxymetrine and amantadine were oxidized regioselectively by Cu/Au—CSPVP 2. Estrone pivalate ester 132 (or 142 in Table 2) was also oxidized to give exclusively C-11 ketoestrone 132A or 143 in Table 2) in good yield (see Table 2 and Scheme 7). Again; the cyclic keto function directs β—CH oxidation in agreement with the aforementioned results, see compound 49 (Table 2).

Embodiments of the present invention are useful in various catalytic asymmetric oxidation reactions that can be applied in the total synthesis of bioactive natural products and late-stage C—H oxidation of complex molecules. Included in these catalytic asymmetric oxidation reactions is the asymmetric oxidation of alkenes and alkanes for broader application. In addition to the reactions described above, further reactions, involving more challenging alkenes, are proposed. Scheme 4 provides examples of these further reactions.

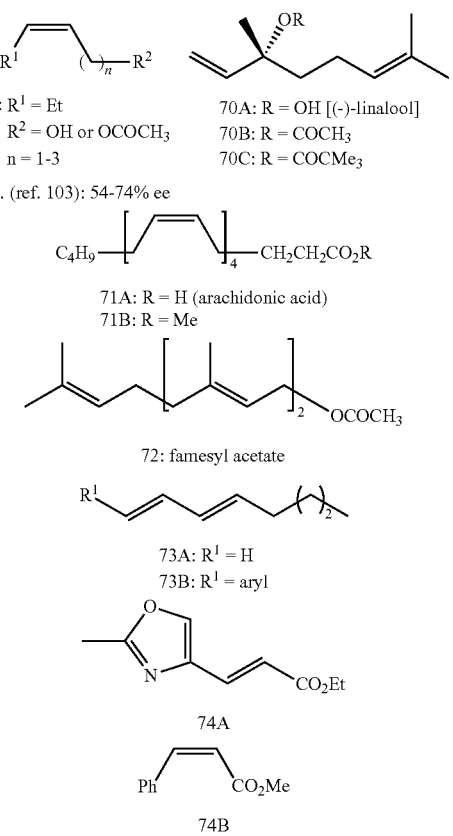

Scheme 4.
Catalytic asymmetric oxidation of alkenes with
0.5 mol % Pd/Au (3:1)-2 and O$_2$ (2 atm) at 50° C.

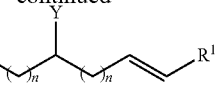

75A: $R^1$ = H; n = 1-3
Y = OH; OAc; $CO_2H$;
$CO_2Et$; NHAc

75B: $R^1$ = $CH_3$
Y = OH; OAc; $CO_2H$;
$CO_2Et$; NHAc

Predicted or assumed products:

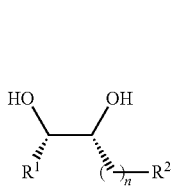

76: $R^1$ = Et
$R^2$ = OH or $OCOCH_3$
n = 1-3

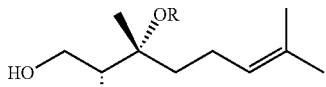

77A: R = OH
77B: R = $COCH_3$

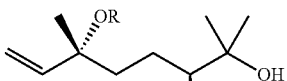

77C: R = $COCMe_3$

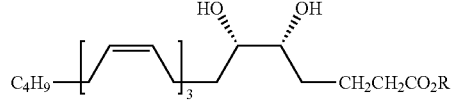

78A: R = H
78B: R = Me

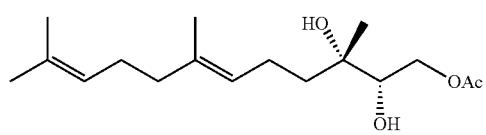

79

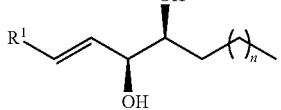

80A: $R^1$ = H
80B: $R^1$ = aryl

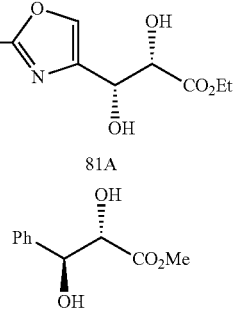

81A

81B

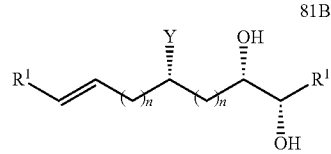

82A: $R^1$ = H; n = 1-3
Y = OH; OAc; $CO_2H$;
$CO_2Et$; NHAc

82B: $R^1$ = $CH_3$
Y = OH; OAc; $CO_2H$;
$CO_2Et$; NHAc

For example, cis-allylic and homoallylic alcohols (69) did not provide high ee's (54-74% ee) in the SAD reactions. Likewise, an 87% ee of the diol was reported from SAD of cis-cinnamic acid methyl ester (74B). Following the proposed chelation control via metallo-1,2-dioxolanes (II-IV; Scheme 2), $\eta^2$-peroxido $Pd^{II}$ intermediate would approach alkenes 69-74 from the Si-face, resulting 76-81, respectively. The hydroxyl or acetoxy, group on $R^2$ of cis-alkenes 69 should complex with Pd/Au, leading to 76. Similarly, hydroxyl or acetoxy-directed oxidation of 70A and 70B should give 77A and 77B. On the other hand, the bulky pivaloate group of 70C would block the chelation, resulting in the oxidation of the more substituted alkene to give 77C. From the study of (+)-limonene, it was discovered that after one alkene function was oxidized, the remaining second alkenyl group of the same molecule did not react. Likely, the resulting diol function complexes with the NCs, decreasing the rate of oxidation of the second alkenyl group in the same molecule. There are four similar double bonds in arachidonic acid (71A). We hypothesize that the directing effect of carboxylic acid in 71A or ester in 71B will lead to oxidation of the δ-alkenyl group. Similarly, 72 will give 79. Conjugate diene 73A and 73B will test out the regioselectivity and enantioselectivity of Pd/Au-2-$O_2$ system. It is assumed that the internal C═C of 73A is more reactive than the terminal C═C to give 80A, and the bulky, aryl group in 73B will retard the oxidation of C═C adjacent to aryl group, resulting in 80B. It is assumed that the ester group in oxazoles 74A has a greater directing effect than the oxazole ring, leading to diol 81A, cis-Cinnamic ester 74B will show whether our system provide a greater ee than that from SAD. Mimicking the desymmetrized oxidation with Cu/Au-2-$H_2O_2$ (see Table 3), it is questioned whether the functional groups Y in 75 can direct the desymmetrized oxidation by Pd/Au-2-$O_2$. Such asymmetric desymmetrization has not been reported in SAD or other enantioselective di hydroxylation. Compounds 70A, 70B, 71A, 72, 73, and 74B are commercially available materials. Compound 74A can be prepared from the Horner-Wadsworth-Emmons (HWE) olefination of 2-methyloxazole-4-carboxaldehyde and $(EtO)_2POCH_2CO_2Et$. Preparations of 75 will be similar to those of 53-57 by starting with 2 equiv. of the required Grignard reagents (such as 3-butenylmagnesium bromide) and 1 equiv. of ethyl formate. For the preparation of 75 where Y═NHAc, the aforementioned alcohol 75A (Y═OH) will be oxidized to ketone followed by reductive amination with $NH_4OAc$ and $NaCNBH_3$, and then acetylation with $Ac_2O$. For the preparation 75 where Y═$CO_2Et$, ethyl acetate will be dialkylated with 2 equiv. each of LDA and the alkenyl bromides.

Based on the results shown in Tables 2 and 3, it is proposed to modify the geminal R groups of 2, which may enhance the enantioseiectivity oxidation of unactivated C—H bond (with % ee >99 being the goal). It is believed that the bulkier the R group in 2, the greater the optical yields. Hence, trans-ketalization of 5 with diisopropyl ketone or dicyclohexyl ketone (both are available from Sigma-Aldrich Inc.) will give 83A or 83B, respectively (see, Scheme 5; see, Scheme 1 for trans-ketalization reaction). Polymerization to of 83A or 83B with respective 1% 85A or 85B and AIBN furnishes CSPVP 86A or 86B. Copolymer 85A or 85B is made from respective 83A or 83B with an equivalent of vinyl acetate and catalytic amount of AIBN.

Scheme 5. C—H oxidation of alkanes and cycloalkanes using 5 mol % Cu/Au (3:1)-CSPVPs (2 or 86) and 30% $H_2O_2$.
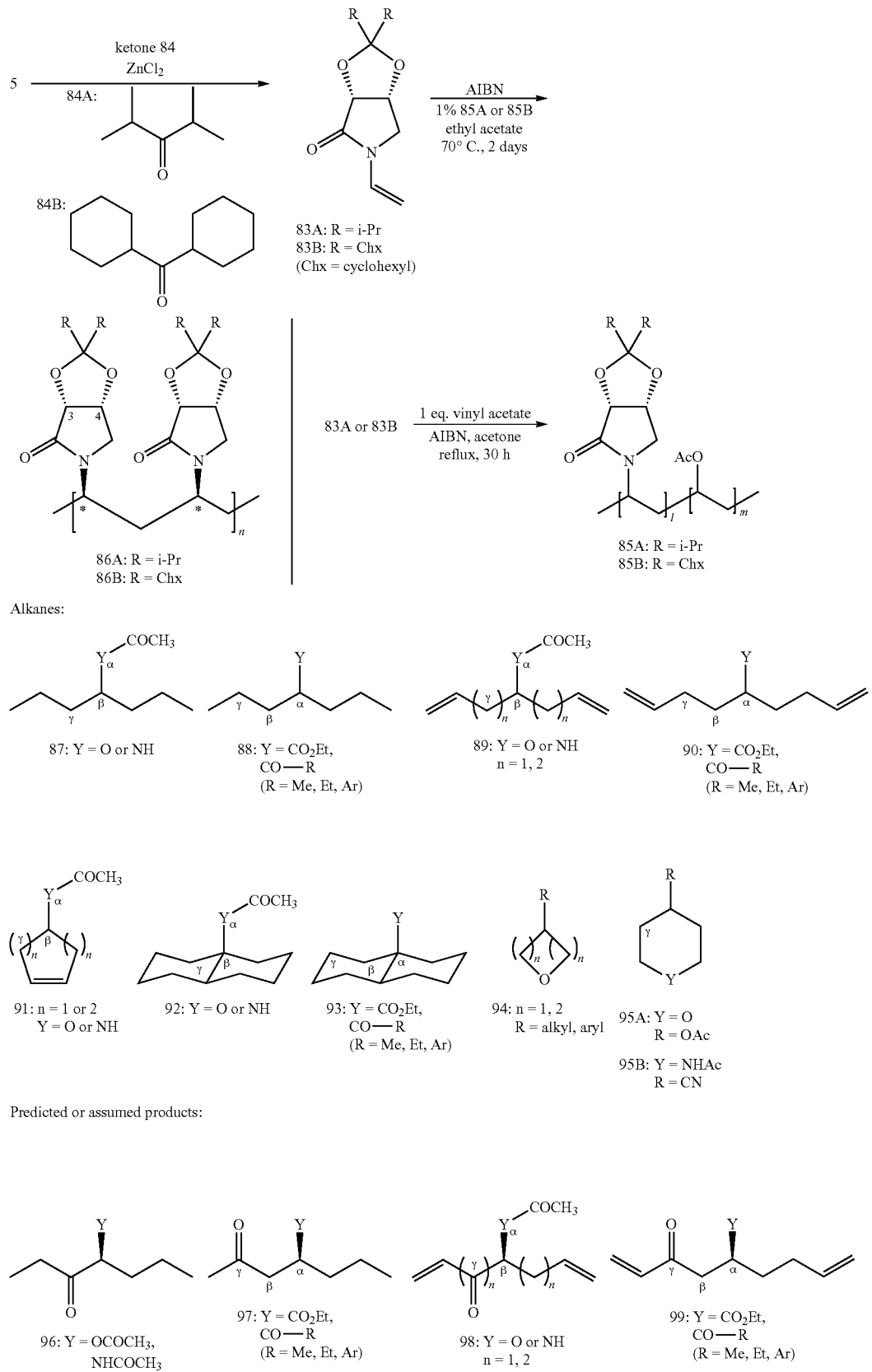

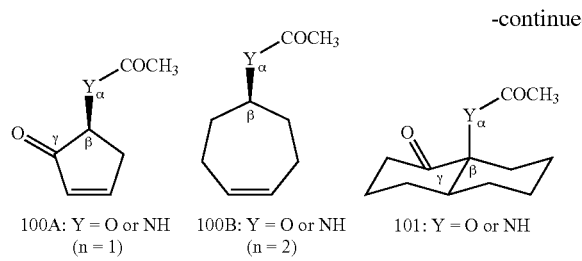
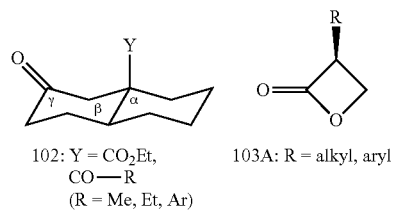

100A: Y = O or NH (n = 1)  100B: Y = O or NH (n = 2)  101: Y = O or NH  102: Y = CO$_2$Et, CO—R (R = Me, Et, Ar)  103A: R = alkyl, aryl

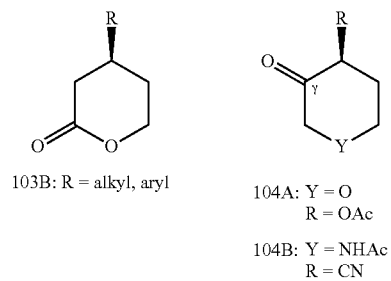

103B: R = alkyl, aryl

104A: Y = O
R = OAc

104B: Y = NHAc
R = CN

In investigating how various alkanes and cycloalkanes will provide predictive information on the regio- and stereochemistry induced by the directing groups, 87-95 (Scheme 5) are selected using 5 mol % Cu/Au (3:1)-2 (or 86)-30% H$_2$O$_2$ at 50° C. Based on results described in Tables 2 and 3, it is believed that the functional groups directed the oxidations via model V (Scheme 2), leading to (S)-configuration (see 45-47) in the oxo-products. The directive aptitude is: OCOCH$_3$≅NHCOCH$_3$>OH>CO$_2$Et>cyclic ether. Chiral products 96-104 are predicted to be formed, and the absolute configurations are presumed based on results described above. As described in Scheme 2, the γ-carbon away from the carbonyl of 87 and 88 is oxidized, resulting in 96 and 97, respectively. Next, the reported C—H oxidation of 1-isopropenyl-cyclohexanol to (R)-hydroxy-3-(isopropenyl)cyclohexanone (98% yield; 93% ee) suggests the alkene function is not oxidized and the tert-OH group directed γ-oxidation. Hence, the acetoxy, acetamide, and ester functions of 89-91 should direct the C—H oxidation to give 98-100, respectively (the C═C does not direct C—H oxidation). In the absence of tert-OH or NH$_2$ group, no lactone or lactam should form. The additional C═C will allow further functional group manipulation. Molecules 87-90 are either commercially available materials or can be prepared using similar methodologies as those of 53 and 63. Compound 91, n=1, is available from Sigma-Aldrich Inc., and the preparation of 91, n=2, has been reported in the literature. The preparations of irons-decalins 92 and 93 have been reported in the literature, and the C—H oxidation will provide useful chiral building blocks such as 101, whose hydroxyl intermediate (after removal of the acetyl group with K$_2$CO$_3$-MeOH) has been used in the study of total synthesis of laurenene. From the finding of regioselective C—H oxidation of (−)-amboxide (44) to (−)-sclareolide (50) (see Table 2), the cyclic ether oxygen apparently directed the α-carbon oxidation, leading to a lactone. Hence, oxidation of cyclic ethers 94 is proposed, which will produce lactones 103. Since acetoxy function has a greater chelation effect to Cu/Au than cyclic ether, oxidation of 95A should give 104A, and 95B (commercially available) to 104B. Arachidonic acid (71A) or its methyl ester 71B is also subjected to the oxidation reactions. The C4-oxo derivatives of 71 may form, which would demonstrate the directing effect of carboxyl group over alkenes (double allylic C—H). It is believed that these studies may reveal a rapid generation of highly functionalized chiral molecules and their possible application in synthesis of bioactive molecules.

In certain embodiments of the present invention, the catalytic asymmetric oxidation reactions achieved with the NCs comprising the bimetallic catalyst and CSPVP molecules can be utilized as platforms for achieving synthesis of bioactive natural products, such as (+)-goniodiol, (−)-penibruguieramine A, (−)-omuralide, and (+)-euphorikanin A. See, Scheme 6.

Scheme 6. Application in the total syntheses of bioactive natural products.

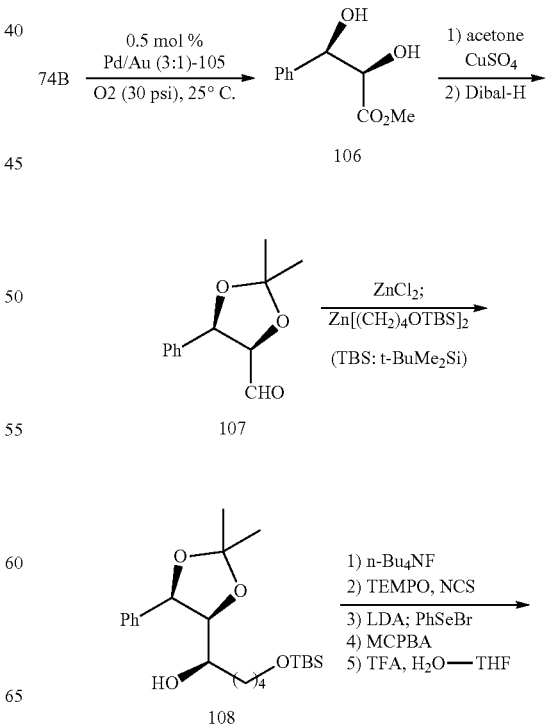

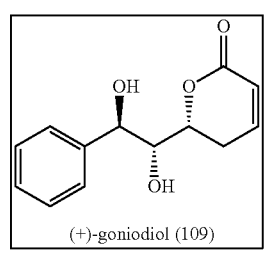
(+)-goniodiol (109)
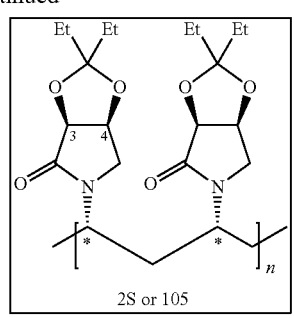
2S or 105
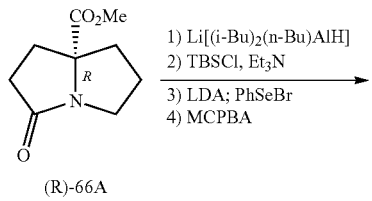
(R)-66A
1) Li[(i-Bu)₂(n-Bu)AlH]
2) TBSCl, Et₃N
3) LDA; PhSeBr
4) MCPBA
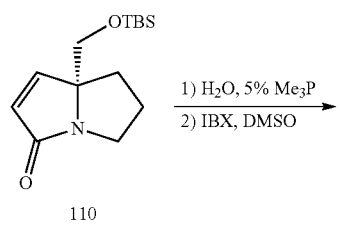
110
1) H₂O, 5% Me₃P
2) IBX, DMSO
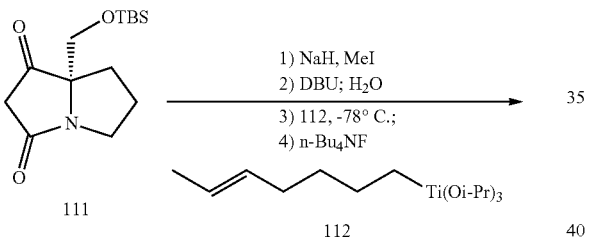
111        112
1) NaH, MeI
2) DBU; H₂O
3) 112, −78° C.;
4) n-Bu₄NF
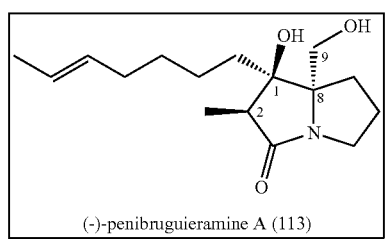
(−)-penibruguieramine A (113)
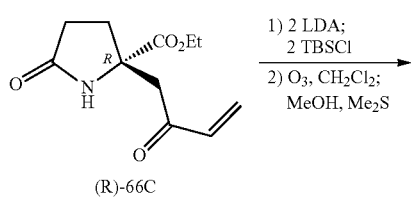
(R)-66C
1) 2 LDA;
2 TBSCl
2) O₃, CH₂Cl₂;
MeOH, Me₂S
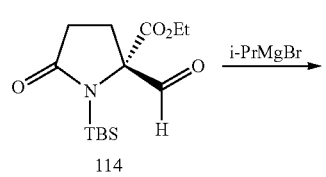
114
i-PrMgBr
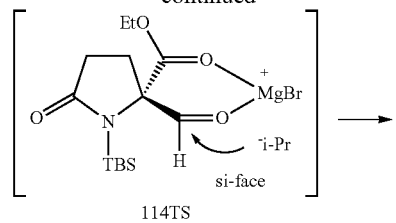
114TS
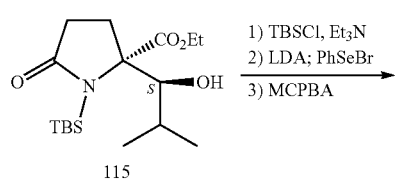
115
1) TBSCl, Et₃N
2) LDA; PhSeBr
3) MCPBA
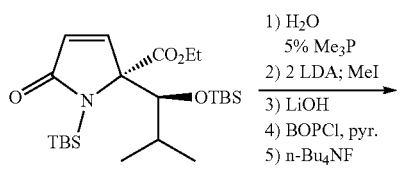
116
1) H₂O
5% Me₃P
2) 2 LDA; MeI
3) LiOH
4) BOPCl, pyr.
5) n-Bu₄NF
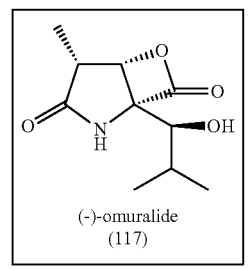
(−)-omuralide (117)
37
1) HO(CH₂)₂OH
2) K₂CO₃, EtOH
3) IBX, DMSO
4) 2 eq LDA, MeI
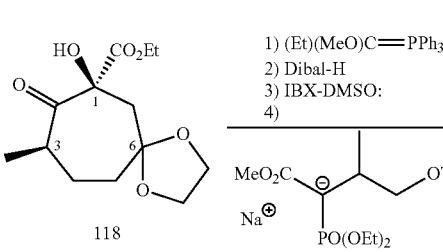
118        (119)
1) (Et)(MeO)C=PPh₃
2) Dibal-H
3) IBX-DMSO:
4)
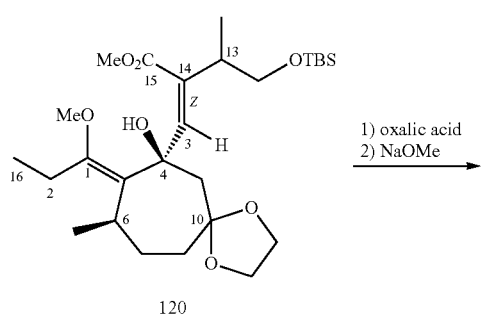
120
1) oxalic acid
2) NaOMe

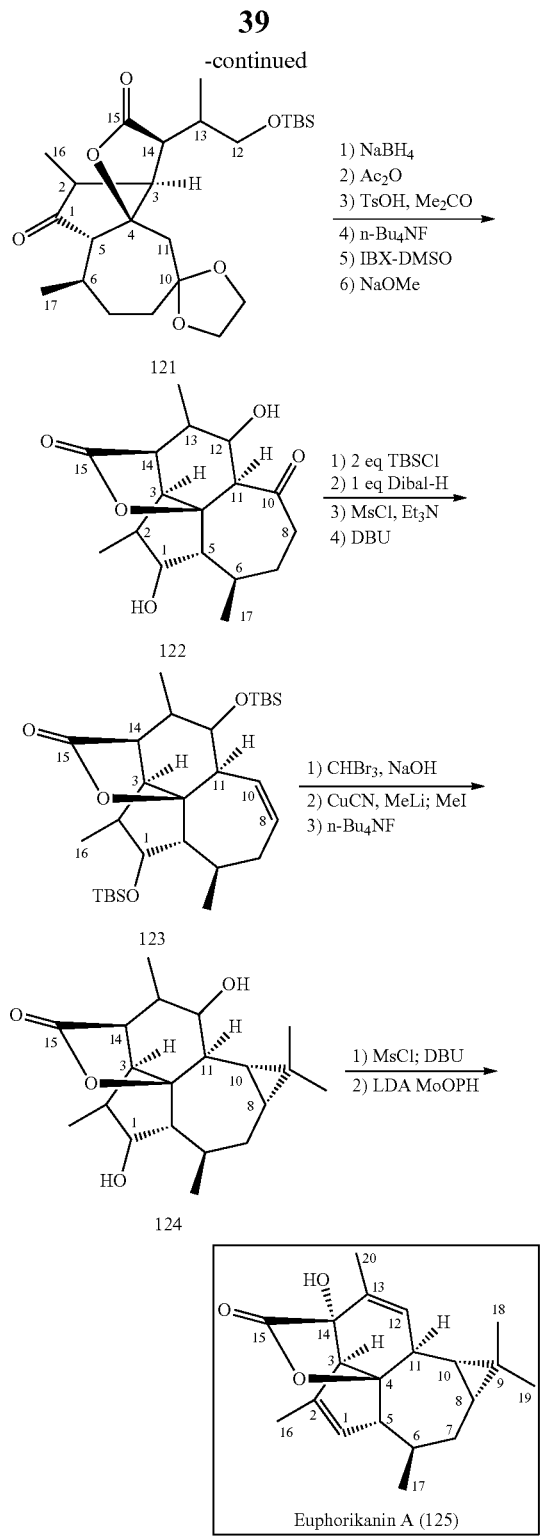

Dibal-H to give aldehyde 107. See, Scheme 6. Compound 105 has been synthesized from (2S,3S)-4-amino-4-deoxy-2,3-O-isopropylidene-D-erythronolactam (4S; the enantiomer of 4), which was made from D-ribose, via a sequence of reactions described in Scheme 1A. Addition reaction of 107 with $ZnCl_2$ followed by $Zn[(CH_2)_4OTBS]_2$ via chelation control gives 108 selectively. (+)-Goniodiol (109) is obtained from 108 by the sequence: (i) removal of the TBS protecting group with n-$Bu_4NF$; (ii) selective oxidation of the primary hydroxyl (in the presence of the secondary OH) with NCS and TEMPO (0.1 mol equiv); (iii) α-selenylation of the lactone function with LDA followed by PhSeBr; (iv) β-elimination of the selenide with MCPBA; and (v) removal of the acetonide with trifluoroacetic acid in $H_2O$ and THF. In the selective oxidation of the primary OH group with NCS TEMPO, the resulting aldehyde forms a six-membered ring lactol, which subsequently oxidizes to the lactone.

(−)-Penibruguieramine A (113) is a pyrrolizidine alkaloid isolated from mangrove *Bruguiera gymmorrhiza*, whose total synthesis has been reported in the literature. Molecule 113 possesses strong antibacterial activity against *Staphylococcus aureus* with a MIC value of 6.4 μg/mL. Pyrrolizidine (R)-66A is used to synthesize 113. Compound (R)-66A is prepared as described in Table 3 and Scheme 3 but using CSPVP 105 (or 2S) in the catalytic cyclization of 63. Selective reduction of the ester moiety of (R)-66A with $Li[(i-Bu)_2(n-Bu)AlH]$ followed by protection of the resulting primary hydroxyl group with $TBSCl-Et_3N$ and α-selenylation of the amide group with LDA-PhSeBr and β-elimination with MCPBA gives 110. Conjugate addition reaction of 110 with $H_2O$-5% $Me_3P$, and oxidation of the hydroxyl group with IBX-DMSO provides ketone 111. Conversion of 111 to (−)-113 is carried out by the sequence: (i) methylation with 1.2 equiv of NaH and 1 equiv of MeI; (ii) isomerization of α-CH of the dicarbonyl with DBU in THF—$H_2O$ (9:1); (iii) addition by 1 equiv of trans-5-heptenyltitanium triisopropoxide (112) in THF at −78° C.; and (iv) removal of the silyl group with n-$Bu_4NF$ in THF. In the methylation reaction, the enolate ion attacks MeI from the convex face, hence to obtain the β-oriented methyl, DBU-THF—$H_2O$ is used to isomerize the α-CH (C2) of the β-ketoamide. Organotitanium 112, which obtains from E-7-bromo-2-heptene, approaches the ketone from the convex face of the pyrrolizidinone ring, leading to the desired C1-stereochemistry.

The specific inhibition of proteasome 20S by (−)-omuralide (117) has led to numerous total syntheses and investigation on its anticancer activity. (−)-Omuralide or clastolactacystin β-lactone was derived from the hydrolysis of lactacystin. According to an embodiment of the present invention synthesis of 117 is from (R)-66C, which is synthesized as that of (S)-66C (Scheme 3) but using 4 mol % Cu/Au (3:1)-105 and $H_2O_2$ followed by allylic oxidation. Treatment of (R)-66C with 2 equiv of LDA in THF at −78° C. followed by 2 equiv of TBSCl and ozonolysis of the diene function with $O_3$-MeOH-$Me_2S$ gives aldehyde 114. Chelation-controlled addition of i-PrMgBr gives selectively 115. i-PrMgBr complexes with the 1,3-dicarbonyl functions allowing isopropyl anion to attach the aldehyde from Si-face of aldehyde (opposite face to the bulky TBS group). Silylation of 115 with $TBSCl-Et_3N$ followed by selenylation with LDA-PhSeBr and oxidation with 1 equiv MCPBA affords enamide 116, which is converted to (−)-omuralide (117) by the sequence of reactions: (i) addition with $H_2O$-5% $Me_3P$; (ii) lithiation with 2 equiv of LDA (deprotonation of OH and α-CH of amide group) at −78° C. (to ensure no β-elimination of the alkoxide anion) followed by 1 equiv of MeI at −78° C.; (iii) hydrolysis of the ester function with (+)-Goniodiol (109) is a styryllactone, isolated from *Goniothalamus sesquipedalis* and has shown to possess strong anticancer activities including lung carcinoma, leukemia, human melanoma, and CNS carcinoma. A number of styryllactones such as leiocarpin C, parvistone D and E, and total synthesis of 109 have been reported in the literature. The synthesis of 109 starts from the oxidation of 74B (Scheme 4) with 0.5 mol % Pd/Au-105 and $O_2$, and resulting diol 106 is protected with acetone-$CuSO_4$ and reduced with LiOH in THF—H$_2$O (9:1) and lactonization with bis-(2-oxo-3-oxazolidinyl)-phosphinic chloride (BOPCl) and pyridine; and (iv) removal of the TBS group with n-Bu$_4$NF in THF.

(+)-Euphorikanin A (125), a diterpene, isolated from the roots of perennial herb *Euphorbia kansui*. The roots are used for the treatment of ascites, asthma, edema, epilepsy, and soreness. It contains a unique 5/6/7/3 fused ring system and has not been synthesized previously. A total synthesis of 125 from 37 (Table 2), containing the needed stereochemistry and functional groups, is outlined in Scheme 6. Ketallization of 37 with ethylene glycol and pyridinium tosylate (a catalytic amount) followed by removal of the pivaloyl group, oxidation with IBX-DMSO, and α-methylation with 2 equiv LDA-MeI leads to 118. Methyl iodide reacts with the enolate ion from the opposite face of the C1 bulky ester group, and the C3-α-isomer, if formed, is isomerized with a catalytic amount of NaOEt in EtOH. Wittig olefination of 118 with glide (Et)(MeO)C=PPh$_3$ followed by reduction and oxidation (of the C1-ester to carboxaldehyde), and Horner-Wadsworth-Emmons reaction with anion 119 gives 120. α-Substituted phosphonate anion with sterically encumbered aldehydes provided the Z-unsaturated esters (C3, 14). Phosphonate 119 is derived from the bromination of methyl 4-(t-butyldimethylsilyloxy)-3-methylbutanoate followed by triethylphosphite and NaH. The stereochemistry at C3 may dictate the stereochemistry in the subsequent intramolecular 1,4-addition reaction. Hydrolysis of the C1-vinyl ether function of 120 with 0.1 M aqueous oxalic acid, and ring closing with NaOMe gives 121. The 1,4-addition of enolate (C2) to alkene C3 takes place from the Re-face (C14) of the ene ester, since both ester C=O and the enolate oxygen chelate with the Na$^+$, which in turn directing the (S)-stereochemistry at C3. The ketal is stable under oxalic acid condition. Compound 121 is converted to 122 by the sequence: (1) reduction of C1-keto with NaBH$_4$; (2) acetylation with Ac$_2$O-pyridine; (3) removal of the ketal with TsOH-acetone at 25° C.; (4) desilylation with n-Bu$_4$NF; (5) oxidation with IBX-DMSO; and (6) intramolecular aldol reaction with NaOMe-MeOH. C-11H is epimerizable and C11-α-H isomer 122 is used. Protection of the two hydroxyl functions of 122 with 2 eq. TBSCl-Et$_3$N followed by reduction of C10-keto with Dibal-H, mesylation with MsCl-Et$_3$N, and β-elimination with DBU gives 123. Cyclopropanation of C8 alkene of 123 with CHBr$_3$—NaOH followed by Me$_2$CuLi then MeI, and removal of TBS groups affords 124. The dibromocarbene adds to the alkene from the less hindered α-face. Mesylation of diol 124 with 2 eq. of MsCl-Et$_3$N followed by β-elimination with DBU, and α-hydroxylation (α-face is more accessible than β-face) of the lactone with LDA-MoOPH or lithium HMDS-t-BuOOH-pyridine-CuI furnishes euphorikanin A (125). If the stereochemistry at C3 of 121 is R-configuration, the reaction will cyclize the E-alkene (C3=C14) of 120, which can be prepared from the phosphorane Ph$_3$P=C(CHMeCH$_2$OTBS) with the aldehyde (derived from 118) (Scheme 6). The foregoing describes representative total syntheses of four bioactive natural products. It is understood that further modification of the synthesized natural products and syntheses of other bioactive molecules can be achieved utilizing the general enantioselective oxidation of alkenes and alkanes reactions also discussed above.

The selectivity and predictability in aliphatic C—H oxidation of complex molecules is discussed below. Natural products (NP) remain the major sources in drug discovery and development process. Over the course of 33 years (from 1981-2014), there were 67 approved drugs (6%) from unaltered NP, 320 (26%) from NP derivatives, 172 (14%) from synthetic/mimic of NP, and 162 (13%) from synthetic NP pharmacophore/mimic of NP. Hence, a total of 59% of the drugs derived from NP sources. The "late-stage" aliphatic C—H oxidation, C—H azidation, and C—H chlorination of complex molecules are the highlights of synthetic organic chemistry in recent days. The newly installed ketone (or hydroxyl) group can be converted into various functionalities, diversifying the natural product molecular library for screening of bioactivity. Addition of hydroxyl, carbonyl, amine (from a reduction amination of the ketone function with NH$_4$OAc—NaCNBH$_3$), amide, and sulfide to the bioactive natural products may enhance their pharmacology such as pharmacokinetics (PK) and bioactivities. Most of the reported oxidation, amination, azidation, and chlorination often take place at the tertiary C—H, allylic C—H, or benzylic C—H bond due to a lower bond dissociation energy comparing with that of unactivated CH$_2$ and CH$_3$ bonds. As described in Table 2, (−)-ambroxide (44) was oxidized to (+)-sclareolide (50), which oxidized regioselectively at the rigid and less hindered C2-CH$_2$ to give 2S-hydroxy 51. Hence, the present invention complements the repotted procedures.

The "late-stage" C—H oxidation of fifteen representative bioactive natural products and drugs, 126-140 are shown in Scheme 7.

Scheme 7.
Late-stage C—H oxidation of bioactive complex molecules using catalytic amount of Cu/Au (3:1)-2 and H$_2$O$_2$. CSPVP 105 will be used for oxidation of 136 and 140 instead of 2.

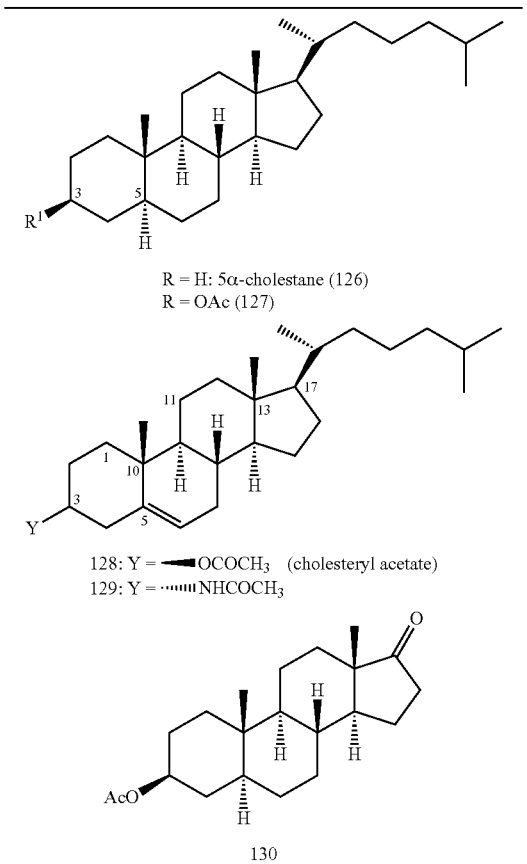

R = H: 5α-cholestane (126)
R = OAc (127)

128: Y = ⬛OCOCH$_3$ (cholesteryl acetate)
129: Y = ⋯NHCOCH$_3$

130

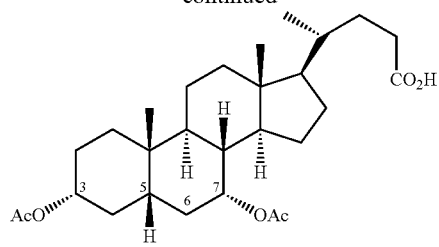
chenodeoxycholic acid diacetate
(131)
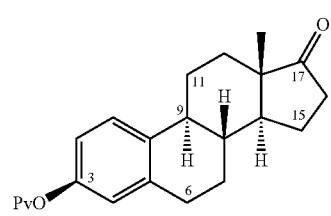
estrone pivalate (132)
Pv = t-BuCO
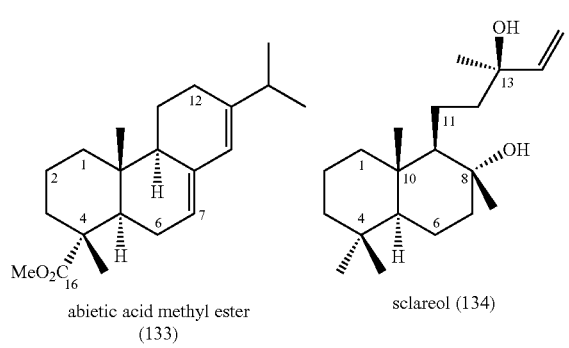
abietic acid methyl ester
(133)
sclareol (134)
Predicted oxidation products:
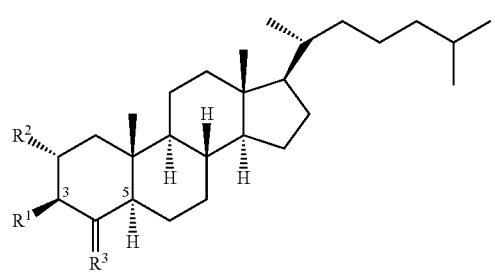
126A: $R^1$ = H; $R^2$ = OH; $R^3$ = $H_2$
127A: $R^1$ = OAc; $R^2$ = H; $R^3$ = O
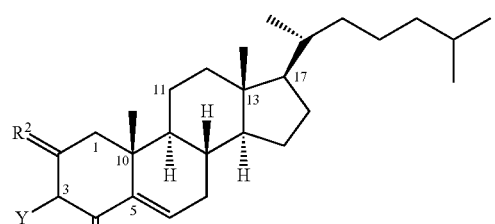
128A: Y = —OCOCH$_3$; $R^1$ = O; $R^2$ = $H_2$
129A: Y = ·····NHCOCH$_3$; $R^1$ = $H_2$; $R^2$ = O
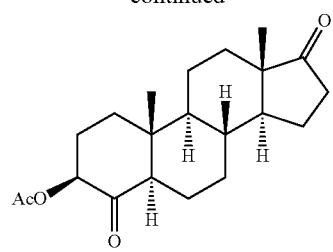
130A
1) $K_2CO_3$
2) IBX
   DMSO
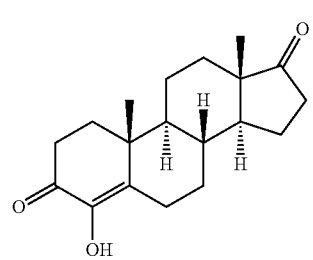
Formestane (130B)
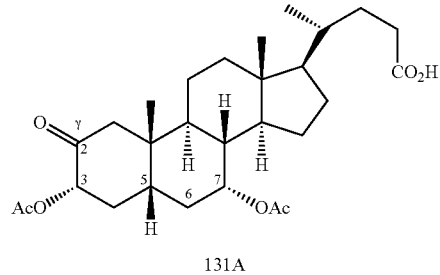
131A
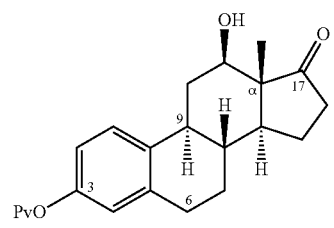
132A: Pv = t-BuCO
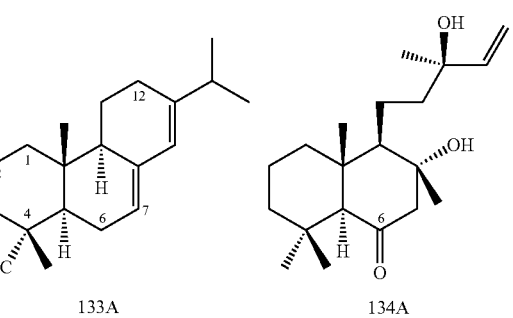
133A                    134A -continued
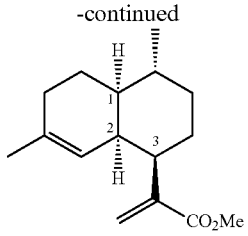
arternisinic acid
methyl ester (135)
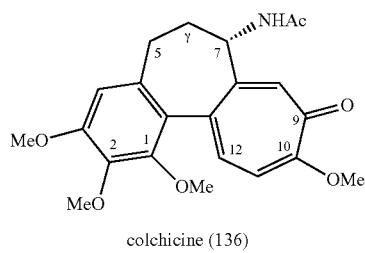
colchicine (136)
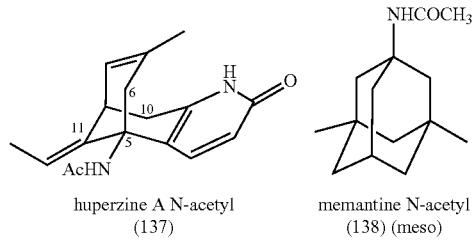
huperzine A N-acetyl (137)   memantine N-acetyl (138) (meso)
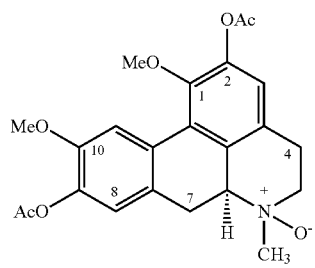
boldine N-oxide diacetate (139)
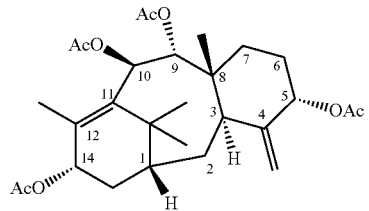
taxusin (140)
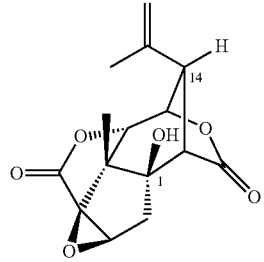
picrotoxinin (141)
-continued
Predicted oxidation products:
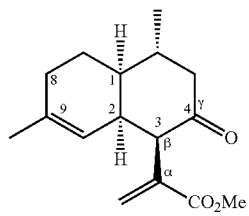
135A
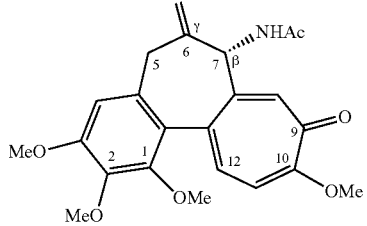
136A
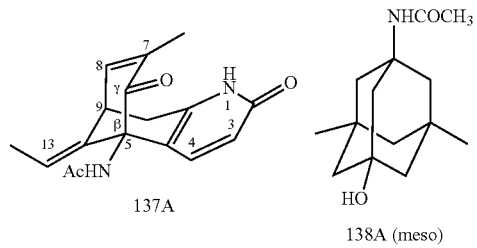
137A   138A (meso)
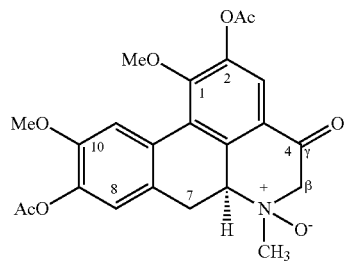
139A
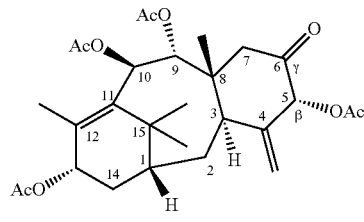
140A
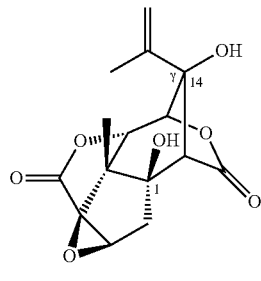
141A These molecules or their hydroxyl or amine precursors are available commercially. Hence, molecules 126-128, 131 (from diacetylation of chenodeoxycholic acid), 132 (from pivalation of estrone with pivoloyl chloride (i-BuCOCl) and pyridine), 133 (from methylation of abietic acid), 134, 136, and 139 (from diacetylation followed by oxidation of tert-amine of boldine) are from Sigma-Aldrich (Milwaukee, WI), 130 (from acetylation of 3-hydroxy-androstan-17-one) and 135 from AK Scientific (Union City, CA), 137 (from acetylation of huperzine A) and 140 from 1717 CheMall Co. (Mundelein, IL), and 138 from Fisher Scientific (Chicago, IL). Compound 129 is made from cholesterol by the sequence: (i) mesylation with MsCl-Et$_3$N; (ii) S$_N$2 displacement with NaN$_3$ in DMF; (iii) reduction of azide to amine with NaBH$_4$, and (iv) acetylation with Ac$_2$O. Since these compounds, except 138, are enantiopure, PVP and 2 are used separately in the Cu/Au (3:1)/CSPVP—H$_2$O$_2$ oxidation reactions. Notably, CH$_3$CN is used as a co-solvent to dissolve the complex molecules. The products' regiochemistry is determined by single-crystal X-ray analyses if possible, or 2D COSY, NOSY, HMQC, and HMBC NMR spectroscopy (on a 600 MHz NMR instrument), or comparison with the NAIR spectra of literature reported molecules. The predictive oxidation sites (at γ-carbon of the carbonyl function) are shown in VIA and VIB (Scheme 2), and the oxidized products are listed in Scheme 7, 5α-Cholestane (126), like sclareolide, oxidizes at C2 to give 126A. The directing-group effects onto the regiochemistry are tested first by compounds 127-131, where C3-β-acetoxy group directs the oxidation at C4 (due to C3-S-stereochemistry), and C3-α-acetamido group of 129 directs at C2 to give 129A (see, Table 2). Product 130A is converted to formestane (130B), a steroidal aromatase inhibitor and anti-breast cancer drug, by basic hydrolysis of the C3-acetoxy group followed by oxidation with IBX in DMSO. Despite the availability of various synthetic analogs of formestane, specific aromatase inhibitors with lower side effects are needed. Chenodeoxycholic acid (precursor of 131; CDCA) is a bile acid produced by the liver and used for the treatment of gallstone and possibly osteoarthritis. It is believed that the C3-α-acetoxy group directs oxidation at C2, 131A (C6 is shielded by C5, C7 α-Hs), which allows synthesis of various analogs of CDCA. Eestrone (the C3-OH derivative of 132) is an estrogenic hormone and its C16-oxime derivatives have been shown to possess anti-cervix and anti-breast carcinoma activities. To demonstrate the feasibility of the oxidation, estrone pivalate ester 132 was treated with Cu/Au-2 and obtained 68% yield (based on 15% of recovery of 132) of C-12β-hydroxy estrone 132A. Apparently, the C17-carbonyl function of 132 directed the oxidation at C-12, leading to 132A. The derivatives of abietic acid (133), a diterpene resin acid, show antiallergic and anticonvulsant activities. The carboxyl function directs the oxidation at C2 (see 41 to 47, Table 2), providing 133A. Sclareol (134), obtained from clary sage (*Salvia sclarea*), is used as a fragrance and has been shown to possess inhibitory activity against human HCT116 colon cancer cells through induction of apoptosis. The oxidative site is believed to be at C6 (γ to the C—OH carbon) of the ring system, and the side chain reacts in much slower rate due to the mobility of the alkyl group. In addition, the γ-carbon away from the C13-OH is a tertiary-CH, which oxidizes in a much slower reaction rate.

These reactions demonstrate the stereocontrol from the hydroxyl group. Artemisinic acid (precursor of 135), isolated from *Artemisia annua* L., possesses various biological activities and has been shown to convert into artemisinin in two steps. It is believed that the oxidation takes place at C4, γ to the carbonyl function (see above). Subsequent protection of the resulting carbonyl group of 135A, removal of the methyl ester, reduction of the alkene, and photooxidation affords novel analogs of artemisinin. Colchicine, Obtained from *Colcicum* (meadow saffron) plant, is used for the treatment of gout. Its mechanism of action is similar to taxol by inhibiting microtubule polymerization. The directing effect of the C7-N-acetylamide directs oxidation at C6 of 136, providing 136A, which can be converted into various colchicine analogs. CSPVP 105 is used instead of 2 in the oxidation of 136, since the C7-S-configuration of the NHAc group affects the regiochemistry of the oxidation (see 40 to 46, Table 2). (−)-Huperzine A (precursor of 137), produced from *Huperzia serrata* plant, is used to treat various diseases including Alzheimer's disease (AD) by inhibition of acetylcholinesterase and N-methyl-D-aspartate (NMDA), a common target of current AD drugs. The C5-acetylamide group of 137 directs oxidation at C6, resulting in 137A, which is a novel analog of huperzine A. Memantine (the C1-NH$_2$ precursor of 138), an inhibitor of NMDA receptor, is used for the treatment of Alzheimer's disease. Based on oxidation result of 42, 138A is expected to form. Boldine (precursor of 139), extracted from *Litsea cubeba* root, shows reduction of rheumatoid arthritis. The oxidation takes place at C4 of 139 from the directing effect of the N—O group. Finally, taxusin (140), produced from the heartwood of the yew tree (*Taxus baccata* L.), is an intermediate of the taxol biosynthetic pathway. The oxidation of 140 occurs at C6 (γ to C5 acetoxy group), providing 140A. It is believed that C14 of 140 is blocked by methyl groups at C15, resulting in a slower reaction rate of oxidation. CSPVP 105 is used instead of 2 in the oxidation of 140, since the C5-R-stereochemistry affects the regiochemistry of oxidation (see 39 to 45, Table 2).

In summary, the oxidation produces ketone function (in some cases, the hydroxyl group), which can be converted into amines, amides, or oxime for possible enhancement of bioactivity or biological mechanistic study. Importantly, there are few methods in the literature can produce the proposed oxidized products in merely one step.

EXAMPLES

The following sets forth experimental information regarding the synthesis of various compounds in accordance with the present invention and exemplary reactions that are catalyzed with those compounds. It is to be understood, however, that these examples are provided by way of illustration and nothing therein should be taken as a limitation upon the overall scope of the invention.

$^1$H NMR spectra (obtained from a 400 MHz or a 600 MHz NMR instruments) and $^{13}$C NMR spectra (100 MHz or 150 MHz) were measured from a solution in CDCl$_3$ unless otherwise mentioned. The chemical shift data for each signal on $^1$H NMR are given in units of δ relative to TMS (δ=0) or CHCl$_3$ (δ=7.26 ppm). For $^{13}$C NMR spectra, the chemical shifts are recorded relative to CDCl$_3$ (δ=77.0 ppm). Low-resolution mass spectra were taken from an API 2000-triple quadrupole ESI-MS/MS mass spectrometer. High-resolution mass spectra were obtained using a LCT Premier time of flight mass spectrometer. IR spectra were measured directly in either solid or liquid form, High pressure reactions were conducted in a Parr Pressure Reactor (Parr Instrument Co., Moline, IL) under 2 atm, (or 30 psi) of oxygen.

Synthesis of Monomers and 5 and 6

(3R,4R)-3,4-Dihydroxy-dihydrofuran-2(3H)-one. To a cold (0° C.) solution of 17.6 g (0.1 mol) of D-isoascorbic acid (3) in 250 mL of H$_2$O, 21.2 g (0.2 mol) of Na$_2$CO$_3$ and 22.7 g (0.2 mol) of 30% H$_2$O$_2$ were added dropwise, the solution was stirred at 0° C. for 10 minutes and 42° C. for 30 minutes. To the reaction solution, 4.0 g of activated charcoal was added in portion over 10 minutes, and the mixture was stirred at 80° C. for 30 minutes, filtered through Celite during hot and washed the filter cake with 50 mL of H$_2$O. The filtrate was carefully acidified with 6 N HCl until pH 1, concentrated on a rotary evaporator and then under vacuum to give 36.9 g of solid. The crude products were purified by adding 200 mL of ethyl acetate and heating to reflux for 10 minutes. The hot solution was filtered and the filtrate containing the desired product was saved. The extraction of the product from the solid was repeated by refluxing in 200 mL of ethyl acetate and filtered. Both filtrates were combined, cooled over an ice-water bath, and the crystallized white solid was collected by filtration to give 11.0 g (94% yield) of the titled compound. $^1$H NMR (DMSO-d6) δ5.75 (dd, J=7.2, 3.2 Hz, 1H, OH), 5.34 (s, 1H, OH), 4.39-4.34 (m, 1H), 4.26 (dt, J=10, 3.2 Hz, 1H), 4.24-4.19 (m, 1H), 4.03 (dd, J=10, 3.2 Hz 1H); $^{13}$C NMR (DMSO-d6) δ177.1, 72.5, 70.1, 69.0.

(2R,3M-O-Isopropylidene-D-euthronolacione. To a solution of 1.6 g (13.6 mmol) of (3R,4R)-3,4-dihydroxy-dihydrofuran-2(3H)-one in 25 mL of anhydrous acetone under argon, 4.5 g (28.5 mmol) of CuSO$_4$ was added. The mixture was stirred for 36 hours and the precipitated inorganic salt was removed by filtration over a pad of Celite. The filtrate was concentrated to dryness leaving 2.32 g of yellow solid. The crude product was column chromatographed on silica gel using a gradient mixture of hexane and ethyl acetate as an eluent to give 1.90 g (89% yield) of the titled compound as a pale yellow solid. $^1$H NMR (CDCl$_3$) δ4.85 (bs, 1H), 4.72 (bs, 1H), 4.39 (bs, 2H), 1.42 (s, 3H), 1.34 (s, 3H).

(2R,3R)-4-Azido-4-deoxy-2,3-O-isopropylidene-D-erythronic acid. A solution of 1.90 g (12.0 mmol) of (2R, 3R)—O-isopropylidene-D-erythronolactone and 2.73 g (42.1 mmol) of NaN$_3$ in 12 mL of distilled DMF was heated to 110° C. under argon for 24 hours. The reaction solution was diluted with 500 mL of diethyl ether, 10 mL of H$_2$O and 20% aqueous HCl to pH 2, and extracted with 40 mL of ethyl acetate four times. The combined extract was washed with brine, dried (MgSO$_4$), concentrated, and column chromatographed on silica gel using a gradient mixture of hexane and ethyl acetate as an eluent to give 1.03 g (42% yield) of the titled compound as a pale yellow solid. [α]$_D$ (c 0.47, acetone); Lit. +72 (c 0.47, acetone); $^1$H NMR (CDCl$_3$) δ9.52-9.0 (bs, 1H, OH), 4.67 (d, J=7.2 Hz, 1H), 4.60-456 (m, 1H), 3.60 (dd, J=13.2, 3.2 Hz, 1H), 3.40 (dd, J=13.2, 6 Hz, 1H), 1.63 (s, 3H), 1.42 (s, 3H).

(2R,3R)-4-Amino-4-deoxy-2,3-O-isopropylidene-D-erythronic acid. To a solution of 1.01 g (5.0 mmol) of (2R,3R)-4-azido-4-deoxy-2,3-O-isopropylidene-D-erythronic acid in 100 mL of methanol, 50 mg of 10% Pd/C was added, and the mixture was shaken under 2 atm of hydrogen gas for 4 hours in a hydrogenator. The mixture was removed from the hydrogenator and filtered through a pad of Celite. The filtrate was concentrated to dryness leaving 0.86 g (99% yield) of the titled compound as a pale yellow solid. This material was used in the subsequent step without further purification. [α]$_D$ (c 1.02, 60% aqueous acetone); Lit. +92 (c 1.02, 60% aqueous acetone); $^1$H NMR (DMSO-d6) δ4.39 (d, J=Hz, 1H), 4.31-4.24 (m, 1H), 2.76 (t, J=8 Hz, 2H) 1.39 (s, 3H), 1.23 (s, 3H).

(2R,3R)-4-Amino-4-deoxy-2,3-O-isopropyildene-D-erythronolactam (4). An amount of 0.16 g (0.93 mmol) of (2R,3R)-4-amino-4-deoxy-2,3-O-isopropylidene-D-erythronic acid was placed in a sublimator and heated to 160-170° C./0.5 mm Hg under vacuum, and 92 mg (63% yield) of 4 was obtained as white solid. This material was used in the subsequent step without further purification. [α]$_D^{22}$=−60.3 (c 0.78, MeOH); Lit. $^5$-59 (c 0.78, MeOH); $^1$H NMR (CDCl$_3$) δ6.31 (bs, 1H, NH), 4.79 (t, J=5.2 Hz, 1H), 4.58 (d, J=6 Hz, 1H), 3.59 (dd, J=11, 4.8 Hz, 1H), 3.49 (d, J=11 Hz, 1H), 1.49 (s, 3H), 1.39 (s, 3H).

(2R,3R)-4-Amino-4-deoxy-2,3-O-isopropylidene-N-vinyl-D-erythronolactam (5). To a solution of 90 mg (0.57 mmol) of compound 4 in 10 mL of vinyl acetate under argon, were added 1.0 g of 3 Å molecular sieves, 13 mg (0.046 mmol) of Na$_2$PdCl$_4$, and 0.14 g (1.03 mmol) of K$_2$CO$_3$. The mixture was stirred at 50° C. for 14 hours, cooled to 25° C., filtered through Celite, concentrated under vacuum, and column chromatographed on silica gel using a gradient mixture of hexane and ethyl acetate as an eluent to give 84 mg (80% yield) of 5 as a yellow oil, [α]$_D^{22}$=−20.1 (c 1.0. CHCl$_3$); $^1$H NMR (CDCl$_3$) δ7.05 (dd, J=16.0, 9.2 Hz, 1H, CH=), 4.82-4.79 (m, 1H), 4.70 (d, J=6.4 Hz, 1H), 4.53 (d, J=9.2 Hz, 1H, =CH$_2$), 4.48 (d, J=16 Hz, 1H, =CH$_2$), 3.62 (d, J=2.8 Hz, 2H), 1.39 (s, 3H), 1.35 (s, 3H); $^{13}$C NMR (CDCl$_3$) δ169.4, 129.2, 113.0, 96.7, 78.1, 72.1, 48.7, 27.2, 25.9 MS (ESI, MeOH): m/z=184.0 ([M+H]$^+$). HRMS-ESI: m/z [M+H]$^+$ calcd for C$_9$H$_{14}$NO$_3^+$: 184.0974 found: 184.095.

(3aR,6aR)-5-Vinyl-{2,2-diethyl-dihydro-3aH-[1,3]di-oxolo[4,5-c]pyrrol}-4(5H)-one (6). A mixture of 0.25 g (1.37 mmol) of compound 5, 5 mg of ZnCl$_2$ (0.04 mmol) and 7 mL of 3-pentanone was placed in a distillation apparatus equipped with a short distill head and heated to 65° C. to remove the by-product acetone over 40 hours. The resulting mixture was diethyl ether, filtered through Celite, and washed with a small amount of diethyl ether. The filtrate was concentrated under vacuum and column chromatographed on silica gel using a gradient mixture of hexane and ethyl acetate as an eluent to give 192 mg (67% yield) of 6 as a yellow oil. [α]$_D^{22}$=−43.2 (c 1.0, CHCl$_3$); $^1$H NMR (CDCl$_3$) δ7.07 (dd, J=16.0, 9.2 Hz, 1H, CH=), 4.84-4.81 (m, 1H), 4.72 (d, J=6.4 Hz, 1H), 4.55 (d, J=9.2 Hz, 1H, =CH$_2$), 4.49 (d, J=16 Hz, 1H, =CH$_2$), 3.64 (d, J=2.8 Hz, 2H), 1.70 (q, J=7.2 Hz, 2H), 1.65 (q, J=7.2 Hz, 2H), 0.91 (t, J=6 HZ, 6H); $^{13}$C NMR (CDCl$_3$) δ169.4, 128.8, 115.5, 96.6, 78.0, 71.9, 48.6, 30.0, 29.6, 8.4, 7.6. MS (ESI, MeOH): m/z=212.2 ([M+H]$^+$) 234.3 ([M+Na]$^+$). HRMS-ESI: m/z [M+H]$^+$ calcd for C$_{11}$H$_{18}$NO$_3^+$: 212.1287 found: 212.1269.

Poly(3,4-disubstituted pyrrolidinone-co-vinyl acetate) [P(DVP-co-VAc)] 7 from compound 5 and vinyl acetate. To a solution of 10 mg (55 mmol) of N-vinylpyrrolidinone 5 and 4.7 mg (55 μmol) of vinyl acetate in 20 μL of acetone under argon was added a solution of 0.1 mg (0.6 μmol) of azobisisobutyronitiile (AIBN) in 20 μL of acetone, and the solution was stirred under reflux for 30 h. The solution was cooled to 25° C., diluted with hexane, and stirred for 10 min. The white precipitate was collected by filtration and dried under vacuum to give 12 mg (82% yield) of copolymer 7 as a white solid.

Poly(3,4-disubstituted pyrrolidinone-co-vinyl acetate) [P(DVP-co-VAc)] 8 from compound 6 and vinyl acetate. To a solution of 15 mg (55 μmol) of compound 6 and 4.7 mg (55 μmol) of vinyl acetate in 20 μL of acetone under argon was added a solution of 0.1 mg (0.6 μmol) of AIBN in 20 μL of acetone, and the solution was stirred under reflux for 30 h. The solution was cooled to 25° C., diluted with hexane, and stirred for 10 min. The white precipitate was collected by filtration and dried under vacuum to give 17.2 mg (87% yield) of copolymer 8 as a white solid.

Poly[(3aR,6aR)-2,2-dimethyl-5-vinyl-dihydro-3aH-[1,3]dioxolo[4,5-c]pyrrol-4(5H)-one](1). To a solution of 0.3 mg (0.2% by weight) of copolymer 7 in 0.5 mL of ethyl acetate under argon were added 70 mg (0.38 mmol) of compound 5 and 0.3 mg (2 µmol) of AIBN, The solution was stirred for 2 days at 70° C. (until no monomer 5 was detected by NMR spectrum of an aliquot from the reaction solution), cooled to 25° C., and diluted with hexane. The precipitate was collected by filtration and dried under vacuum to give 63 mg (90% yield) of polymer 1 as a white solid. The average molecular weight of polymer 1, 75,000 (n=410), was determined by gel permeation chromatography using TSKgel GMHx1 column and THF as solvent with a flow rate of 1 mL/min. $^1$H NMR (CDCl$_3$) δ4.7-4.3 (m, 2H, CHO), 3.8-3.0 (m, 3H, CHN, CH$_2$N), 1.6-1.1 (8H, CH$_2$, 2 CH$_3$), $^{13}$C NMR (CDCl$_3$) δ161.0, 113.0, 74.7, 72.1, 48.7, 47.8, 46.1, 45.6, 27.2, 25.9.

Poly[(3aR,6aR)-2,2-diethyl-5-vinyl-dihydro-3aH-[1,3]dioxolo[4,5-c]pyrrol-4(5H)-one] (2). To a solution of 0.4 mg (0.2% by weight) of copolymer 8 in 0.8 mL of ethyl acetate under argon were added 0.18 g (0.99 mmol) of compound 6 and 0.72 mg (4 µmol) of AIBN. The solution was stirred for 2 days at 70° C. (until no monomer 8 was detected by NMR spectrum of an aliquot from the reaction solution), cooled to 25° C., and diluted with hexane. The precipitate was collected by filtration and dried under vacuum to give 0.16 g (91% yield) of polymer 2 as a white solid. The average molecular weight of polymer 2, 92,000 (n=436), was determined by gel permeation chromatography using TSKgel GMHx1 column and THF as solvent with a flow rate of 1 mL/min. $^1$H NMR (CDCl$_3$) δ4.7-4.6 (m, 2H, CHO), 3.7-3.0 (m, 3H, CHN, CH$_2$N), 1.6-1.3 (6H, CH$_2$), 0.9-0.6 (m, 6H, CH$_3$); $^{13}$C NMR (CDCl$_3$) δ160.9, 113.5, 74.7, 73.0, 48.8, 47.7, 43.0, 42.7, 29.2, 28.5, 8.4, 7.0.

General Procedure for the preparation of Pd/Au stabilized by polymer 2. To a solution of 0.11 mL (1.12 µmol) of a 10 mM aqueous solution of Na$_2$PdCl$_4$ and 37 µL (0.37 µmol) of a 10 mM aqueous solution of HAuCl$_4$.3H$_2$O in 2 mL of deionized H$_2$O was added 3.7 mg (0.041 µmol; 0.028 equivalent based on total moles of Pd and Au atoms) of 2, and the solution was stirred at 0° C. for 0.5 h. To it was added 0.56 mg (15 µmol) of NaBH$_4$, and the resulting grey solution was stirred at 25° C. for 0.5 h to give bimetallic nanoclusters Pd/Au (3:1)-2 in aqueous solution. The solution was used in subsequent catalytic asymmetric oxidation without further manipulation. For analyses, the above Pd/Au (3:1)-2 solution was filtered through a Vivaspin 20 (Sartorius Inc.) centrifugal filter device (with a 3,000 MWCO) using a centrifugation instrument (Eppendorf Centrifuge model 5430) at 3,000 rpm for 3 min, and washed with deionized water twice to remove low molecular weight inorganic materials. The resulting nanocluster was dissolved in water, lyophilized to give Pd/Au (3:1)-2 as light brown solids, which was subjected to analyses including atomic force microscopy (AFM), dynamic light scattering (LLS), TEM, and ICP-MS. IR (neat) v 3387.5 (bs), 2921.3, 1641.9 (vs), 1491.8, 1420.8 (s), 1286.1 (s), 1217.0, 1005-846.1 (broad), 731.0 cm$^{-1}$.

Catalytic Asymmetric Oxidation of Alkenes (1S,2R)-Ethyl 1,2-dihydroxycycloheptanecarboxylate (18). To an aqueous solution of 2 mL of Pd/Au (3:1)-2 (1.12 µmol of Pd, 0.37 µmol of Au, and 0.041 µmol of 2) in a Parr pressure reactor were added 18 mL of deionized H$_2$O and 50 mg (0.30 mmol) of ethyl cyclohept-1-enecarboxylate (11). The apparatus was maintained at 30 psi of O$_2$, stirred at 50° C. for 3 days, vented to normal atmosphere, and extracted with ethyl acetate three times (20 mL each). The combined extracts were washed with water, and brine, dried (MgSO$_4$), concentrated, and column chromatographed on silica gel using a gradient mixture of hexane and ethyl acetate as eluents to give 51 mg (85% yield) of (1S,2R)-18 in 99% ee. The optical purity was determined using HPLC-chiral column [Chiralpak AD(-H) column, size: 0.46 cm×25 cm, from Daicel Chemical Industries] and hexane and isopropanol as eluents. [α]$_D^{22}$=−71.6 (c 1.0, CHCl$_3$). $^1$H NMR (CDCl$_3$) δ4.27 (q, J=5.2 Hz, 1H), 3.72 (t, J=4.8 Hz, 1H), 3.48 (b, 1H), 2.24 (d, J=9.6 Hz, 1H), 1.85-1.39 (m, 9H), 1.30 (t, J=6.8 Hz, 3H); $^{13}$C NMR (CDCl$_3$) δ172.9, 79.1, 73.8, 60.8, 32.2, 28.5, 26.2, 22.4, 20.3, 14.4. MS (ESI, MeOH): m/z=225.3 ([M+Na]$^+$). HRMS-ESI: m/z [M+H]$^+$ calcd for C$_{10}$H$_{18}$O$_4^+$: 203.1283 found: 203.1279. See, FIG. 1.

(1S,2R)-Ethyl 2-acetoxy-1-hydroxycycloheptanecarboxylate (25). To a solution of 48 mg (0.24 mmol) of (1S,2R)-18 in 2 mL of CH$_2$Cl$_2$, 24 mg (0.24 mmol) of acetic anhydride and 18 mg (0.24 mmol) of pyridine were added. The reaction was stirred under argon for 3 hours, acidified with 1N HCl to pH 5, and extracted with 10 mL of CH$_2$Cl$_2$ twice. The combined extracts were washed with brine, dried (MgSO$_4$), concentrated, and column chromatographed on silica gel using a gradient mixture of hexane and ether as an eluent to give 26 mg (45% yield) of (1S,2R)-25 and 24 mg (50% recovery) of (1S,2R)-18. [α]$_D^{22}$=+48.6 (c 0.5, CHCl$_3$); NMR (CDCl$_3$) δ5.07 (dd, J=11.2, 2.4 Hz, 1H), 4.20 (q J=7.2 Hz, 2H), 3.25 (b, 1H), 1.98 (s, 3H), 1.94-1.55 (m, 10H), 1.25 (t, J=6.8 Hz, 3H); $^{13}$C NMR (CDCl$_3$) δ175.9, 169.9, 78.6, 78.0, 62.3, 35.6, 28.6, 27.3, 23.3, 21.4, 21.2, 14.3; MS (ESI, MeOH): m/z=267.1 ([M+Na]$^+$). HRMS-ESI: m/z [M+H]$^+$ calcd for C$_{12}$H$_{21}$O$_5^+$: 245.1389, found: 245.1392.

Determination of absolute configuration of 18.

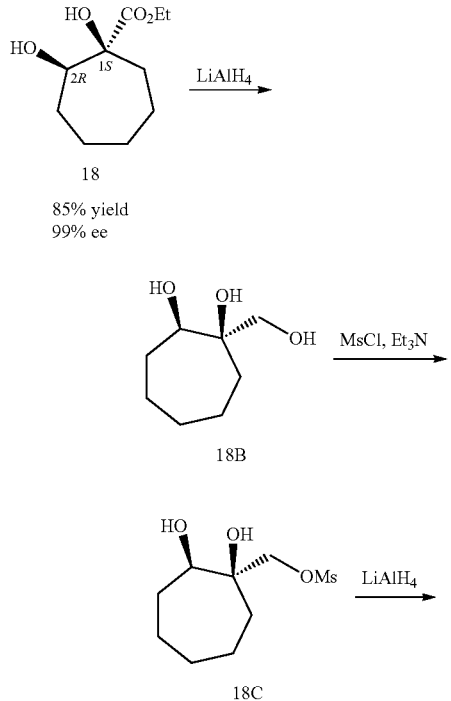

-continued

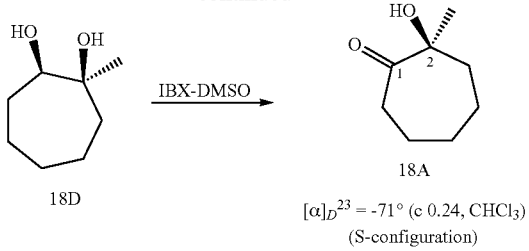

18D

18A
$[\alpha]_D^{23} = -71°$ (c 0.24, CHCl$_3$)
(S-configuration)

(1R,2R)-1-(Hydroxymethyl)cycloheptane-1,2-diol (18B). To a cold (0° C.) solution of 18 mg (0.09 mmol) of (1S,2R)-18 in 1 mL of THF under argon was added 5.1 mg (0.13 mmol) of LiAlH$_4$. The mixture was warmed to room temperature, stirred for 2 hours, and added 2 g of Na$_2$SO$_4$·10H$_2$O and one drop of CH$_3$COOH. The resulting solution was filtered through Celite, washed with 20 mL of methylene chloride, and concentrated under vacuum to give 14.1 mg of compound 18B. This material was used in the subsequent step without further purification. $^1$H NMR (CDCl$_3$) δ3.96 (t, J=9.6 Hz, 1H), 3.58 (m, 2H), 2.88 (b, 1H), 2.62 (b, 1H), 1.91-1.46 (m, 10H); MS (ESI, MeOH): m/z=161.2 ([M+H]$^+$).

[(1R,2R)-1,2-Dihydroxycycloheptyl]methyl methanesulfonate (18C). To a solution of 12 mg (0.075 mmol) of (1R,2R)-18B in 4 mL of distilled methylene chloride under argon were added 7.5 mg (0.075 mmol) of Et$_3$N and 8.5 mg (0.075 mmol) of methanesulfonyl chloride (MsCl). It was stirred for 5 hours, diluted with 5 mL of H$_2$O, and extracted with 10 mL of CH$_2$Cl$_2$ twice. The combined extracts were washed with brine, dried (MgSO$_4$), concentrated, and column chromatographed on silica gel using a mixture of diethyl ether and hexane in a ratio of 6:1 as an eluent to give 11 mg (60% yield) of (1R,2R)-18C. $[\alpha]_D^{22}$=−80.7 (c 0.1, CHCl$_3$); $^1$H NMR δ4.06 (t, J=9.6 Hz, 1H), 3.92 (m, 2H), 2.91 (s, 3H), 2.45 (b, 1H), 2.03 (d, 1H), 1.86-1.46 (m, 10H); NMR δ78.9, 76.4, 69.2, 37.9, 35.5, 31.4, 27.6, 22.9, 20.6; MS (ESI, MeOH): m/z=261.1 ([M+Na]$^+$).

(1S,2R)-1-Methylcycloheptane-1,2-diol (18D). To a cold (0° C.) solution of 9.8 mg (0.041 mmol) of (1R,2R)-18C in 1 mL of distilled THF under argon was added 1.56 mg (0.041 mmol) of LiAlH$_4$. The mixture was warmed to room temperature and stirred for 6 hours, diluted with 1 mL of water and 0.5 mL of HCl, and extracted twice with 10 mL each of ethyl acetate. The combined extracts were washed with brine, dried (MgSO$_4$), and concentrated to give 18D. This material was used in the subsequent step without further purification. $^1$H NMR (CDCl$_3$) δ3.91 (t, J=9.2 Hz, 1H), 3.39 (b, 1H), 2.23 (d, 1H), 1.88-1.42 (m, 10H), 1.30 (s, 3H); MS (ESI, MeOH): m/z=183.4 ([M+K]$^+$).

(S)-2-Hydroxy-2-methylcycloheptanone (18A). To a solution of 14 mg (0.048 mmol) of 2-iodoxybenzoic acid (IBX) in 1 mL of DMSO under argon was added 6.3 mg (0.044 mmol) of (1S,2R)-18D. The solution was stirred for 8 hours, dilute with 20 mL of CH$_2$Cl$_2$, and washed three times with 5 mL each of H$_2$O. The combined organic layer was dried (MgSO$_4$), concentrated, and column chromatographed on silica gel using a gradient mixture of hexane and diethyl ether as an eluent to give 5.2 mg (83% yield) of (S)-18A. $[\alpha]_D^{22}$=−71.2 (c=0.24, CHCl$_3$); Lit 23-71 (c 0.24, CHCl$_3$; S-configuration). $^1$H NMR$^{23}$ (CDCl$_3$) δ3.42 (b, 1H), 2.73-2.67 (m, 1H), 2.55-2.48 (m, 1H), 2.16-2.10 (m, 1H), 1.99-1.60 (m, 6H), 1.23 (s, 3H); $^{13}$C NMR (CDCl$_3$) δ216.3, 89.2, 36.9, 33.5, 31.4, 27.2, 25.9, 21.3. MS (ESI, MeOH): m/z=165.3 ([M+Na]$^+$).

Figure 2:
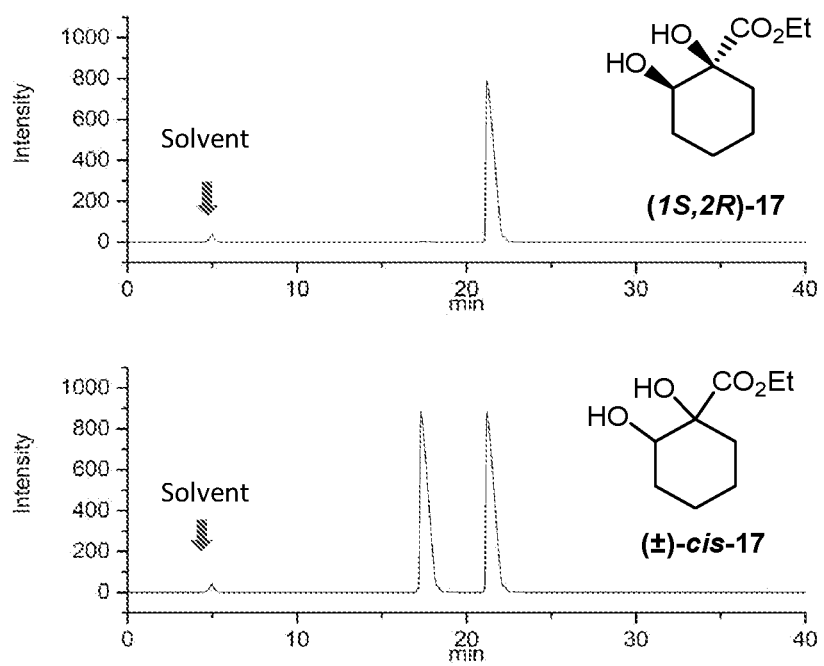
FIG. 2 depicts HPLC-chiral column graphs for (1S,2R)- and (±)-cis-Ethyl 1,2-dihydroxycyclohexanecarboxylate (17)

(1S,2R)-Ethyl 1,2-dihydroxycyclohexanecarboxylate (17). To an aqueous solution of 2 mL of Pd/Au (3:1)-2 (2.44 µmol of Pd, 0.81 µmol of Au, and 0.09 µmol of 2) in a Parr pressure reactor were added 18 mL of deionized H$_2$O and 0.1 g (0.65 mmol) of ethyl cyclohex-1-enecarboxylate (10). The apparatus was maintained under 30 psi of O$_2$, stirred at 50° C. for 3 days, vented to normal atmosphere, and extracted with ethyl acetate three times (20 mL each). The combined extracts were washed with water, and brine, dried (MgSO$_4$), concentrated, and column chromatographed on silica gel using a gradient mixture of hexane and ethyl acetate as eluents to give 102 mg (83% yield) of (1S,2R)-17 in 99% ee. The optical purity (% ee) was determined using HPLC-chiral column [Chiralpak AD(-H) column, size: 0.46 cm×25 cm, from Daicel Chemical Industries] and hexane and isopropanol as eluents. $[\alpha]_D^{22}$=−29.6 (c 1.0, CHCl$_3$). $^1$H NMR (CDCl$_3$) δ4.29 (q, J=6.8 Hz, 2H), 3.92 (t, J=9.6 Hz, 1H), 3.48 (b, 1H), 2.22 (d, 1H), 1.93-1.42 (m, 8H), 1.30 (t, J=6.8 Hz, 3H); $^{13}$C NMR (CDCl$_3$) δ177.9, 79.1, 73.8, 60.8, 33.2, 28.5, 22.4, 20.3, 14.1; MS (ESI, MeOH): m/z=211.2 ([M+Na]$^+$). HRMS-ESI: [M+H]$^+$ calcd for C$_9$H$_{17}$O$_4^+$: 189.1127, found: 189.1129. See, FIG. 2.

(1S,2P)-Ethyl 2-acetoxy-1-hydroxycyclohexanecarboxylate (24). To a solution of 50 mg (0.27 mmol) of (1S,2R)-17 in 2 mL of CH$_2$Cl$_2$ under argon were added 27 mg (0.27 mmol) of acetic anhydride and 21 mg (0.27 mmol) of pyridine. The solution was stirred for 6 hours, acidified with 1N HCl to pH 5, and extracted twice with 10 mL each of CH$_2$Cl$_2$. The combined extracts were washed with brine, dried (MgSO$_4$), concentrated, and column chromatographed on silica gel using a gradient mixture of hexane and diethyl ether as an eluent to give 26 mg (42% yield) of (1S,2R)-24 and 19 mg (38% recovery) of (1S,2R)-17. $[\alpha]_D^{22}$=+28.4 (c 0.2, CHCl$_3$); $^1$H NMR (CDCl$_3$) δ5.08 (dd, J=11.2, 2.4 Hz, 1H), 4.19 (q J=7.2 Hz, 2H), 2.85 (b, 1H), 1.98 (s, 3H), 1.78-1.55 (m, 8H), 1.25 (t, J=6.8 Hz, 3H); $^{13}$C NMR (CDCl$_3$) δ176.0, 170.3, 79.1, 78.3, 62.2, 36.2, 29.4, 28.7, 20.9, 19.8, 14.2; MS (ESI, MeOH): m/z=231.4 ([M+H]$^+$), HRMS-ESI: m/z [M+H]$^+$ calcd for C$_{11}$H$_{19}$O$_5^+$: 231.1232, found: 231.1235.

Figure 3:
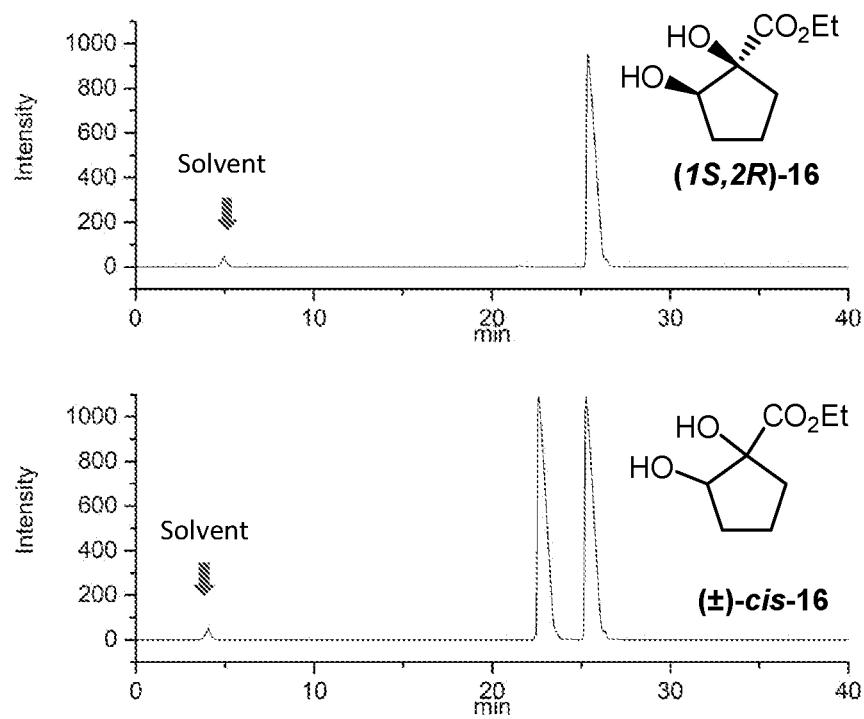
FIG. 3 depicts HPLC-chiral column graphs for (1S,2R)- and (±)-cis-Ethyl 1,2-dihydroxycyclopentanecarboxyate (16)

(1S,2R)-Ethyl 1,2-dihydroxycyclopentanecarboxylate (16). To an aqueous solution of 2 mL of Pd/Au (3:1)-2 (0.84 µmol of Pd/0.27 µmol of Au-0.0295 µmol of 2) in a Parr pressure reactor were added 18 mL of deionized H$_2$O and 0.03 g (0.214 mmol) of ethyl cyclopent-1-enecarboxylate (9). The apparatus was maintained under 30 psi of O$_2$, stirred at 50° C. for 3 days, vented to normal atmosphere, and extracted three times with ethyl acetate (20 mL each). The combined extracts were washed with water, and brine, dried (MgSO$_4$), and concentrated to dryness. The crude product was column chromatographed on silica gel using a gradient mixture of hexane and diethyl ether as eluents to give 28.3 mg (77% yield) of (1S,2R)-16 in 99% ee. The optical purity (% ee) was determined using HPLC-chiral column [Chiralpak AD(-H) column, size: 0.46 cm×25 cm, from Daicel Chemical Industries] and hexane and isopropanol as eluents. $[\alpha]_D^{22}$=−36.8 (c 1.0, CHCl$_3$). $^1$H NMR δ4.26 (q, J=7.2 Hz, 2H), 4.04 (t, J=8.8 Hz, 1H), 3.12 (b, 1H), 2.64 (b, 1H), 2.20-2.16 (m, 1H), 2.14-2.03 (m, 1H), 1.93-1.80 (m, 2H), 1.73-1.58 (m, 2H), 1.30 (t, J=6.8 Hz, 3H); $^{13}$C NMR$^{10}$ δ176.4, 79.1, 75.9, 62.0, 33.4, 27.5, 2.5.6, 14.0; MS (ESI, m/z=197.3 ([M+Na]$^+$). HRMS-ESI: m/z [M+H]$^+$ calcd for C$_8$H$_{15}$O$_4^+$; 175.0970, found: 175.0962. See, FIG. 3.

(1S,2R)-Ethyl 2-acetoxy-1-hydroxycyclopentanecarboxylate (23). A solution of 20 mg (0.12 mmol) of (1S,2R)-16, 12 mg (0.11 mmol) of acetic anhydride and 9.1 mg (0.11 mmol) of pyridine in 1 mL of CH$_2$Cl$_2$ was stirred under argon for 12 hours, acidified with 1N HCl to pH 5, and extracted twice with 10 mL each of $CH_2Cl_2$. The combined extracts were washed with brine, dried ($MgSO_4$), concentrated, and column chromatographed on silica gel using a gradient mixture of hexane and diethyl ether as an eluent to give 24 mg (96% yield) of (1S,2R)-23. $[\alpha]_D^{22}$=+125.6 (c 0.2, $CHCl_3$); $^1$H NMR ($CDCl_3$) δ5.09 (dd, J=11.2, 2.4 Hz, 1H), 4.22 (q J=7.2 Hz, 2H), 3.50 (b, 1H), 1.98 (s, 3H), 1.86-1.55 (m, 6H), 1.27 (t, J=6.8 Hz, 3H); $^{13}$C NMR ($CDCl_3$) δ175.4, 170.2, 78.5, 78.0, 62.2, 28.7, 23.9, 21.0, 17.9, 14.3; MS (ESI, MeOH): m/z=239.1 ([M+Na]$^+$). HRMS-ESI: m/z[M+H]$^+$ calcd for $C_{10}H_{17}O_5^+$: 217.1076, found: 217.1080.

Figure 4:
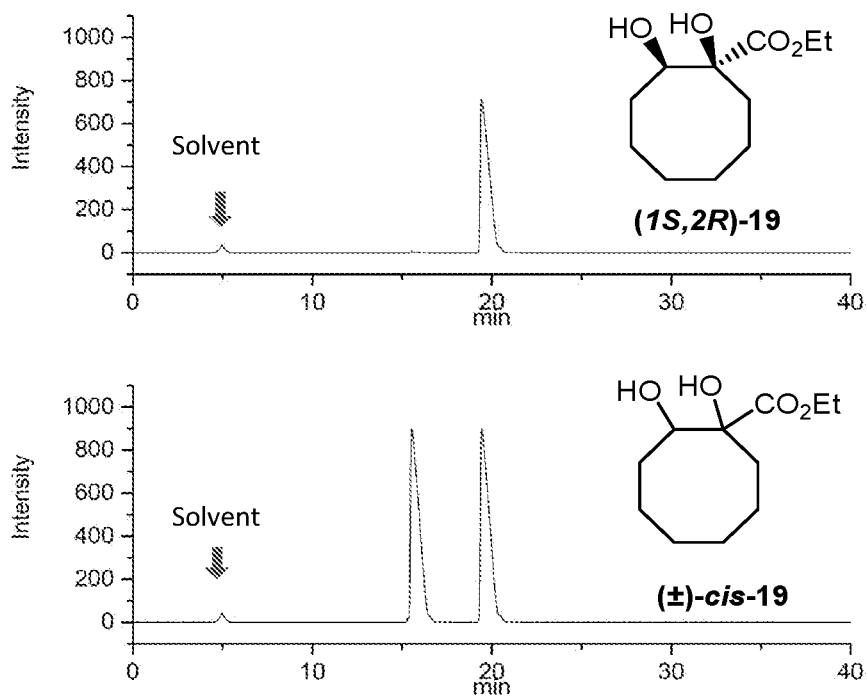
FIG. 4 depicts HPLC-chiral column graphs for (1S,2R)- and (±)-cis-Ethyl 1,2-dihydroxycyclooctanecarboxylate (19)

(1S,2R)-Ethyl 1,2-dihydroxycyclooctanecarboxylate (19). To an aqueous solution of 2 mL of Pd/Au (3:1)-2 (1.53 µmol of Pd, 0.51 µmol of Au, and 0.056 µmol of 2) in a Parr pressure reactor, were added 18 mL of deionized $H_2O$ and 74 mg (0.41 mmol) of ethyl cyclooct-1-enecarboxylate (12). The apparatus was maintained under 30 psi of $O_2$, stirred at 50° C. for 3 days, vented to normal atmosphere, and extracted three times with 20 mL each of ethyl acetate. The combined extracts were washed with water, and brine, dried ($MgSO_4$), concentrated, and column chromatographed on silica gel using a gradient mixture of hexane and ethyl acetate as eluents to give 72.3 mg (81% yield) of (1S,2R-19 in 99% ee. The optical purity (% ee) was determined using HPLC-chiral column [Chiralpak AD(-H) column, size: 0.46 cm×25 cm, from Daicel Chemical Industries] and hexane and isopropanol as eluents. $[\alpha]_D^{22}$=-16.2 (c 1.0, $CHCl_3$). $^1$H NMR. ($CDCl_3$) δ4.29 (q, J=6.8 Hz, 2H), 3.12 (t, 9.6 Hz, 1H), 3.51 (b, 1H), 2.25 (d, 1H), 2.08 (m, 1H), 1.93-1.42 (m, 12H), 1.30 (t, J=6.8 Hz, 3H); $^{13}$C NMR ($CDCl_3$) δ176.9, 79.4, 73.8, 62.2, 33.5, 31.2, 27.4, 26.5, 24.7, 21.2, 14.3; MS (ESI, MeOH): m/z=239.4 ([M+Na]$^+$; HRMS-ESI: m/z[M+H]$^+$ calcd for $C_{11}H_{21}O_4^+$: 217.1440, found: 217.1429. See, FIG. 4.

Figure 5:
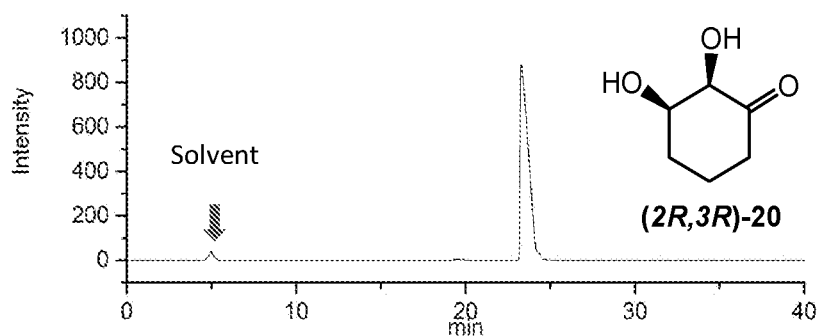
FIG. 5 depicts HPLC-chiral column graphs for (2R,3R)- and (±)-cis-2,3-Dihydroxycyclohexanone (20)
Figure 5:
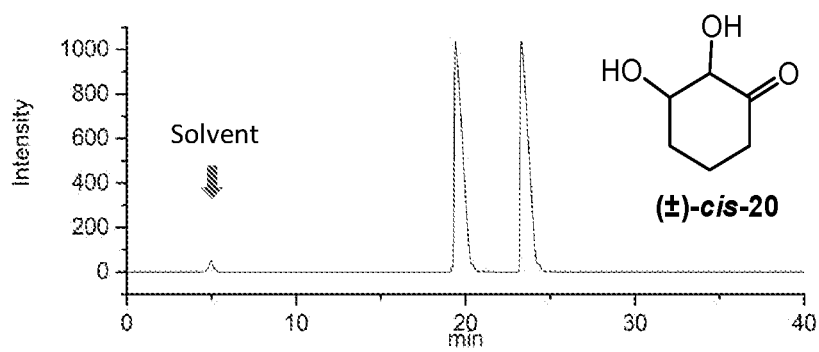

(2R,3R)-2,3-Dihydroxycyclohexanone (20). To an aqueous solution of 2 mL of Pd/Au (3:1)-2 (0.84 µmol of Pd, 0.27 µmol of Au, and 0.03 µmol of 2) in a Parr pressure reactor were added 18 mL of deionized $H_2O$ and 21 mg (0.21 mmol) of cyclohex-2-enone (13). The apparatus was maintained under 30 psi of $O_2$, stirred at 50° C. for 3 days, vented to normal atmosphere, and extracted three times with 20 mL each of ethyl acetate. The combined extracts were washed with water, and brine, dried ($MgSO_4$), concentrated, and column chromatographed on silica gel using a gradient mixture of hexane and ethyl acetate as eluents to give 24 mg (86% yield) of (2R,3R)-20 in 99% ee. The optical purity (% ee) was determined using HPLC-chiral column [Chiralpak AD(-H) column, size: 0.46 cm×25 cm, from Daicel Chemical Industries] and hexane and isopropanol as eluents. $[\alpha]_D^{22}$=-13.8 (c 0.6, $CHCl_3$); Lit. +1.48 (neat, 1=2 dm; for 2S,3S configuration). $^1$H NMR ($CDCl_3$) δ4.41 (d, J=3.2, 1H), 4.21 (dd, J=6, 2.8 Hz, 1H), 3.92 (b, 1H), 2.59-2.52 (m, 2H), 2.36 (td, J=14.8, 1.6 Hz, 1H), 2.17-2.04 (m, 2H), 1.95-1.82 (m, 2H); $^{13}$C NMR ($CDCl_3$) δ210.1, 82.6, 38.0, 31.0, 18.9; MS (ESI, MeOH): m/z=267.1 ([M+Na]$^+$). See, FIG. 5.

Figure 6:
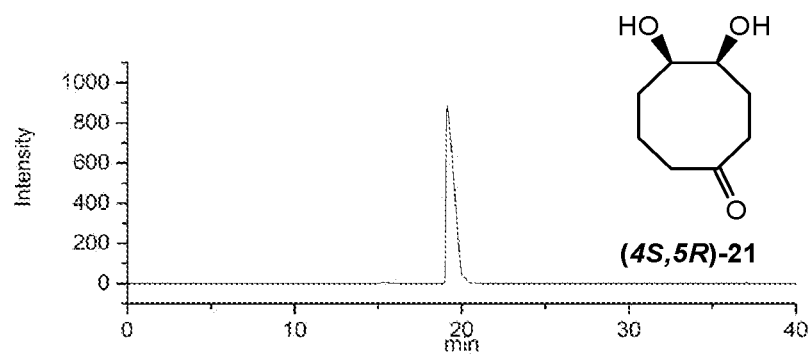
FIG. 6 depicts HPLC-chiral column graphs for (4S,5R)- and (±)-cis-4,5-dihydroxycyclooctarione (21)
Figure 6:
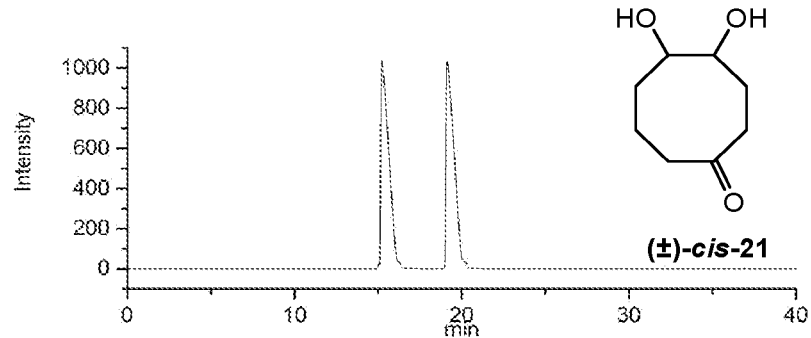

(4S,5R)-4,5-dihydroxycyclooctanone (21). To an aqueous solution of 2 mL of Pd/Au (3:1)-2 (0.75 µmol of Pd, 0.25 µmol of Au, and 0.014 µmol of 2) in a Parr pressure reactor, were added 18 mL of deionized $H_2O$ and 25 mg (0.2 mmol) of (Z)-cyclooct-4-enone (14). The apparatus was maintained under 30 psi of $O_2$, stirred at 50° C. for 3 days, vented to normal atmosphere, and extracted three times with 20 mL each of ethyl acetate. The combined extracts were washed with water, and brine, dried ($MgSO_4$), concentrated, and column chromatographed on silica gel using a gradient mixture of hexane and ethyl acetate as eluents to give 26.8 mg (85% yield) of (4S,5R)-21 in 99% ee. The optical purity (% ee) was determined using HPLC-chiral column [Chiralpak AD(-H) column, size: 0.46 cm×25 cm, from Daicel Chemical Industries] and hexane and isopropanol as eluents. $[\alpha]_D^{22}$=-16.4 (c 0.5, $CHCl_3$); $^1$H NMR $^{13}$C NMR HRMS. $^1$H NMR ($CDCl_3$) δ3.78 (d, J=7.8, 1H), 3.39-3.36 (m, 1H), 2.51-2.29 (m, 4H), 2.02-1.97 (b, 1H), 1.85-1.52. (m, 5H), 1.40-1.25 (m, 2H), 1.35-1.25 (m, 2H); $^{13}$C NMR ($CDCl_3$) δ211.6, 79.3, 78.3, 42.2, 33.5, 32.2, 26.5, 17.5; MS (ESI, MeOH): m/z=181.1 ([M+Na]$^+$). HRMS-ESI: m/z [M+H]$^+$ calcd for $C_8H_{15}O_3^+$: 159.1021, found: 159.1023. See, FIG. 6.

(S)-2-Methyheptane-1,2-diol (22). To an aqueous solution of 2 mL of Pd/Au (3:1)-2 (1.0 mmol of Pd, 0.33 µmol of Au, and 0.016 µmol of 2) in a Parr pressure reactor, were added 18 mL of deionized $H_2O$ and 30 mg (0.27 mmol) of 2-methylhept-1-ene (15). The apparatus was maintained under 30 psi of $O_2$, stirred at 50° C. for 3 days, vented to normal atmosphere, and extracted three times with 20 mL each of ethyl acetate. The combined extracts were washed with water, and brine, dried ($MgSO_4$), concentrated, and column chromatographed on silica gel using a gradient mixture of hexane and ethyl acetate as eluents to give 28.6 mg (73.4% yield) of (S)-22 in 97% ee. The optical purity (% ee) was determined using HPLC-chiral column [Chiralpak AD(-H) column, size: 0.46 cm×25 cm, from Daicel Chemical Industries] and hexane and isopropanol as eluents. $[\alpha]_D^{22}$=-2.28 (c 1.2, $CHCl_3$), Lit. +2.3 (c 1.21, $CHCl_3$; 97% ee, R-configuration); (ref. 23: JACS 2016, 138, 8730-33); $^1$H NMR (400 MHz, $CDCl_3$): δ3.47 (d, J=10 Hz, 1H), 3.41 (d, J=10 Hz, 1H), 1.9-1.7 (broad s, 2H, OH), 1.48-1.45 (m, 2H, $CH_2$), 1.35-1.30 (m, 6H), 1.17 (s, 3H), 0.90 (t, J=7.2 Hz, 3H); $^{13}$C NMR (100 MHz, $CDCl_3$): δ73.2, 69.8, 38.7, 32.5, 23.5, 23.0, 22.3, 14.2; MS (ESI, MeOH): m/z=147.3 ([M+H]$^+$).

(−)—(S)-2-Acetoxycyclohexanone (45): 93% yield and 94% ee. $[\alpha]_D^{22}$=-80.4 (c 1.2, MeOH); (R)-2-acetoxycyclohexanone is: Lit. $[\alpha]_D^{22}$=+75.8 (1.2, MeOH for 88% ee R configuration); $^1$H NMR ($CDCl_3$): δ5.17 (dd, J=11.2, 6.0 Hz, 1H), 2.35-2.54 (m, 3H), 2.16 (s, 3H), 1.78-1.89 (m, 3H), 1.66-1.76 (m, 2H); $^{13}$C NMR ($CDCl_3$): δ204.2, 170.3, 76.3, 40.1, 32.7, 26.9, 23.2; 20.1; MS (ESI; MeOH): m/z=179.5 ([M+Na]$^+$). The % ee (94%) of (S)-42 was determined by HPCL using chiral column, Chiralpak AD(-H) column [Chiralpak AD(-H) column, size: 0.46 cm×25 cm, from Daicel Chemical Industries], n-hexane/i-PrOH=95:5, flow rate 0.5 mL/min, detected at 220 nm wavelength; $t_R$=21.9 min (R enantiomer, minor), $t_R$=25.0 min (S enantiomer, major).

Compound 47: 88% yield and 92% ee, $[\alpha]_D^{22}$=+2.62 (c 1.61, MeOH); Lit. $[\alpha]_D^{22}$=+2.7 (1.6, MeOH, 96% ee, for S-configuration); $^1$H NMR ($CDCl_3$): δ4.15 (q, J=7.2 Hz, 2H), 3.79-3.77 (m, 1H), 2.60-2.58 (m, 2H), 2.78-2.25 (m, 2H), 2.14-2.05 (m, 2H), 1.89-1.78 (m, 2H), 1.25 (t, J=6.8 Hz, 3H); $^{13}$C NMR ($CDCl_3$): δ209.3, 173.7, 61.1, 43.2, 43.1, 40.9, 27.6, 24.3, 14.3; MS (ESI, MeOH): m/z=193.2 ([M+Na]$^+$). The % ee (93%) of (S)-56 was determined by HPCL using chiral column, Chiralpak AD(-H) column [Chiralpak AD(-H) column, size: 0.46 cm×25 cm, from Daicel Chemical Industries], n-hexane/i-PrOH=95:5, flow rate 0.5 mL/min, detected at 220 nm wavelength; $t_R$=32.4 min (R enantiomer, minor), $t_R$=35.2 min (S enantiomer, major).

(S)-2-Aminocyclohexanone. A solution of 15.5 mg (0.1 mmol) of 54 in 1 mL of 30% hydrazine was stirred at 70° C. under argon for 12 h (no starting material was found by TLC). The resulting solution was concentrated under vacuum, and purified by column chromatography on silica gel using a gradient mixture of hexane and ethyl acetate as eluents to give 11.4 mg (99% yield) of (S)-54A. $[\alpha]_D^{22}$=−71.3 (c 0.5, CHCl$_3$), $[\alpha]_D^{22}$=+168.1 (0.5, CHCl$_3$ for R configuration; 82% ee); (CDCl$_3$): δ3.35-3.27 (m, 1H), 2.40-2.12 (m, 3H), 1.96-1.50 (m, 5H); $^{13}$C NMR (CDCl$_3$): δ209.3, 57.7, 38.7, 27.6, 26.7, 20.8; MS (ESI, MeOH): m/z=114 ([M+H]$^+$). The spectral characteristics of this compound are in agreement with the reported molecule[15].

Figure 7:
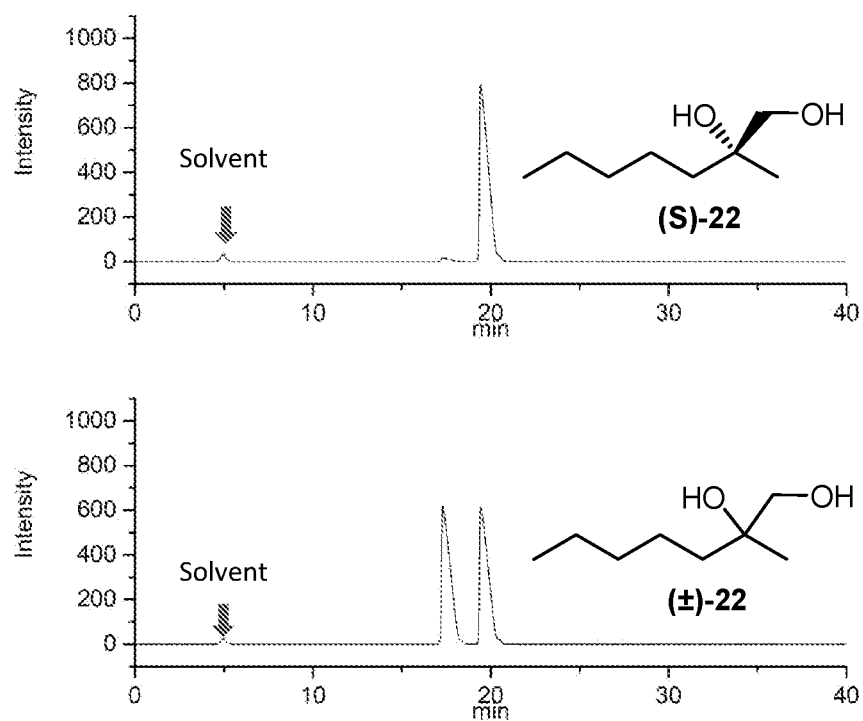
FIG. 7 depicts HPLC-chiral column graphs for (S)- and (±)-2-Methylheptane-1,2-diol (22)

(S)-2-Methylheptane-1,2-diol (22). The % ee (97%) of (S)-22 was determined by HPLC using chiral column, Chiralpak AD(-H) column [Chiralpak AD(-H) column, size: 0.46 cm×25 cm, from Daicel Chemical Industries], n-hexane/i-PrOH=85:15, flow rate 0.5 mL/min, detected at 220 nm wavelength; $t_R$=17.8 min (R enantiomer, minor), $t_R$=19.9 min (S enantiomer, major). See, FIG. 7.

Estrone 3-pivalate (142). To a solution of 0.10 g (0.37 mmol) of estrone in 3 mL of CH$_2$Cl$_2$ under argon were added 44 mg (0.37 mmol) of pivaloyl chloride and 29.2 mg (0.37 mmol) of pyridine. The solution was stirred for 10 h, acidified with 1N HCl to pH 5, and extracted three times with 20 mL each of CH$_2$Cl$_2$. The combined extracts were washed with brine, dried (MgSO$_4$), concentrated, and column chromatographed on silica gel using a gradient mixture of hexane and diethyl ether as an eluent to give 0.117 g (89% yield) of compound 142. $^1$H NMR δ7.28 (d, J=8.4 Hz, 1H), 6.84 (d, J=8.4 Hz, 1H), 6.79 (s, 1H), 2.94-2.88 (m, 2H), 2.53-2.30 (m, 3H), 2.16-1.89 (m, 4H), 1.67-1.38 (m, 6H), 1.35 (s, 9H), 0.91 (s, 3H); $^{13}$C NMR δ220.8, 177.3, 148.9, 137.9, 137.1, 126.3, 121.5, 118.6, 50.4, 47.9, 44.1, 39.0, 38.0, 35.9, 31.5, 29.4, 27.0 (3C), 26.3, 25.5, 21.5, 13.9.

t-Butyl 12β-hydroxyestrone ester (143). To an aqueous solution of 9.5 mL of Cu/Au (3:1)-(−)-2 (4.4 µmol of Cu, 1.5 µmol of Au, and 0.16 µmol of (−)-2), were added 1 mL of 30% H$_2$O$_2$, 11 mL of CH$_3$CN, and 40 mg (0.12 mmol) of t-butyl estrone ester (142). The resulting solution was stirred at 50° C. for 3 days, cooled to 25° C., and extracted three times with 20 mL each of dichloromethane. The combined extracts were washed with water, and brine, dried (MgSO$_4$), concentrated, and column chromatographed on silica gel using a gradient mixture of hexane and ethyl acetate as eluents to give 28 mg (67% yield) of 143 and 1 mg (0.3% recovery) of 44. $[\alpha]_D^{22}$=−5.6 (c 0.1, CHCl$_3$); $^1$H NMR δ7.25 (dd, J=9.0, 2.0 Hz, 1H), 6.71 (dd, J=8.0, 2.8 Hz, 1H), 6.63 (d, J=2.8 Hz, 1H), 3.98 (dd, J=10.8, 3.6 Hz, 1H), 2.94-2.87 (m, 2H), 2.59-2.46 (m, 2H), 2.41-2.30 (m, 1H); 2.20-1.98 (m, 3H), 1.78-1.72 (m, 1H), 1.63-1.35 (m, 5H), 1.36 (s, 9H), 0.98 (s, 3H); $^{13}$C NMR δ222.0, 174.1, 149.3, 136.0, 131.2, 126.0, 117.9, 116.9, 72.9, 52.2, 52.1, 48.5, 42.8, 38.6, 36.6, 35.8, 32.6, 29.6, 27.0 (3C), 21.1, 9.4. HRMS-ESI: m/z [M+H]$^+$ calcd for C$_{23}$H$_{31}$O$_4^+$: 371.2222, found: 371.2209.

General Procedure for the preparation of Cu/Au stabilized by polymer 2. To a solution of 0.34 mg (3.45 µmol) of CuCl in 8 mL deionized water, 11 mg (0.13 µmol) of 2 was added, and the mixture was stirred for 20 min over an ice-water bath. To it, 115 µL (1.15 µmol) of a 10 mM aqueous solution of HAuCl$_4$·3H$_2$O was added followed by the addition of 0.56 mg (15 µmol) of NaBH$_4$. The resulting brown solution was stirred at 25° C. for 0.5 h to give the bimetallic nanocluster Cu/Au (3:1)-2 in aqueous solution. The solution was used in subsequent catalytic asymmetric oxidation reactions without further manipulation. For analyses, the above Cu/Au (3:1)-2 solution was filtered through a Vivaspin 20 (Sartorius Inc.) centrifugal filter device (with a 3,000 MWCO) using a centrifugation instrument (Eppendorf Centrifuge model 5430) at 3,000 rpm for 3 min, and washed with deionized water twice to remove low molecular weight inorganic materials. The resulting nanocluster was dissolved in water, lyophilized to give Cu/Au (3:1)-2 as a light brown solid, which was subjected to analyses including atomic force microscopy (AFM), dynamic light scattering (DLS), TEM, JCP-MS IR, and $^1$H and $^{13}$C NMR.

Figure 8:
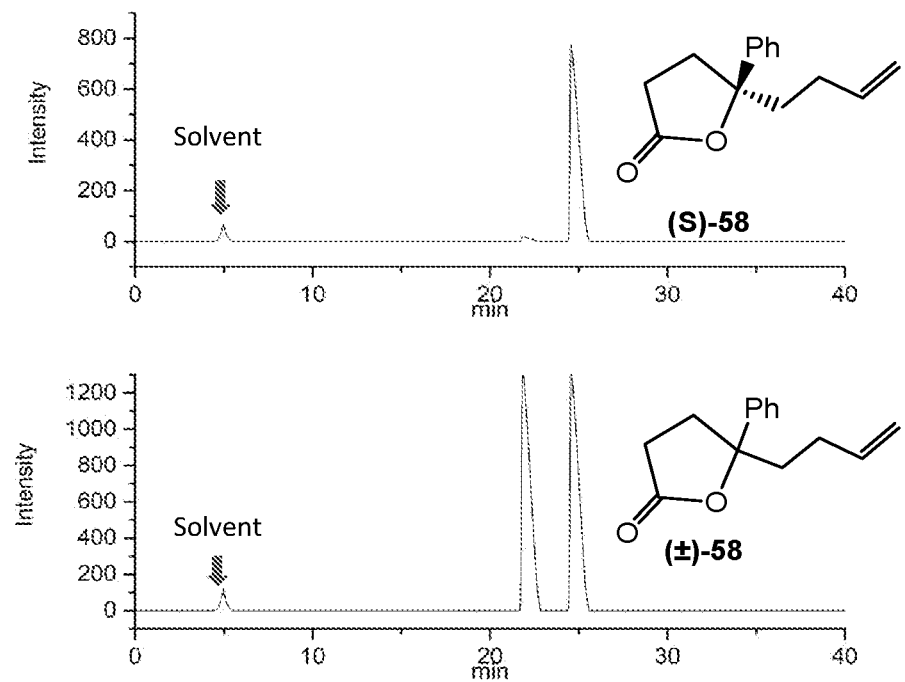
FIG. 8 depicts HPLC-chiral column graphs for (S)- and (±)-5-(3-Butenyl)-5-phenyl-dihydrofuran-2(3H)-one (58)

(S)-5-(3-Butenyl)-5-phenyl-dihydrofuran-2(3H)-one (58). To an aqueous solution of 3 mL of Cu/Au (3:1)-2 (3.7 µmol of Cu, 1.2 µmol of Au, and 0.13 µmol of 2), were added 1 mL of 30% H$_2$O$_2$, 2 mL of CH$_3$CN and 25 mg (0.116 mmol) of 5-phenylnona-1,8-dien-5-ol (53). The resulting solution was heated at 50° C. for 3 days, cooled to 25° C., and extracted three times with 10 mL each of ethyl acetate. The combined extracts were washed with water, and brine, dried (MgSO$_4$), concentrated, and column chromatographed on silica gel using a gradient mixture of hexane and ethyl acetate as eluents to give 35.3 (71% yield) of (S)-58 in 96% ee. $[\alpha]_D^{22}$=−14.6 (0.3, CHCl$_3$); $^1$H NMR δ7.39-7.22 (m, 5H), 5.84-5.74 (m, 1H), 4.95 (d, J=16.4 Hz, 1H), 4.92 (d, J=9.6 Hz, 1H), 2.53 (t, J=8.0 Hz, 2H), 2.14-1.79 (m, 6H); $^{13}$C NMR δ175.2, 142.3, 138.9, 127.2, 126.2, 125.1, 115.4, 92.2, 40.1, 34.4, 32.2, 28.1; MS (ESI, MeOH): m/z=217.1 ([M+H]$^+$). HRMS-ESI: m/z [M+H]$^+$ calcd for C$_{14}$H$_{17}$O$_2^+$: 217.1229, found: 217.1227. The optical purity (% ee) was determined using HPLC-chiral column [Chiralpak AD(-H) column, size: 0.46 cm×25 cm, from Daicel Chemical Industries] and n-hexane/i-PrOH=95:5, flow rate 0.5 mL/min, detected at 254 nm wavelength; $t_R$=22.2 min (R enantiomer, minor), $t_R$=25.0 min (S enantiomer, major). See, FIG. 8.

Figure 9:
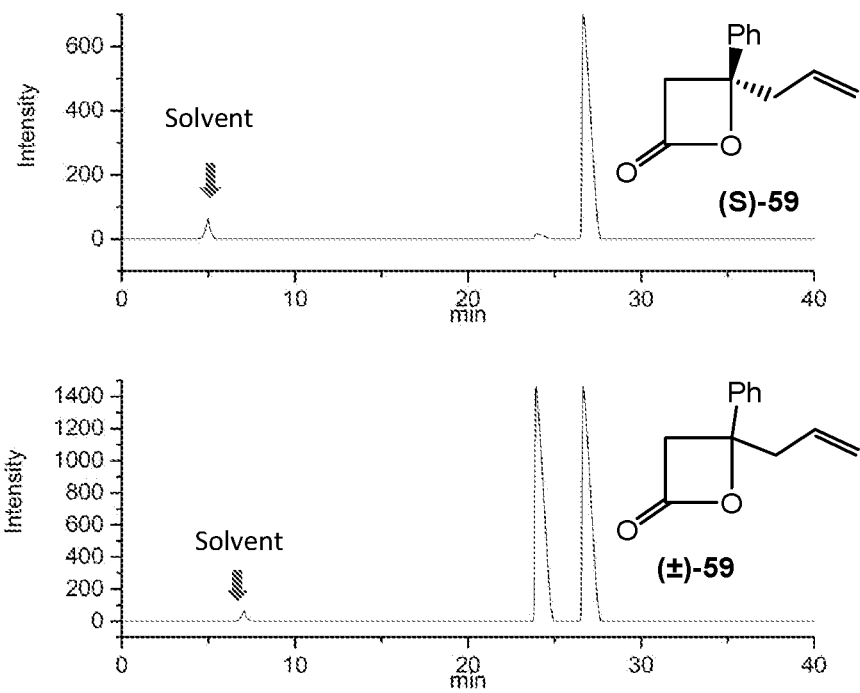
FIG. 9 depicts HPLC-chiral column graphs for (S)- and (±)-4-Allyl-4-phenyloxetan-2-one (59)

(S)-4-Allyl-4-phenyloxetan-2-one (59), To an aqueous solution of 3 mL of Cu/Au (3:1)-2 (3.9 µmol of Cu, 1.3 µmol of Au, and 0.073 µmol of 2), were added 1 mL of 30% H$_2$O$_2$, 2 mL of CH$_3$CN and 25 mg (0.133 mmol) of 4-phenylhepta-1,6-dien-4-ol (54). The resulting solution was heated to 60° C. for 6 days, cooled to 25° C., and extracted three times with 10 mL each of methylene chloride. The combined extracts were washed with water, and brine, dried (MgSO$_4$), concentrated, and column chromatographed on silica gel using a gradient mixture of hexane and ethyl acetate as eluents to give 10.9 mg (44% yield) of (S)-59 in 92% ee and 7.3 mg (29% recovery) of 54. $[\alpha]_D^{22}$=−16.8 (c 0.2, CHCl$_3$); $^1$H NMR δ7.43-7.22 (m, 5H), 5.66-5.56 (m, 1H), 5.06 (d, J=12 Hz, 1H), 5.08 (d, J=4.8 Hz, 1H), 3.70 (dd, J=12.8, 9.6 Hz, 1H), 3.48 (d, J=12.8 Hz, 1H), 2.70 (dd, J=14, 6.4 Hz, 1H), 2.52 (dd, J=14, 6.4 Hz, 1H); $^{13}$C NMR δ174.9, 142.9, 138.9, 127.3, 126.3, 125.2, 115.5, 92.8, 43.7, 37.6; MS (ESI, MeOH): m/z=189.1 ([M+H]$^+$); HRMS-ESI: m/z [M+H]$^+$ calcd for C$_{12}$H$_{13}$O$_2^+$: 189.0916, found: 189.0918. The optical purity (% ee) was determined using HPLC-chiral column [Chiralpak AD(-H) column, size: 0.46 cm×25 cm, from Daicel Chemical Industries] and n-hexane/i-PrOH=95:5, flow rate 0.5 mL/min, detected at 254 nm wavelength; $t_R$=24.3 min (R enantiomer, minor), $t_R$=27.0 min (S enantiomer, major). See, FIG. 9.

Figure 10:
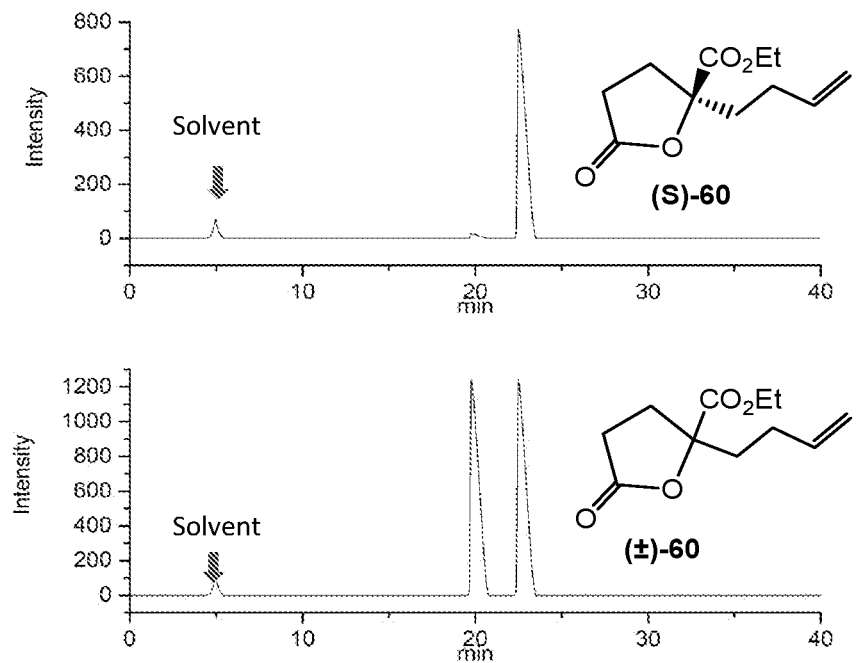
FIG. 10 depicts HPLC-chiral column graphs for (S)- and (±)-ethyl 2-(but-3-enyl)-5-oxo-tetrahydrofuran-2-carboxylate (60)

(S)-Ethyl 2-(but-3-enyl)-5-oxo-tetrahydrofuran-2-carboxylate (60). To an aqueous solution of 2 mL of Cu/Au (3:1)-(−)-2 (2.9 µmol of Cu, 1.0 µmol of Au, and 0.11 µmol of (−)-2), were added 1 mL of 30% H$_2$O$_2$, 2 mL of CH$_3$CN and 20 mg (0.095 mmol) of ethyl 2-(but-3-enyl)-2-hydroxyhex-5-enoate (55). The resulting solution was heated to 50° C. for 3 days, and extracted three times with 10 mL each of ethyl acetate. The combined extracts were washed with water, and brine, dried (MgSO$_4$), concentrated, and column chromatographed on silica gel using a gradient mixture of hexane and ethyl acetate as eluents to give 16.7 mg (84% yield) of (S)-60 in 9:3% ee and recovered 0.6 mg (3% yield) of 65. $[\alpha]_D$=+35.7 (c 0.4, CHCl$_3$); $^1$H NMR δ5.85-5.75 (m, 1H), 5.08 (dq, J=16.8, 1.2 Hz, 1H), 4.98 (dq, J=10, 1.2 Hz, 1H), 4.21 (q, J=7.0 Hz, 2H), 2.65-2.55 (m, 2H), 2.25-1.63 (m, 6H), 1.28 (t, J=7.0 Hz, 3H); $^{13}$C NMR δ177.4, 174.9, 138.9, 115.4, 97.6, 61.5, 40.1, 34.4, 30.2, 23.8, 14.9; MS (ESI, MeOH): m/z=235.0 ([M+Na]$^+$). HRMS-ESI: m/z [M+H]$^+$ calcd for $C_{11}H_{17}O_4^+$: 213.1127, found: 213.1127. The % ee (93%) of (S)-60 was determined by HPCL using chiral column, Chiralpak AD(-H) column [Chiralpak AD(-H) column, size: 0.46 cm×25 cm, from Daicel Chemical Industries], n-hexane/i-PrOH=90:10, flow rate 0.5 mL/min, detected at 220 nm wavelength; $t_R$=20.0 min (R enantiomer, minor), $t_R$=23.1 min (S enantiomer, major). See, FIG. 10.

Figure 11:
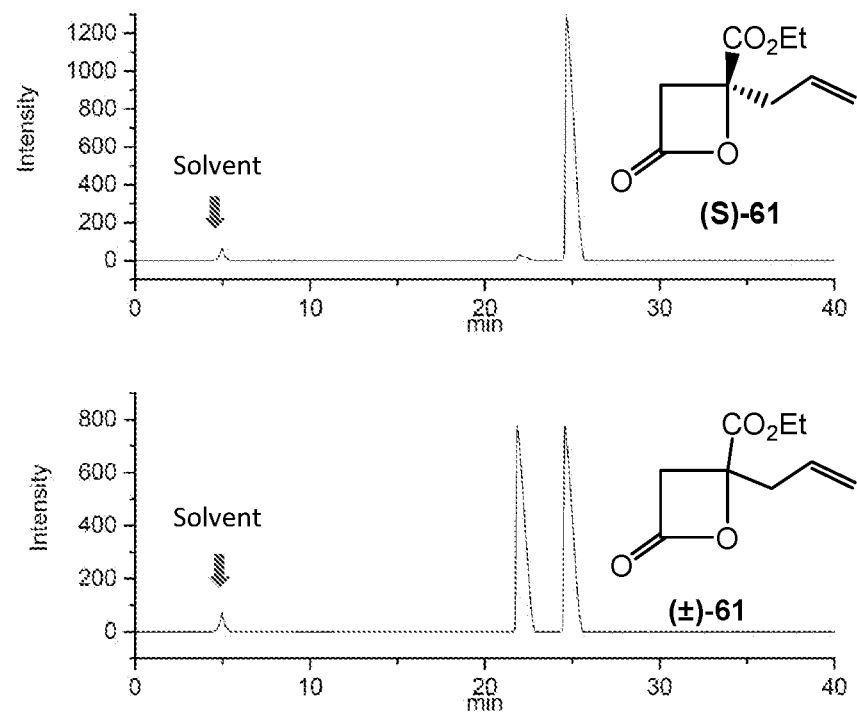
FIG. 11 depicts HPLC-chiral column graphs for (S)- and (±)-Ethyl 2-allyl-4-oxooxetane-2-carboxylate (61).

(S)-Ethyl 2-allyl-4-oxooxetane-2-carboxylate (61). To an aqueous solution of 3 mL of Cu/Au (3:1)-2 (3.4 μmol of Cu, 1.4 μmol of Au, and 0.13 μmol of 2), were added 2 mL of 30% $H_2O_2$, 3 mL of $CH_3CN$ and 20 mg (0.115 mmol) of ethyl 2-allyl-2-hydroxypent-4-enoate (56). The resulting solution was stirred to 50° C. for 7 days, and extracted three times with 15 mL each of methylene chloride. The combined extracts were washed with water, and brine, dried (MgSO$_4$), concentrated, and column chromatographed on silica gel using a gradient mixture of hexane and ethyl acetate as eluents to give 6.2 mg (33% yield) of (S)-61 in 93% ee and 1 mg (5% recovery) of 56. Compound (S)-61: $[α]_D$=+33.7 (c 0.2, CHCl$_3$); $^1$H NMR δ5.83-5.73 (m, 1H), 5.10 (d, J=14.4 Hz, 1H), 5.09 (d, J=11.2 Hz, 1H), 4.21 (q, J=7.0 Hz, 2H), 3.70 (d, J=12.8 Hz, 1H), 3.49 (d, J=12.8 Hz, 1H), 2.52-2.40 (m, 2H), 1.28 (t, J=7.0 Hz, 3H); $^{13}$C NMR δ176.9, 173.3, 137.7, 115.3, 86.6, 61.4, 40.2, 25.8, 14.8; MS (ESI, MeOH): m/z=207.0 ([M+Na]$^+$); HRMS-ESI: m/z [M+H]$^+$ calcd for $C_9H_{13}O_4^+$: 185.0814, found: 185.0811. The optical purity (% ee) was determined using HPLC-chiral column [Chiralpak AD(-H) column, size: 0.46 cm×25 cm, from Daicel Chemical Industries] and a gradient mixture of hexane and isopropanol as eluents. See, FIG. 11.

Figure 12:
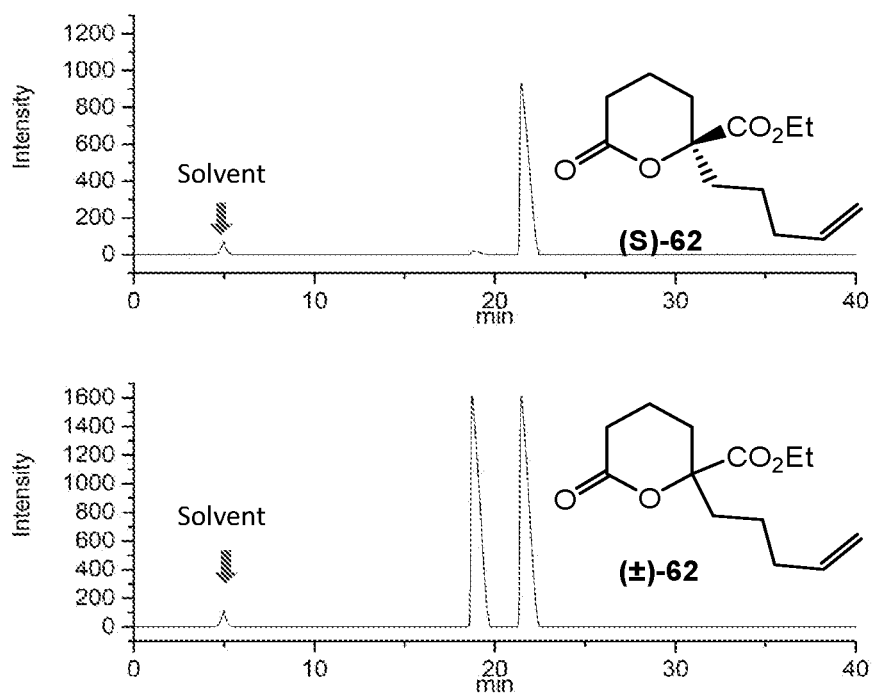
FIG. 12 depicts HPLC-chiral column graphs for (S)- and (±)-ethyl 6-oxo-2-(pent-4-enyl)-tetrahydro-2H-pyran-2-carboxylate (62)

(S)-Ethyl 6-oxo-2-(pent-4-enyl)-tetrahydra-2H-pyran-2-carboxylate (62). To an aqueous solution of 3 mL of Cu/Au (3:1)-(-)-2 (4.8 μmol of Cu, 1.6 μmol of Au, and 0.17 μmol of (-)-2), were added 2 mL of 30% $H_2O_2$, 4 mL of $CH_3CN$ and 40 mg (0.0845 mmol) of ethyl 2-hydroxy-2-(pent-4-enyl)hept-6-enoate (57). The resulting solution was heated to 50° C. for 6 days, and extracted three times with 25 mL each of methylene chloride. The combined extracts were washed with water, and brine, dried (MgSO$_4$), concentrated, and column chromatographed on silica gel using a gradient mixture of hexane and ethyl acetate as eluents to give 33 mg (83% yield) of (S)-62 in 93% ee and recovered 2 mg (6% yield) of 66. $[α]_D$=+17.5 (c 0.3, CHCl$_3$); $^1$H NMR δ5.84-5.74 (m, 1H), 4.95 (d, J=16.4 Hz, 1H), 4.92 (d, J=9.6 Hz, 1H), 4.21 (q, J=6.8 Hz, 2H), 2.50 (t, 8.0 Hz, 2H), 2.18-1.40 m, 10H), 1.25 (t, J=7.2 Hz, 3H); $^{13}$C, NMR δ177.7, 174.7, 138.9, 115.4, 89.0, 61.4, 37.5, 34.4, 32.9, 29.3, 24.9, 23.8, 14.8; MS (ESI, MeOH): m/z=263.1 ([M+Na]$^+$. HRMS-ESI: m/z [M+H]$^+$ calcd for $C_{13}H_{21}O_4^+$: 241.1440, found: 241.1440. The % ee (93%) of (S)-62 was determined by HPCL using chiral column, Chiralpak AD(-H) column [Chiralpak AD(-H) column, size: 0.46 cm×25 cm, from Daicel Chemical Industries], n-hexane/i-PrOH=90:10, flow rate 0.5 mL/min, detected at 220 nm wavelength; $t_R$=18.6 min (R enantiomer, minor), $t_R$=22.0 min (S enantioiner, major). See, FIG. 12.

Figure 13:
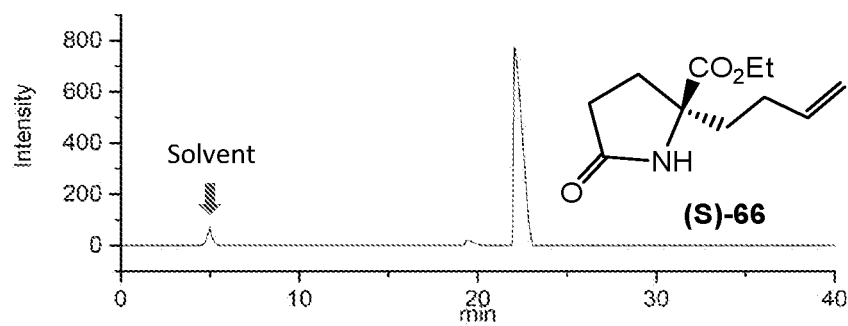
FIG. 13 depicts HPLC-chiral column graphs for (S)- and (±)-Ethyl 2-(but-3-enyl)-5-oxopyrrolidine-2-carboxylate (66)
Figure 13:
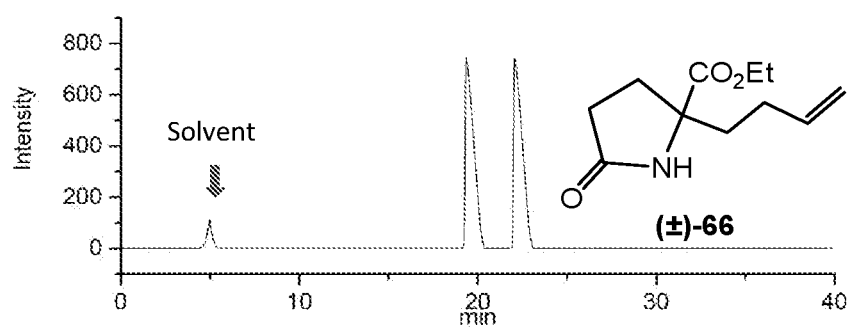

(S)-Ethyl 2-(but-3-enyl)-5-oxopyrrolidine-2-carboxylate (66). To an aqueous solution of 15 mL of Cu/Au (3:1)-2 (21.3 μmol of Cu, 7.1 μmol of Au, and 0.7 μmol of 2), were added 5 mL of 30% $H_2O_2$, 5 mL of $CH_3CN$ and 150 mg (0.711 mmol) of ethyl 2-amino-2-(but-3-enyl)hex-5-enoate (63). The resulting solution was stirred to 50° C. for 3 days, cooled to room temperature, and extracted three times with 40 mL each of methylene chloride. The combined extracts were washed with water, and brine, dried (MgSO$_4$), concentrated, and column chromatographed on silica gel using a gradient mixture of hexane and ethyl acetate as eluents to give 126 mg (84% yield) of (S)-66 in 95% ee. $[α]_D^{22}$=+18.6 (c 0.2, CHCl$_3$); $^1$H NMR δ8.18 (bs, 1H), 5.83-5.71 (m, 1H), 5.10 (d, J=17.2 Hz, 1H), 4.95 (d, J=9.2 Hz, 1H), 4.24 (q, J=6.8 Hz, 2H), 2.62 (t, J=8.4 Hz, 1H), 2.21-1.64 (m, 6H), 1.28 (t, J=7.2 Hz, 3H); $^{13}$C NMR δ176.9, 173.5, 138.1, 115.1, 61.6, 57.0, 40.1, 38.9, 33.4, 23.2, 14.8; MS (ESI, MeOH): m/z=234.6 ([M+Na]$^+$). HRMS-ESI: m/z [M+H]$^+$ calcd for $C_{11}H_{18}NO_3^+$: 212.1287, found: 212.1288. The optical purity (% ee) was determined using HPLC-chiral column [Chiralpak AD(-H) column, size: 0.46 cm×25 cm, from Daicel Chemical Industries] and a gradient mixture of hexane and isopropanol as eluents. See, FIG. 13.

Figure 14:
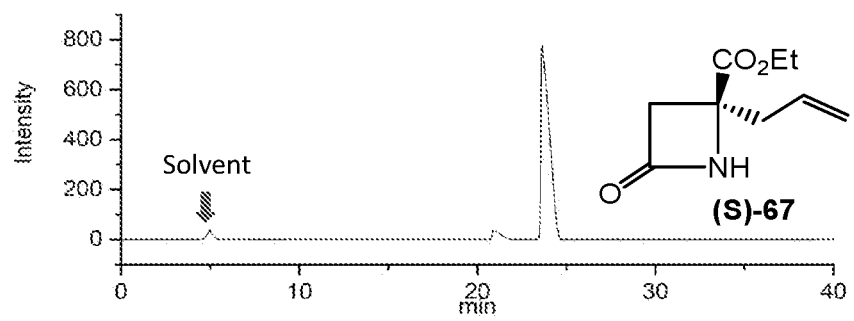
FIG. 14 depicts HPLC-chiral column graphs for (S)- and (±)-ethyl 2-allyl-4-oxoazetidine-2-carboxylate (67)
Figure 14:
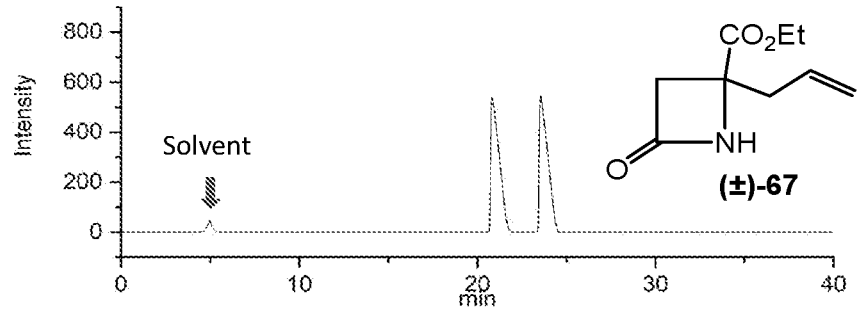

(S)-Ethyl 2-allyl-4-oxoazetidine-2-carboxylate (67). To an aqueous solution of 2 mL of Cu/Au (3:1)-2 (3.2 μmol of Cu, 1.0 μmol of Au, and 0.06 μmol of (-)-2), were added 1 mL of 30% $H_2O_2$, 2 mL of $CH_3CN$ and 20 mg (0.1093 mmol) of ethyl 2-allyl-2-aminopent-4-enoate (64). The resulting solution was stirred to 50° C. for 7 days, and extracted three times with 20 mL each of methylene chloride. The combined extracts were washed with water, and brine, dried (MgSO$_4$), concentrated, and column chromatographed on silica gel using a gradient mixture of hexane and ethyl acetate as eluents to give 12.8 mg (64% yield) of (S)-67 in 92% ee. $[α]_D$=+33.7 (c 0.2, CHCl$_3$); $^1$H NMR δ7.28 (bs, 1H), 5.80-5.70 (m, 1H), 5.16 (d, J=19 Hz, 1H), 5.15 (d, J=10.0 Hz, 1H), 4.21 (q, J=7.0 Hz, 2H), 3.21-3.12 (m, 2H), 2.62-2.45 (m, 1H), 2.31-2.28 (m, 1H), 1.28 (t, J=7.0 Hz, 3H); $^{13}$C NMR δ177.0, 173.3, 137.7, 115.3, 61.8, 57.0, 38.4, 24.3, 14.0; MS (ESI, MeOH): m/z=206.2 ([M+Na]$^+$). HRMS-ESI: m/z [M+H]$^+$ calcd for $C_9H_{14}NO_3^+$: 184.0974, found: 184.0963. The ee (92%) of (S)-67 was determined by HPCL using chiral column, Chiralpak AD(-H) column [Chiralpak AD(-H) column, size: 0.46 cm×25 cm, from Daicel Chemical Industries], n-hexane/i-PrOH=90:10, flow rate 0.5 mL/min, detected at 220 nm wavelength; $t_R$=20.9 min (R enantiomer, minor), $t_R$=24.1 min (S enantiomer, major). See, FIG. 14.

Figure 15:
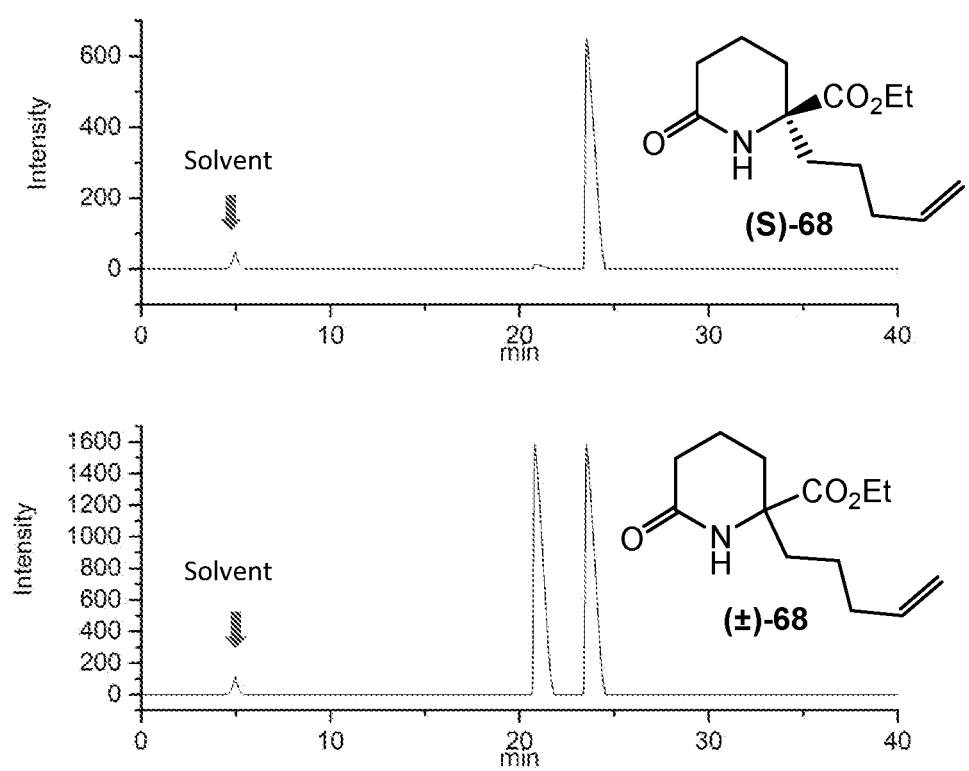
FIG. 15 depicts HPLC-chiral column graphs for (S)- and (±)-Ethyl 6-oxo-2-(pent-4-enyl)piperidine-2-carboxylate (68)

(S)-Ethyl 6-oxo-2-(pent-4-enyl)piperidine-2-carboxylate (68). To an aqueous solution of 2 mL of Cu/Au (3:1)-2 (2.5 μmol of Cu, 0.8 μmol of Au, and 0.046 μmol of 2), were added 1 mL of 30% $H_2O_2$, 2 mL of $CH_3CN$ and 20 mg (0.0845 mmol) ethyl 2-amino-2-(pent-4-enyl)hept-6-enoate (65). The resulting solution was stirred at 50° C. for 5 days, cooled to room temperature, and extracted three times with 15 mL each of methylene chloride. The combined extracts were washed with water, and brine, dried (MgSO$_4$), concentrated, and column chromatographed on silica gel using a gradient mixture of hexane and ethyl acetate as eluents to give 18.6 mg (93% yield) of (S)-68 in 94% ee. $[α]_D^{22}$=+48.7 (c 0.5, CHCl$_3$); $^1$H NMR δ5.79-5.69 (m, 1H), 4.96 (d, J=17.2 Hz, 1H), 4.92 (d, J=10.0 Hz, 1H), 4.19 (q, J=7.2 Hz, 2H), 2.32 (td, J=10.2, 2.4 Hz, 2H) 1.77-1.37 (m, 11H), 1.24 (t, J=7.2 Hz, 3H); $^{13}$C NMR δ177.9, 172.4, 138.9, 116.4, 61.4, 56.5, 39.0, 34.4, 31.1, 27.0, 23.5, 22.8, 14.8; MS (ESI, MeOH): m/z=262.2 ([M+Na]$^+$). HRMS-ESI: m/z [M+H]$^+$ calcd for $C_{13}H_{22}NO_3^+$: 240.1660, found: 240.1651. The optical purity (% ee) was determined using HPLC-chiral column [Chiralpak AD(-H) column, size: 0.46 cm×25 cm, from Daicel Chemical Industries] and n-hexane/i-PrOH=90:10, flow rate 0.5 mL/min, detected at 220 nm wavelength; $t_R$=21.2 min (R enantiomer, minor), $t_R$=24.5 min (S enantiomer, major). See, FIG. 15.

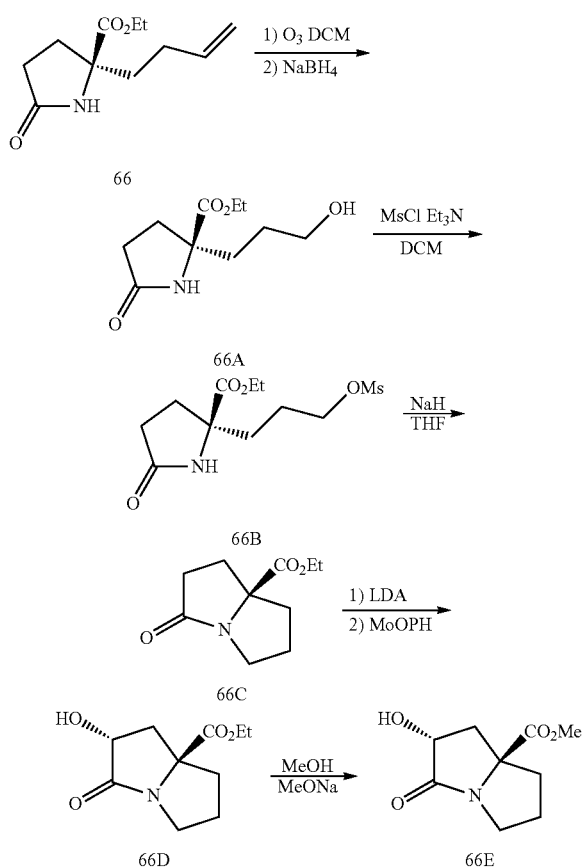

(S)-Ethyl 2-(3-hydroxypropyl)-5-oxopyrrolidine-2-carboxylate (66A). To a solution of 12 mL of methylene chloride under argon at −78° C., ozone was bubbled into it for 3 minutes while the argon was turned off, to give a blue solution. To it, 35 mg of 66 (0.167 mmol) was added and stirred for 5 minutes at −78° C. (until no starting material remaining). The remaining ozone was evaporated by introducing argon into the system for 10 minutes, To it, 12.6 mg (0.33 mmol) of $NaBH_4$ and 0.5 mL of methanol were added, and the solution was warmed up to room temperature and stirred for 1 hour. The reaction to was quenched by 2 mL of saturated aqueous $NH_4Cl$ solution and extracted three times with 40 mL each of methylene chloride. The combined extracts were washed with water, and brine, dried ($MgSO_4$), concentrated, and column chromatographed on silica gel using a gradient mixture of hexane and ethyl acetate as eluents to give 26.2 mg (75% yield) of 66A. $^1$H NMR δ4.29 (q, J=7.0 Hz, 2H), 3.53-3.61 (m, 2H), 2.55-2.45 (m, 1H), 2.25-1.62 (m, 8H), 1.32 (t, J=7.0 Hz, 3H); $^{13}$C NMR δ177.0, 173.4, 65.8, 62.6, 61.6, 35.0, 29.6, 27.2, 24.1, 14.8; $^{13}$C NMR δ177.0, 173.4, 65.8, 62.6, 61.6, 35.0, 29.6, 27.2, 24.1, 14.8; MS (ESI, MeOH): m/z=216.3 ([M+H]$^+$).

(S)-Ethyl 2-(3-(methylsulfonyloxy)propyl)-5-oxopyrrolidine-2-carboxylate (66B). To a cold (0° C.) solution of 66A (26 mg, 0.123 mmol) and triethylamine (13.6 mg, 0.135 mmol) in 2 mL of dichloromethane under argon was added methanesulfonyl chloride (15.4 mg, 0.135 mmol) dropwise. The reaction solution was stirred for 8 hours at room temperature, diluted with 0.5 mL of water and extracted with methylene chloride (3×10 mL). The combined organic layer was washed with brine, dried over anhydrous sodium sulfate, and concentrated on a rotary evaporator and then under vacuum to give 29 mg (80.4% yield) 66B. The residue was used in the subsequent step without further purification. $^1$H NMR δ4.22 (q, J=7.2 Hz, 2H), 3.96-3.85 (m, 2H), 2.95 (s, 3H), 2.53-2.45 (m, 1H), 2.22-1.64 (a series of m, 8H), 1.32 (t, J=6.8 Hz, 3H); $^{13}$C NMR δ177.0, 173.4, 70.0, 65.9, 61.6, 37.9, 35.0, 29.9, 26.1, 20.5, 14.9; MS (ESI, MeOH): m/z=316.3 ([M+Na]$^+$). (S)-Ethyl 3-oxo-benyhydro-1H-pyrrolizine-7a-carboxylate (66c). To a cold (0° C.) solution of 29 mg (0.099 mmol) of 66B in 2 mL distilled THF under argon was added NaH (2.5 mg, 0.104 mmol), and the solution was stirred at room temperature for 3 hour, quenched with 0.5 mL of water, and extracted with methylene chloride (3×10 mL). The combined organic layer was washed with brine, dried over anhydrous sodium sulfate, concentrated under vacuum, and column chromatographed on silica gel using a gradient mixture of hexane and ethyl acetate as eluents to give 16 mg (78% yield) of 66C. $^1$H NMR δ4.20 (q, J=7.0 Hz, 2H), 3.61-3.48 (m, 2H), 2.55 (dd, J=4.8, 1.2 Hz, 1H), 2.38 (d, J=4.4 Hz, 1H), 2.25-1.80 (a series of m, 6H), 1.30 (t, J=7.0 Hz, 3H); $^{13}$C, NMR δ175.4, 173.4, 67.7, 61.6, 43.2, 42.4, 32.2, 27.2, 20.0, 14.8, MS (ESI, MeOH): m/z=220.1 ([M+Na]$^+$).

(2S,7aS)-Ethyl-2-hydroxy-3-oxo-hexahydro-1H-pyrrolizine-7a-carboxylate (66D). To a cold (−78° C.) solution of 0.11 mL (1.05 mmol) of diisopropylamine in 5 mL distilled THF under argon was added 1 ml, of n-BuLi (1M in hexanes). The resulting solution was warmed up to room temperature and stirred for 1 hour to give a LDA solution. To a cold (−78° C.) solution of 66C (19 mg, 0.096 mmol) in 1 mL of distilled THF under argon, 0.6 mL of LDA solution was added dropwise and stirred at room temperature for 30 minutes. To 62.5 mg (0.144 mmol) of MoOPH at −30° C. under argon was added the above anion solution via cannula, and the solution was stirred for 40 minutes, warmed to room temperature, diluted with 2 mL of saturated aqueous $Na_2SO_3$ solution, and extracted with ethyl acetate (3×10 mL). The combined organic layer was washed with brine, dried over anhydrous sodium sulfate, concentrated to dryness, and column chromatographed on silica gel using a gradient mixture of hexane and ethyl acetate as eluents to give 11.7 mg (57% yield) of (2S,7aS)-66D and 1.6 mg (7.8% yield) of (2R,7aS)-66D. $[α]_D^{22}$=−8.9 (c 0.88, $CHCl_3$), $^1$H NMR δ5.91 (bs, 1H), 4.41 (d, J=7.0, 1H), 4.20 (q, J=7.2 Hz, 2H), 3.64 (d, J=10.0 Hz, 1H), 3.28 (dd, J=10.4, 2.0 Hz, 1H), 2.54 (d, J=12.8 Hz, 1H), 2.32 (d, J=12.8 Hz, 1H), 2.26 (d, J=11.2 Hz, 1H), 2.14-1.98 (m, 2H), 1.62 (m, 1H), 1.24 (t, J=7.0 Hz, 3H); $^{13}$C NMR δ174.4, 173.7, 74.1, 72.2, 61.6, 41.0, 39.9, 36.0, 25.5, 14.9; MS (ESI): m/z=236.1 ([M+Na]$^+$). (2R,7aS)-Methyl 2-hydroxy-3-oxo-hexahydro-1H-pyrrolizine-7a-carboxylate (66E). To a solution of (11.5 mg, 0.054 mmol) 660 (11.5 mg, 0.054 mmol) in 2 mL of distilled MeOH under argon was added 1 mg of MeONa, and the solution was stirred at room temperature for 8 hours, concentrated on a rotary evaporator, and diluted with 20 mL of methylene chloride. The solution was washed with 5 rnL of water, and 5 mL of brine, dried over anhydrous sodium sulfate, concentrated under vacuum, and column chromatographed on silica gel using a gradient mixture of hexane and ethyl acetate as eluents to give 4.2 mg (37% yield) of 66E and 4.8 mg (41% recovery) of 66D. Compound 66E: $[α]_D^{22}$=−10.2 (c 0.88, $CHCl_3$), Lit. −10.2 (c 0.88, $CHCl_3$); $^1$H NMR ($CDCl_3$): δ4.95 (bs, 1H), 4.37 (d, J=6.8, 1H), 3.76 (s, 3H), 3.64 (dt, J=10.4, 1.2 Hz, 1H), 3.28 (dd, J=10.4, 2.0 Hz, 1H), 2.54 (d, J=12.8 Hz, 1H), 2.35 (d, J=12.8 Hz, 1H), 2.23 (d, J=11.2 Hz, 1H), 2.14-2.00 (m, 2H), 1.70-162 (m, 1H); $^{13}$C NMR ($CDCl_3$): δ174.4, 173.8, 74.1, 72.2, 52.8, 41.2, 39.8, 36.0, 25.5; m/z=222.1 ([M+Na]$^+$).

Synthesis of 3S,4S-Chiral Polymers [(S,S)-CSPVPs]

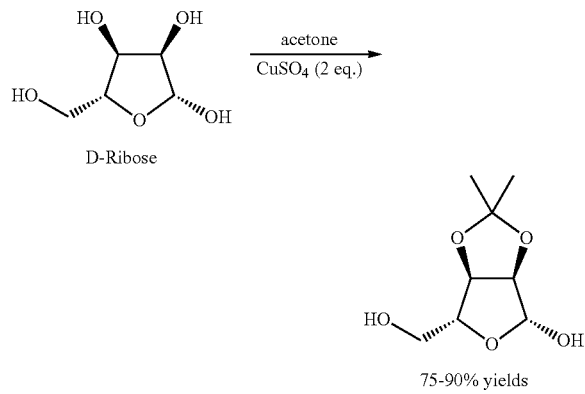

D-Ribose 75-90% yields

A mixture of 15 g (0.1 mol) of D-ribose and 25 g (0.16 mol) of anhydrous CuSO₄ in 100 mL of dry acetone under argon was stirred at 25° C. for 60 h. The reaction mixture was filtered to remove copper salt, and the filtrate was concentrated under a rotary evaporator and then under vacuum to give 14.24 g (75% yield) of the acetonide.

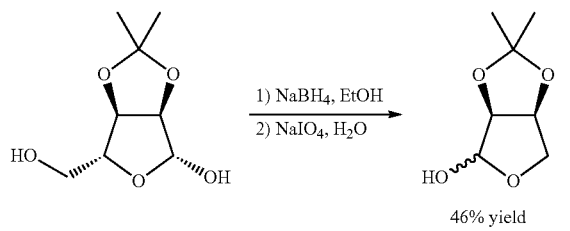

46% yield

To a cold (0° C.) solution of 3.47 g (0.018 mol) of the acetonide diol in 20 mL of ethanol and 100 mL, of water was added dropwise of a cold (0° C.) solution of 1.04 g (0.027 mol) of sodium borohydride in 20 mL of water and stirred at 25° C. for 20 h. To it, 12 mL of 10% aqueous acetic acid solution was added to adjust the pH to ~5. The solution was diluted with 80 mL of water, cooled over ice-water bath, and added a solution of 4.62 g (0.0216 mol) of NaIO₄ in 20 mL of water over 5 minutes. The reaction solution was stirred at 25° C. for 3 hours, concentrated on a rotary evaporator to 50 mL, and extracted with ethyl acetate four times (50 mL each). The combined extracts were washed with water three time, brine, dried over anhydrous Na₂SO₄, concentrated to dryness to give 1.32 g (46% yield) of the lactol.

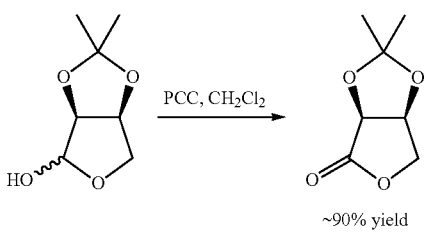

~90% yield

To a solution of 0.94 g (5.9 mmol) of the lactol in 30 mL of dichloromethane under argon were added 3.8 g (17.6 mmol) of pyridinium chlorochromate (PCC) and 5 g of is neutral alumina. The mixture was stirred at 25° C. for over night, filtered through a pad of Celite, and washed the Celite with dichloromethane. The filtrate was washed with water twice and brine, dried over anhydrous Na₂SO₄, concentrated to dryness to give 0.83 g (90% yield) of the lactone.

Synthesis of 3S,4S-(+)-2S Polymers [(S,S)-(+)-2S]

Scheme 1A. Synthesis of chiral polymer (+)-2S.

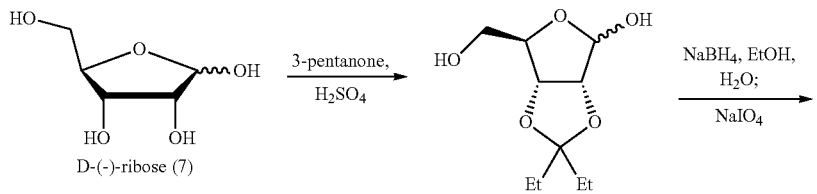

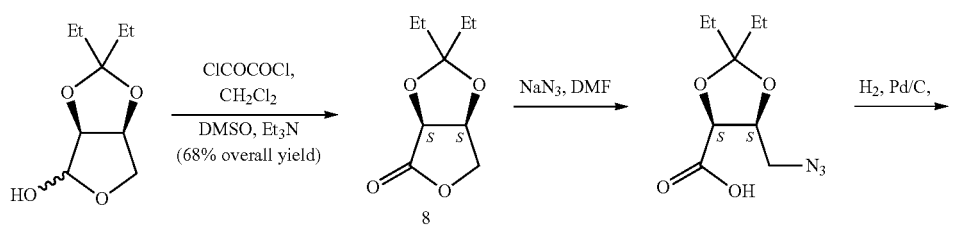

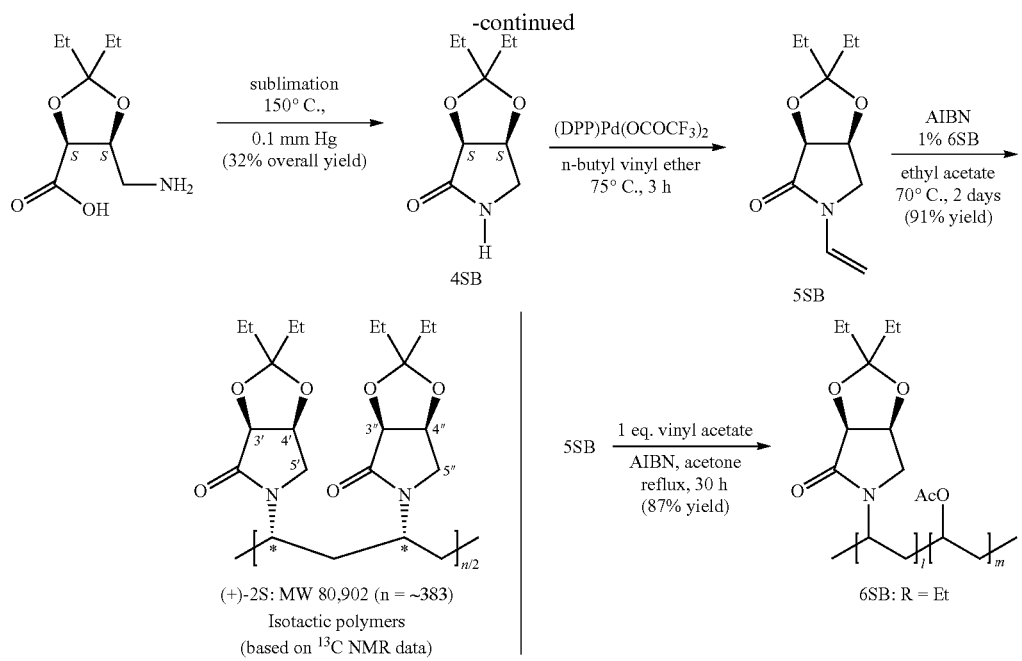

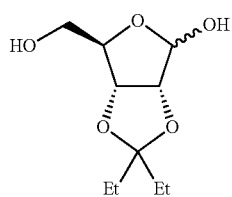 [SMILES: CCC1(CC)O[C@@H]2[C@@H](CO)OC(O)[C@@H]2O1]

2,3-O-Isopentylidene-D-ribofuranose or (3aR,6R,6aR)-2,2-diethyl-6-(hydroxymethyl)-tetrahydrofuro[3,4-d][1,3]dioxol-4-ol. To a solution of 10.0 g (0.067 mol) of D-ribose in 300 mL of 3-pentanone was added 3 mL of conc. H$_2$SO$_4$, and the solution was stirred at 25° C. for 40 h. To it, ammonia gas was added for 10 minutes until to no precipitate was formed. The white precipitate was removed by filtration and the filtrate was concentrated on a rotary evaporator. The residue was diluted with 200 mL of water and extracted with ethyl acetate three times. The combined extract was washed with brine, dried. (anh. Na$_2$SO$_4$), filtered, concentrated, and column chromatographed on silica gel using a gradient mixture of hexane and ethyl acetate as eluent to give 12.0 g (83% yield) of the titled compound (mainly β-anomer): $^1$H NMR (CDCl$_3$): δ5.39 (s, 1H), 4.80 (d, J=8 Hz, 1H), 4.56 (d, J=8 Hz, 1H), 4.39 (t, J=4 Hz, 1H), 3.69 (t J=4 Hz, 2H), 1.68 (q, J=8 Hz, 2H), 1.56 (d, J=8 Hz, 2H), 0.89 (t, J=8 Hz, 3H). 0.85 (t, J=8 Hz, 3H); $^{13}$C NMR$^7$ (CDCl$_3$): δ116.6, 103.0, 88.0, 87.2, 82.0, 63.7, 29.3, 28.9, 8.5, 7.5.

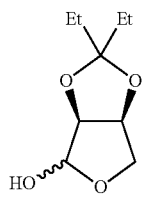

(3aS,6aS)-2,2-Diethyl-tetrahydrofuro[3,4-d][1,3]dioxol-4-ol. To a cold (0° C.) solution of 6.40 g (0.029 mol) of the pentylidene in 50 mL of ethanol and 100 mL of water was added dropwise of a cold (0° C.) solution of 1.20 g (0.032 mol) of sodium borohydride in 100 mL of water and stirred at 25° C. for 14 h. To it, 12 mL of 10% aqueous acetic acid solution was added to adjust the pH to ~5. The solution was diluted with 80 mL of water, cooled over ice-water bath, and added 6.9 g (0.032 mol) of NaIO$_4$ in portions over 5 minutes. The reaction solution was stirred at 25° C. for 3 h, concentrated on a rotary to evaporator to 50 mL, and extracted with ethyl acetate four times (50 mL each). The combined extracts were washed with water, brine, dried (anhydrous Na$_2$SO$_4$), concentrated to dryness to give 5.01 g (91% yield) of the titled molecule. This compound was used in the following step without further purification. $[α]_D^{22}$=+49.91 (c 1.0, CHCl$_3$). $^1$H NMR (CDCl$_3$): δ5.43 (s, 1H), 4.83 (dd, J=4, 1 Hz, 1H), 4.57 (d, J=4 Hz, 1H), 4.07-4.03 (m, 2H), 1.68 (q, J=8 Hz, 2H), 1.57 (q, J=8 Hz, 2H), 0.89 (t, J=8 Hz, 3H), 0.87 (t, J=8 Hz, 3H); $^{13}$C NMR (CDCl$_3$): δ116.8, 101.9, 85.6, 80.4, 72.2, 29.4, 28.9, 8.6, 7.5.

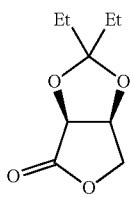

(3aS,6aS)-2,2-Diethyl-dihydrofuro[3,4-d][1,3]dioxol-4(3aH)-one. To a dried flask containing 3 Å molecular sieves and 80 mL of dichloromethane under argon at −78° C., were added 6.67 g (50 mmol) of freshly distilled oxalyl chloride followed by a solution of 8.2 g (0.10 mol) of dry DMSO in 25 mL of dichloromethane. The reaction mixture was stirred at −78° C. for 15 min. To it was added a solution of 2.00 g (10.05 mmol) of the lactol in 25 mL of dichloromethane, stirred for 0.5 h, and added 16 g (0.15 mol) of triethylamine. The mixture was stirred at −78° C. for 0.5 h and 25° C. for 14 h, diluted with water (60 mL), acidified with 1N HCl to pH 2, and extracted with dichloromethane (100 mL each) three times. The combined extract was washed with aqueous NH₄Cl, water and brine, dried (anhydrous Na₂SO₄), concentrated, and column chromatographed on silica gel using a gradient mixture of hexane and ethyl acetate as eluent to give 1.60 g (80% yield) of the desired lactone and 0.20 g (11% recovery) of starting material, (3aS,6aS)-2,2-diethyl-tetrahydrofuro[3,4-d][1,3]dioxol-4-ol. Title compound: $[\alpha]_D^{20}$=+106.0 (c 1.08, CHCl₃); ¹H NMR (CDCl₃): δ4.89 (dd, 5.8, 3.8 Hz, 1H), 476 (d, J=5.8 Hz, 1H), 4.48 (d, J=11.0 Hz, 1H), 4.39 (dd, J=11.0, 3.9 Hz, 1H), 1.69 (q, J=8 Hz, 3H), 1.67 (q, J=8 Hz, 2H), 0.90 (t, J=8 Hz, 3H), 0.88 (t, J=8 Hz, 3H). ¹³C NMR (CDCl₃): δ174.6, 118.1, 76.1, 75.2, 70.8, 29.9, 29.4, 8.3, 7.4.

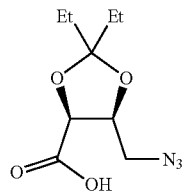 [SMILES: CCC1(CC)O[C@@H](CN=[N+]=[N-])[C@@H](C(=O)O)O1]

(4S,5S)-5-(Azidomethyl)-2,2-diethyl-1,3-dioxolane-4-carboxylic acid. To a flame dried flask, was added the above lactone (2.60 g, 14 mmol) and NaN₃ (5.45 g, 83.9 mmol) under argon at room temperature. The mixture was dried under vacuum for 30 min, then anhydrous DMF (15 mL) was added and heated at 120° C. with stirring for 12 hr. The reaction mixture was cooled to room temperature and added H₂O (40 mL), extracted with dichloromethane three times (80 mL each). The combined organic layer was washed with brine, dried (anhydrous Na₂SO₄), and concentrated to recover 0.40 g (15% recovery) of starting lactone. The aqueous layer was acidified with 1 N HCl to pH 2.0 and extracted five times with dichloromethane (80 mL each). The combined organic layer was washed with brine, dried (anhydrous Na₂SO₄), concentrated, and column chromatographed on silica gel using a mixture of CH₂Cl₂ and MeOH (10:1) as an eluent to give 0.67 g (68% yield) of (4S,5S)-5-(azidomethyl)-2,2-diethyl-1,3-dioxolane-4-carboxylic acid as a colorless oil, $[\alpha]_D^{22}$=−65.7 (c 1.5, CHCl₃). ¹H NMR (CDCl₃): δ9.25-8.80 (br s, 1H), 4.68 (d, J=8.0 Hz, 1H), 4.60 (ddd, J=8.0, 5.9, 3.3 Hz, 1H), 3.58 (d, J=11 Hz, 1H), 3.40 (dd, J=11, 7 Hz, 1H), 1.80 (q, J=8 Hz, 2H), 1.62 (q, J=8 Hz, 2H), 1.00 (t, J=7.5 Hz, 3H), 0.92 (t, J=7.5 Hz, 3H); ¹³C NMR. (CDCl₃): δ173.7, 115.8, 76.6, 74.6, 50.6, 29.0, 28.3, 8.6, 8.0.

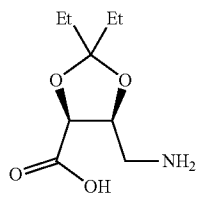 [SMILES: CCC1(CC)O[C@@H](CN)[C@@H](C(=O)O)O1]

(4S,5S)-5-(Aminomethyl)-2,2-diethyl-1,3-dioxolane-4-carboxylic acid. To a hydrogenation flask, was added (4S,5S)-5-(azidomethyl)-2,2-diethyl-1,3-dioxolane-4-carboxylic acid (230 mg, 1 mmol), MeOH (20 mL) and 5% Pd/C (20 mg), then the mixture was shaked under 30 psi H₂ at room temperature for 12 hr. The reaction mixture was maintained under normal pressure, filtered through Celite, washed with methanol, and concentrated to give 200 mg (98% yield) of the title molecule as a white solid: m. p. 130~131° C.; $[\alpha]_D^{22}$=−62.4 (c 1.7, MeOH); ¹H NMR (DMSO-d₆) δ4.43 (d, J=7.2 Hz, 1H), 4.34 (td, J=7.1, 4.8 Hz, 1H), 2.75 (qd, J=12.8, 6.1 Hz, 2H), 1.62 (q, J=7.4 Hz, 2H), 1.56-1.45 (m, 2H), 0.85 (t, J=7.4 Hz, 3H), 0.79 (t, J=7.4 Hz, 3H), ¹³C NMR (DMSO-d₆): δ169.4, 111.9, 78.3, 72.9, 40.9 (CH₂N), 28.7, 28.0, 8.6, 7.9. The compound was used in the following reaction without purification.

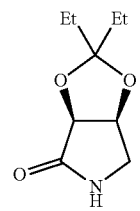

(3aS,6aS)-2,2-Diethyl-dihydro-3aH-[1,3]dioxolo[4,5-c]pyrrol-4(5H)-one (4SB). To a sublimation tube, 180 mg (0.89 mmol) of (4S,5S)-5-(aminomethyl)-2,2-diethyl-1,3-dioxolane-4-carboxylic acid was added. The chemical was stirred and heated to 150° C. under high vacuum (0.1 mm Hg). Compound 4SB (130 mg, 79% yield) was collected from the cooling tube (cooled with thy ice-acetone) as white needle-like crystals, m.p. 134~139° C.; $[\alpha]_D^{20}$=+65.0 (c 1.0, chloroform); ¹H NMR (CDCl₃): δ7.20-6.85 (bs, 1H, NH), 4.77 (t, J=5.4 Hz, 1H), 4.57 (d, J=6.0 Hz, 1H), 3.54 (dd, J=11.5, 4.7 Hz, 1H), 3.48 (d, J=11.5 Hz, 1H), 1.72 (q, J=7.4 Hz, 2H), 1.62 (q, J=7.4 Hz, 2H), 0.91 (t, J=7.4 Hz, 3H), 0.87 (t, J=7.4 Hz, 3H); ¹³C NMR (CDCl₃): δ174.8, 117.1, 77.23, 75.1, 46.4, 30.2, 29.7, 8.5, 7.6, MS (ESI, MeOH): m/z=186.0 ([M+H]⁺). HRMS-ESI: m/z [M+H]⁺ calcd for C₉H₁₆NO₃⁺: 186.1124, found: 186.1132.

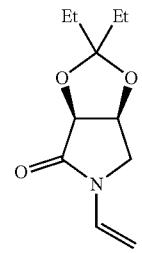

(3aS,6aS)-5-Vinyl-{2,2-diethyl-dihydro-3aH-[1,3]dioxolo[4,5-c]pyrrol}-4(5H)-one (6S). To a round-bottom flask, 129 mg (0.70 mmol) of 4SB and 10 mL of n-butyl vinyl ether (distilled) were added. The mixture sonicated for few minutes to provide a clear to solution. To it, was added 22 mg (0.035 mmol) of 4,7-diphenyl-1,10-phenanthroline palladium bis(trifluoroacetate) [(DPP)Pd(OCOCF₃)₂]⁵ and the solution was stirred at 75° C. for 3 h. The mixture was cooled to 25° C., filtered through a small layer of silica gel, washed with ethyl acetate, concentrated, and purified by silica gel column chromatography with a mixture of hexane/ethyl acetate (5:1) as eluent to give 0.135 g (92% yield) of 6S as a white solid. $[\alpha]_D^{22}$=+43.2 (c 1.0, CHCl₃; ¹H NMR δ7.07 (dd, J=16.0, 9.2 Hz, 1H, CH=), 4.84-4.81 (m, 1H), 4.72 (d, J=6.4 Hz, 1H), 4.55 (d, J=9.2 Hz, 1H, =CH$_2$), 4.49 (d, J=16 Hz, 1H, =CH$_2$), 3.64 (d, J=2.8 Hz, 1H), 3.63 (d, J=2.8 Hz, 1H), 1.70 (q, J=7.2 Hz, 2H), 1.65 (q, J=7.2 Hz, 2H), 0.91 (t, J=6 Hz, 6H); $^{13}$C NMR δ169.3, 128.8, 115.5, 96.6, 78.0, 71.9, 48.6, 30.0, 29.6, 8.4, 7.6. MS (ESI, MeOH): m/z=212.2 ([M+H]$^+$), 234.3 ([M+Na]$^+$). HRMS-ESI: m/z [M+H]$^+$ calcd for C$_{11}$H$_{18}$NO$_3$$^+$: 212.1287 found: 212.1269.

The lactone was used in the preparation of polymers 1S and 2S as described in Scheme 1A by following the same sequence of reactions as depicted Scheme 1 for the syntheses of polymers 1 and 2.

Representative C—H Bond Oxidation of Complex Molecules Using Cu/Au (3:1)-2 and H$_2$O$_2$ Bimetallic nanocluster Cu/Au (3:1; 7.5 μmol of Cu, 2.5 μmol of Au, and 0.28 μmol of 2) stabilized CSPVP 2 was prepared in water as described above. To it was added 70.8 mg (0.2 mmol) of estrone pivalate ester (132), 3 mL of H$_2$O$_2$, and 2 mL of acetonitrile. The reaction solution was stirred at 50° C. for 6 days, cooled to room temperature, diluted with water, and extracted with diethyl ether three times (30 mL each). The combined extracts were washed with brine, dried (anhydrous Na$_2$SO$_4$), concentrated, and column chromatographed on silica gel using a gradient mixture of hexane and diethyl ether as eluent to give 42.6 mg (68% yield based on recovered 132) of 132A and 11 mg (15% recovery) of compound 132. The NMR spectral data is identical to that reported.

I claim:

1. A chiral substituted polyvinylpyrrolidinone compound having the formula

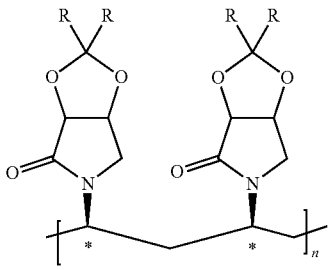

wherein each R is individually selected from the group consisting of OH and C1-C30 aliphatic and aromatic functional groups, and n is greater than 50.

2. The compound of claim 1, wherein at least two R groups are identical.

3. The compound of claim 1, wherein the compound has the formula

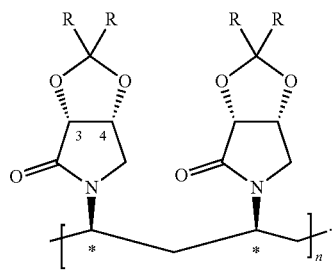

4. The compound of claim 1, wherein the compound has the formula

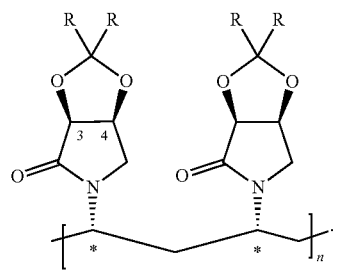

5. The compound of claim 1, wherein each R group is selected from the group consisting of ethers, aliphatic hydrocarbons, and aromatic hydrocarbons.

6. The compound of claim 1, wherein each R group is selected from the group consisting of CH$_3$, CH$_2$CH$_3$, CH(CH$_3$)$_2$, CH (cyclohexyl)$_2$, Ph, CH$_2$Ph, CH$_2$O-t-Bu, CH$_2$ (1-Naph), CH$_2$OH, and CH$_2$OCHPh$_2$.

7. The compound of claim 1, wherein the compound comprises

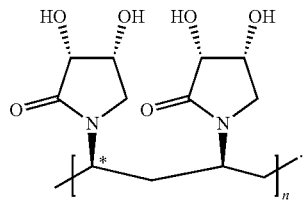

8. The compound of claim 1, wherein the compound has a molecular weight of at least 50,000 g/mol and wherein n is from 50 to about 500.

9. A complex comprising the chiral substituted polyvinylpyrrolidinone compound of claim 1 bound to a core species selected from the group consisting of nanoparticulate materials, proteins, DNA, siRNA, and dsRNA.

10. The complex of claim 9, wherein the complex comprises a nanoparticle cluster, and wherein the nanoparticle cluster comprises one or more metals selected from the group consisting of Au, Pd, Cu, Rh, Ce, Mo, Ni, Ru, W, and Fe.

11. The complex of claim 1, wherein the nanoparticle cluster is bimetallic and is selected from the group consisting of Pd/Au, Cu/Au, Rh/Au, Ce/Au, Mo/Au, W/Au, Ru/Au, and Fe/Au.

12. The complex of claim 9, wherein the chiral substituted polyvinylpyrrolidinone compound encapsulates the core species.

13. A method of asymmetrically oxidizing organic molecules comprising reacting the organic molecule with one or more reagents in the presence of a complex comprising the chiral substituted polyvinylpyrrolidinone compound of claim 1 bound to a metallic nanocluster to produce chiral molecules.

14. The method of claim 13, wherein the organic molecule is an alkene or cycloalkane, and the reaction results in the oxidation of a carbon-carbon double bond producing chiral diols.

15. The method of claim 13, wherein the organic molecule is an alkane or cycloalkane, and the reaction oxidizes a carbon-hydrogen bond in the alkane or cycloalkane to form a chiral alcohol or ketone molecule possessing a hydroxyl or carbonyl functional group.

16. The method of claim 13, wherein the organic molecule comprises an alkene, and the reaction comprises a ring-closing reaction resulting in the formation of a lactone or lactam.

17. The method of claim 13, wherein the reaction generates a reaction product comprising two enantiomers, and wherein the enantiomeric excess of one of the enantiomers is greater than 50%.

18. The method of claim 17, wherein the reaction generates a reaction product that is enantiopure.

19. The method of claim 13, wherein the reaction generates a reaction product having a hydroxyl or ketone functional group, and wherein the reaction product is further reacted with an organic compound in which the organic compound is added to the reaction product at the site of the hydroxyl or ketone functional group.

20. The method of claim 13, wherein the nanocluster comprises one or more metals selected from the group consisting of Au, Pd, Cu, Rh, Ce, Mo, Ni, Ru, W, and Fe.

21. The method of claim 20, wherein the nanocluster is bimetallic and is selected from the group consisting of Pd/Au, Cu/Au, Rh/Au, Ce/Au, Mo/Au, Ni/Au, W/Au, Ru/Au, and Fe/Au.

22. A compound produced by reacting a substrate with one or more reagents in the presence of a complex comprising the chiral substituted polyvinylpyrrolidinone compound of claim 1 bound to a metallic nanocluster.

23. The compound of claim 22, wherein the compound comprises an enantiomeric excess of greater than 80% without having undergone a separate separation step to isolate a particular enantiomer.

24. A method of synthesizing the chiral substituted polyvinylpyrrolidinone compound of claim 1 from D-isoascorbic acid comprising:
   converting the isoascorbic acid to a pyrrolidinone through a sequence of (i) oxidative cleavage of the isoascorbic acid to produce a D-erthronolactone, (ii) ketalization of the D-erthronolactone to produce a ketalized lactone, (iii) $S_N2$-type ring opening of the ketalized lactone, and (iv) reduction of an azido functional group;
   converting the pyrrolidinone to an N-vinylpyrrolidinone through an N-vinylation reaction; and
   polymerizing the N-vinylpyrrolidinone to form the chiral substituted polyvinylpyrrolidinone compound of claim 1.

25. A method of synthesizing the chiral substituted polyvinylpyrrolidinone compound of claim 1 from D-ribose comprising
   converting the D-ribose into an acetonide sugar;
   reacting the acetonide sugar to produce a lactol;
   oxidizing the lactol with pyridinium chlorochromate to produce a lactone;
   reacting the lactone with dimethylformamide to produce a pyrrolidinone;
   converting the pyrrolidinone to an N-vinylpyrrolidinone through an N-vinylation reaction; and
   polymerizing the N-vinylpyrrolidinone to form the chiral substituted polyvinylpyrrolidinone compound of claim 1.

* * * * *